United States Patent [19]
Reyes et al.

[11] Patent Number: 5,824,649
[45] Date of Patent: Oct. 20, 1998

[54] DNA SEQUENCES OF ENTERICALLY TRANSMITTED NON-A/NON-B HEPATITIS VIRAL AGENT AND CHARACTERISTIC EPITOPES THEREOF

[75] Inventors: Gregory R. Reyes, Palo Alto; Patrice O. Yarbough, Redwood Shores, both of Calif.; Daniel W. Bradley, Lawrenceville; Krzysztof Z. Krawczynski, Tucker, both of Ga.; Albert Tam, San Francisco; Kirk E. Fry, Palo Alto, both of Calif.

[73] Assignee: Genelabs Technologies, Inc., Redwood City, Calif.

[21] Appl. No.: 475,807

[22] Filed: Jun. 7, 1995

Related U.S. Application Data

[60] Division of Ser. No. 279,823, Jul. 25, 1994, which is a continuation-in-part of Ser. No. 505,888, Jul. 5, 1990, abandoned, which is a continuation-in-part of Ser. No. 420,921, Oct. 13, 1989, abandoned, which is a continuation-in-part of Ser. No. 367,486, Jun. 16, 1989, abandoned, which is a continuation-in-part of Ser. No. 336,672, Apr. 11, 1989, abandoned, which is a continuation-in-part of Ser. No. 208,997, Jun. 17, 1988, abandoned.

[51] Int. Cl.$^6$ .............. A61K 38/00; C07K 1/00; C07H 21/04; C12P 21/06
[52] U.S. Cl. .............. 514/12; 530/350; 530/324; 536/23.72; 435/69.1
[58] Field of Search .............. 530/350, 324, 530/325, 826; 536/23.72; 435/69.1, 69.3, 6, 7.1, 7.6; 514/12

[56] References Cited

U.S. PATENT DOCUMENTS

| | | | |
|---|---|---|---|
| 4,659,678 | 4/1987 | Forrest et al. | 436/512 |
| 4,683,195 | 7/1987 | Mullis et al. | 435/6 |
| 4,870,026 | 9/1989 | Wands et al. | 435/5 |
| 4,871,659 | 10/1989 | Pillot | 435/5 |
| 5,077,193 | 12/1991 | Mishire et al. | 435/5 |

FOREIGN PATENT DOCUMENTS

| | | |
|---|---|---|
| 2 606 515 | 5/1988 | France . |
| 2 609 807 | 6/1988 | France . |
| 85/01517 | 4/1985 | WIPO . |
| 88/03410 | 5/1988 | WIPO . |
| 89/12641 | 12/1989 | WIPO . |

OTHER PUBLICATIONS

Sarthou, J.I., et al., "Characterization of an Antigen–Antibody System Associated with Epidemic Non–A, Non–B Hepatitis in West Africa and Experimental Transmission of an Infectious Agent to Primates," *Ann. Inst. Pasteur/Virol.* 137(F): 225–232 (1986).

*Primary Examiner*—Robert A. Wax
*Assistant Examiner*—Tekchand Saidha
*Attorney, Agent, or Firm*—Charles K. Sholtz; Gary R. Fabian; Peter J. Dehlinger

[57] ABSTRACT

Viral proteins derived from an enterically transmitted non-A/non-B viral hepatitis agent (HEV) are disclosed. In one embodiment, the protein is immunologically reactive with antibodies present in individuals infected with the viral hepatitis agent. This protein is useful in a diagnostic method for detecting infection by the enterically transmitted agent. Specific epitopes have been identified that are reactive with sera of individual infected with different strains of HEV. Also disclosed are DNA probes derived from a cloned sequence of the viral agent. These probes are useful for identifying and sequencing the entire viral agent and for assaying the presence of the viral agent in an infected sample, by using probe-specific amplification of virus-derived DNA fragments.

35 Claims, 2 Drawing Sheets

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 1295 base pairs
( B ) TYPE: nucleic acid
( C ) STRANDEDNESS: double
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: 1.33 kb EcoRI insert of ET1.1, forward sequence ( i x ) FEATURE:
( A ) NAME/KEY: CDS
( B ) LOCATION: 1..1293

( i x ) FEATURE:
( A ) NAME/KEY: CDS
( B ) LOCATION: 2..1294

( i x ) FEATURE:
( A ) NAME/KEY: CDS
( B ) LOCATION: 3..1295

( x i ) SEQUENCE DESCRIPTION: SEQ ID NO:1:

```
AGACCTGTCC CTGTTGCAGC TGTTCTACCA CCCTGCCCCG AGCTCGAACA GGGCCTTCTC    60
TACCTGCCCC AGGAGCTCAC CACCTGTGAT AGTGTCGTAA CATTTGAATT AACAGACATT   120
GTGCACTGCC GCATGGCCGC CCCGAGCCAG CGCAAGGCCG TGCTGTCCAC ACTCGTGGGC   180
```

-continued

```
CGCTACGGCG GTCGCACAAA GCTCTACAAT GCTTCCCACT CTGATGTTCG CGACTCTCTC    240
GCCCGTTTTA TCCCGGCCAT GGCCCCGTA CAGGTTACAA CTTGTGAATT GTACGAGCTA    300
GTGGAGGCCA TGGTCGAGAA GGGCCAGGAT GGCTCCGCCG TCCTTGAGCT TGATCTTTGC    360
AACCGTGACG TGTCCAGGAT CACCTTCTTC CAGAAAGATT GTAACAAGTT CACCACAGGT    420
GAGACCATTG CCCATGGTAA AGTGGGCCAG GGCATCTCGG CCTGGAGCAA GACCTTCTGC    480
GCCCTCTTTG GCCCTTGGTT CCGCGCTATT GAGAAGGCTA TTCTGGCCCT GCTCCCTCAG    540
GGTGTGTTTT ACGGTGATGC CTTTGATGAC ACCGTCTTCT CGGCGGCTGT GGCCGCAGCA    600
AAGGCATCCA TGGTGTTTGA GAATGACTTT TCTGAGTTTG ACTCCACCCA GAATAACTTT    660
TCTCTGGGTC TAGAGTGTGC TATTATGGAG GAGTGTGGGA TGCCGCAGTG GCTCATCCGC    720
CTGTATCACC TTATAAGGTC TGCGTGGATC TTGCAGGCCC CGAAGGAGTC TCTGCGAGGG    780
TTTTGGAAGA AACACTCCGG TGAGCCCGGC ACTCTTCTAT GGAATACTGT CTGGAATATG    840
GCCGTTATTA CCCACTGTTA TGACTTCCGC GATTTTCAGG TGGCTGCCTT TAAAGGTGAT    900
GATTCGATAG TGCTTTGCAG TGAGTATCGT CAGAGTCCAG GAGCTGCTGT CCTGATCGCC    960
GGCTGTGGCT TGAAGTTGAA GGTAGATTTC CGCCCGATCG GTTTGTATGC AGGTGTTGTG   1020
GTGGCCCCCG GCCTTGGCGC GCTCCCTGAT GTTGTGCGCT TCGCCGGCCG GCTTACCGAG   1080
AAGAATTGGG GCCCTGGCCC TGAGCGGGCG GAGCAGCTCC GCCTCGCTGT TAGTGATTTC   1140
CTCCGCAAGC TCACGAATGT AGCTCAGATG TGTGTGGATG TTGTTTCCCG TGTTTATGGG   1200
GTTTCCCCTG GACTCGTTCA TAACCTGATT GGCATGCTAC AGGCTGTTGC TGATGGCAAG   1260
GCACATTTCA CTGAGTCAGT AAAACCAGTG CTCGA                              1295
```

(2) INFORMATION FOR SEQ ID NO:2:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:2:

```
Arg Pro Val Pro Val Ala Ala Val Leu Pro Pro Cys Pro Glu Leu Glu
  1               5                  10                  15

Gln Gly Leu Leu Tyr Leu Pro Gln Glu Leu Thr Thr Cys Asp Ser Val
             20                  25                  30

Val Thr Phe Glu Leu Thr Asp Ile Val His Cys Arg Met Ala Ala Pro
         35                  40                  45

Ser Gln Arg Lys Ala Val Leu Ser Thr Leu Val Gly Arg Tyr Gly Gly
     50                  55                  60

Arg Thr Lys Leu Tyr Asn Ala Ser His Ser Asp Val Arg Asp Ser Leu
 65                  70                  75                  80

Ala Arg Phe Ile Pro Ala Ile Gly Pro Val Gln Val Thr Thr Cys Glu
                 85                  90                  95

Leu Tyr Glu Leu Val Glu Ala Met Val Glu Lys Gly Gln Asp Gly Ser
            100                 105                 110

Ala Val Leu Gln Leu Asp Leu Cys Asn Arg Asp Val Ser Arg Ile Thr
        115                 120                 125

Phe Phe Gln Lys Asp Cys Asn Lys Phe Thr Thr Gly Glu Thr Ile Ala
130                 135                 140

His Gly Lys Val Gly Gln Gly Ile Ser Ala Trp Ser Lys Thr Phe Cys
145                 150                 155                 160
```

```
Ala  Leu  Phe  Gly  Pro  Trp  Phe  Arg  Ala  Ile  Glu  Lys  Ala  Ile  Leu  Ala
                    165                      170                     175

Leu  Leu  Pro  Gln  Gly  Val  Phe  Tyr  Gly  Asp  Ala  Phe  Asp  Thr  Val
                    180                      185                     190

Phe  Ser  Ala  Ala  Val  Ala  Ala  Ala  Lys  Ala  Ser  Met  Val  Phe  Glu  Asn
               195                      200                     205

Asp  Phe  Ser  Glu  Phe  Asp  Ser  Thr  Gln  Asn  Asn  Phe  Ser  Leu  Gly  Leu
     210                      215                     220

Glu  Cys  Ala  Ile  Met  Glu  Glu  Cys  Gly  Met  Pro  Gln  Trp  Leu  Ile  Arg
225                      230                     235                          240

Leu  Tyr  His  Leu  Ile  Arg  Ser  Ala  Trp  Ile  Leu  Gln  Ala  Pro  Lys  Glu
                    245                     250                     255

Ser  Leu  Arg  Gly  Phe  Trp  Lys  Lys  His  Ser  Gly  Glu  Pro  Gly  Thr  Leu
               260                     265                     270

Leu  Trp  Asn  Thr  Val  Trp  Asn  Met  Ala  Val  Ile  Thr  His  Cys  Tyr  Asp
               275                     280                     285

Phe  Arg  Asp  Phe  Gln  Val  Ala  Ala  Phe  Lys  Gly  Asp  Asp  Ser  Ile  Val
     290                     295                     300

Leu  Cys  Ser  Glu  Tyr  Arg  Gln  Ser  Pro  Gly  Ala  Ala  Val  Leu  Ile  Ala
305                      310                     315                          320

Gly  Cys  Gly  Leu  Lys  Leu  Lys  Val  Asp  Phe  Arg  Pro  Ile  Gly  Leu  Tyr
                    325                     330                     335

Ala  Gly  Val  Val  Val  Ala  Pro  Gly  Leu  Gly  Ala  Leu  Pro  Asp  Val  Val
               340                     345                     350

Arg  Phe  Ala  Gly  Arg  Leu  Thr  Glu  Lys  Asn  Trp  Gly  Pro  Gly  Pro  Glu
          355                     360                     365

Arg  Ala  Glu  Gln  Leu  Arg  Leu  Ala  Val  Ser  Asp  Phe  Leu  Arg  Lys  Leu
     370                     375                     380

Thr  Asn  Val  Ala  Gln  Met  Cys  Val  Asp  Val  Val  Ser  Arg  Val  Tyr  Gly
385                      390                     395                          400

Val  Ser  Pro  Gly  Leu  Val  His  Asn  Leu  Ile  Gly  Met  Leu  Gln  Ala  Val
               405                     410                     415

Ala  Asp  Gly  Lys  Ala  His  Phe  Thr  Glu  Ser  Val  Lys  Pro  Val  Leu
               420                     425                     430
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: linker - top (5') sequence ( x i ) SEQUENCE DESCRIPTION: SEQ ID NO:3:

```
GGAATTCGCG  GCCGCTCG                                                        18
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (ii) MOLECULE TYPE: DNA (iii) HYPOTHETICAL: NO (iv) ANTI-SENSE: NO (vi) ORIGINAL SOURCE:
 (C) INDIVIDUAL ISOLATE: linker - bottom (3') sequence (xi) SEQUENCE DESCRIPTION: SEQ ID NO:4:

CGAGCGGCCG CGAATTCCTT                                                                            20

(2) INFORMATION FOR SEQ ID NO:5:

(i) SEQUENCE CHARACTERISTICS:
 (A) LENGTH: 1295 base pairs
 (B) TYPE: nucleic acid
 (C) STRANDEDNESS: double
 (D) TOPOLOGY: linear (ii) MOLECULE TYPE: DNA (iii) HYPOTHETICAL: NO (iv) ANTI-SENSE: NO (vi) ORIGINAL SOURCE:
 (C) INDIVIDUAL ISOLATE: 1.33 kb EcoRI insert of ET1.1,
  reverse sequence (xi) SEQUENCE DESCRIPTION: SEQ ID NO:5:

| | | | | | |
|---|---|---|---|---|---|
| TCGAGCACTG | GTTTACTGA | CTCAGTGAAA | TGTGCCTTGC | CATCAGCAAC | AGCCTGTAGC | 60 |
| ATGCCAATCA | GGTTATGAAC | GAGTCCAGGG | GAAACCCAT | AAACACGGGA | AACAACATCC | 120 |
| ACACACATCT | GAGCTACATT | CGTGAGCTTG | CGGAGGAAAT | CACTAACAGC | GAGGCGGAGC | 180 |
| TGCTCCGCCC | GCTCAGGGCC | AGGGCCCCAA | TTCTTCTCGG | TAAGCCGGCC | GGCGAAGCGC | 240 |
| ACAACATCAG | GGAGCGCGCC | AAGGCCGGGG | GCCACCACAA | CACCTGCATA | CAAACCGATC | 300 |
| GGGCGGAAAT | CTACCTTCAA | CTTCAAGCCA | CAGCCGGCGA | TCAGGACAGC | AGCTCCTGGA | 360 |
| CTCTGACGAT | ACTCACTGCA | AAGCACTATC | GAATCATCAC | CTTTAAAGGC | AGCCACCTGA | 420 |
| AAATCGCGGA | AGTCATAACA | GTGGGTAATA | ACGGCCATAT | TCCAGACAGT | ATTCCATAGA | 480 |
| AGAGTGCCGG | GCTCACCGGA | GTGTTTCTTC | CAAAACCCTC | GCAGAGACTC | CTTCGGGGCC | 540 |
| TGCAAGATCC | ACGCAGACCT | TATAAGGTGA | TACAGGCGGA | TGAGCCACTG | CGGCATCCCA | 600 |
| CACTCCTCCA | TAATAGCACA | CTCTAGACCC | AGAGAAAAGT | TATTCTGGGT | GGAGTCAAAC | 660 |
| TCAGAAAAGT | CATTCTCAAA | CACCATGGAT | GCCTTTGCTG | CGGCCACAGC | CGCCGAGAAG | 720 |
| ACGGTGTCAT | CAAAGGCATC | ACCGTAAAAC | ACACCCTGAG | GGAGCAGGGC | CAGAATAGCC | 780 |
| TTCTCAATAG | CGCGGAACCA | AGGGCCAAAG | AGGGCGCAGA | AGGTCTTGCT | CCAGGCCGAG | 840 |
| ATGCCCTGGC | CCACTTTACC | ATGGGCAATG | GTCTCACCTG | TGGTGAACTT | GTTACAATCT | 900 |
| TTCTGGAAGA | AGGTGATCCT | GGACACGTCA | CGGTTGCAAA | GATCAAGCTC | AAGGACGGCG | 960 |
| GAGCCATCCT | GGCCCTTCTC | GACCATGGCC | TCCACTAGCT | CGTACAATTC | ACAAGTTGTA | 1020 |
| ACCTGTACGG | GGCCAATGGC | CGGGATAAAA | CGGGCGAGAG | AGTCGCGAAC | ATCAGAGTGG | 1080 |
| GAAGCATTGT | AGAGCTTTGT | GCGACCGCCG | TAGCGGCCCA | CGAGTGTGGA | CAGCACGGCC | 1140 |
| TTGCGCTGGC | TCGGGCGGC | CATGCGGCAG | TGCACAATGT | CTGTTAATTC | AAATGTTACG | 1200 |
| ACACTATCAC | AGGTGGTGAG | CTCCTGGGGC | AGGTAGAGAA | GGCCCTGTTC | GAGCTCGGGG | 1260 |
| CAGGGTGGTA | GAACAGCTGC | AACAGGGACA | GGTCT | | | 1295 |

( 2 ) INFORMATION FOR SEQ ID NO:6:

( i ) SEQUENCE CHARACTERISTICS:
        ( A ) LENGTH: 7195 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HEV - Burma strain ( i x ) FEATURE:
        ( A ) NAME/KEY: CDS
        ( B ) LOCATION: 28..5106

( i x ) FEATURE:
        ( A ) NAME/KEY: CDS
        ( B ) LOCATION: 5147..7126

( i x ) FEATURE:
        ( A ) NAME/KEY: CDS
        ( B ) LOCATION: 5106..5474

( x i ) SEQUENCE DESCRIPTION: SEQ ID NO:6:

```
AGGCAGACCA  CATATGTGGT  CGATGCCATG  GAGGCCCATC  AGTTTATTAA  GGCTCCTGGC      60
ATCACTACTG  CTATTGAGCA  GGCTGCTCTA  GCAGCGGCCA  ACTCTGCCCT  GGCGAATGCT     120
GTGGTAGTTA  GGCCTTTTCT  CTCTCACCAG  CAGATTGAGA  TCCTCATTAA  CCTAATGCAA     180
CCTCGCCAGC  TTGTTTTCCG  CCCCGAGGTT  TTCTGGAATC  ATCCATCCA   GCGTGTCATC     240
CATAACGAGC  TGGAGCTTTA  CTGCCGCGCC  CGCTCCGGCC  GCTGTCTTGA  AATTGGCGCC     300
CATCCCCGCT  CAATAAATGA  TAATCCTAAT  GTGGTCCACC  GCTGCTTCCT  CCGCCCTGTT     360
GGGCGTGATG  TTCAGCGCTG  GTATACTGCT  CCCACTCGCG  GGCCGGCTGC  TAATTGCCGG     420
CGTTCCGCGC  TGCGCGGGCT  TCCCGCTGCT  GACCGCACTT  ACTGCCTCGA  CGGGTTTTCT     480
GGCTGTAACT  TTCCCGCCGA  GACTGGCATC  GCCCTCTACT  CCCTTCATGA  TATGTCACCA     540
TCTGATGTCG  CCGAGGCCAT  GTTCCGCCAT  GGTATGACGC  GGCTCTATGC  CGCCCTCCAT     600
CTTCCGCCTG  AGGTCCTGCT  GCCCCCTGGC  ACATATCGCA  CCGCATCGTA  TTTGCTAATT     660
CATGACGGTA  GGCGCGTTGT  GGTGACGTAT  GAGGGTGATA  CTAGTGCTGG  TTACAACCAC     720
GATGTCTCCA  ACTTGCGCTC  CTGGATTAGA  ACCACCAAGG  TTACCGGAGA  CCATCCCCTC     780
GTTATCGAGC  GGGTTAGGGC  CATTGGCTGC  CACTTTGTTC  TCTTGCTCAC  GGCAGCCCCG     840
GAGCCATCAC  CTATGCCTTA  TGTTCCTTAC  CCCCGGTCTA  CCGAGGTCTA  TGTCCGATCG     900
ATCTTCGGCC  CGGGTGGCAC  CCCTTCCTTA  TTCCCAACCT  CATGCTCCAC  TAAGTCGACC     960
TTCCATGCTG  TCCCTGCCCA  TATTTGGGAC  CGTCTTATGC  TGTTCGGGGC  CACCTTGGAT    1020
GACCAAGCCT  TTTGCTGCTC  CCGTTTAATG  ACCTACCTTC  GCGGCATTAG  CTACAAGGTC    1080
ACTGTTGGTA  CCCTTGTGGC  TAATGAAGGC  TGGAATGCCT  CTGAGGACGC  CCTCACAGCT    1140
GTTATCACTG  CCGCCTACCT  TACCATTTGC  CACCAGCGGT  ATCTCCGCAC  CCAGGCTATA    1200
TCCAAGGGGA  TGCGTCGTCT  GGAACGGGAG  CATGCCCAGA  AGTTTATAAC  ACGCCTCTAC    1260
AGCTGGCTCT  TCGAGAAGTC  CGGCCGTGAT  TACATCCCTG  GCCGTCAGTT  GGAGTTCTAC    1320
GCCCAGTGCA  GGCGCTGGCT  CTCCGCCGGC  TTTCATCTTG  ATCCACGGGT  GTTGGTTTTT    1380
GACGAGTCGG  CCCCCTGCCA  TTGTAGGACC  GCGATCCGTA  AGGCGCTCTC  AAAGTTTTGC    1440
```

-continued

```
TGCTTCATGA AGTGGCTTGG TCAGGAGTGC ACCTGCTTCC TTCAGCCTGC AGAAGGCGCC    1500
GTCGGCGACC AGGGTCATGA TAATGAAGCC TATGAGGGGT CCGATGTTGA CCCTGCTGAG    1560
TCCGCCATTA GTGACATATC TGGGTCCTAT GTCGTCCCTG GCACTGCCCT CCAACCGCTC    1620
TACCAGGCCC TCGATCTCCC CGCTGAGATT GTGGCTCGCG CGGGCCGGCT GACCGCCACA    1680
GTAAAGGTCT CCCAGGTCGA TGGGCGGATC GATTGCGAGA CCCTTCTTGG TAACAAAACC    1740
TTTCGCACGT CGTTCGTTGA CGGGGCGGTC TTAGAGACCA ATGGCCCAGA GCGCCACAAT    1800
CTCTCCTTCG ATGCCAGTCA GAGCACTATG GCCGCTGGCC CTTTCAGTCT CACCTATGCC    1860
GCCTCTGCAG CTGGGCTGGA GGTGCGCTAT GTTGCTGCCG GCTTGACCA  TCGGGCGGTT    1920
TTTGCCCCCG GTGTTTCACC CCGGTCAGCC CCGGCGAGG  TTACCGCCTT CTGCTCTGCC    1980
CTATACAGGT TTAACCGTGA GGCCCAGCGC CATTCGCTGA TCGGTAACTT ATGGTTCCAT    2040
CCTGAGGGAC TCATTGGCCT CTTCGCCCCG TTTTCGCCCG GGCATGTTTG GGAGTCGGCT    2100
AATCCATTCT GTGGCGAGAG CACACTTTAC ACCCGTACTT GGTCGGAGGT TGATGCCGTC    2160
TCTAGTCCAG CCCGGCCTGA CTTAGGTTTT ATGTCTGAGC CTTCTATACC TAGTAGGGCC    2220
GCCACGCCTA CCCTGGCGGC CCCTCTACCC CCCCTGCAC  CGGACCCTTC CCCCCCTCCC    2280
TCTGCCCCGG CGCTTGCTGA GCCGGCTTCT GGCGCTACCG CCGGGCCCC  GGCCATAACT    2340
CACCAGACGG CCCGGCACCG CCGCCTGCTC TTCACCTACC CGGATGGCTC TAAGGTATTC    2400
GCCGGCTCGC TGTTCGAGTC GACATGCACG TGGCTCGTTA ACGCGTCTAA TGTTGACCAC    2460
CGCCCTGGCG GCGGGCTTTG CCATGCATTT TACCAAAGGT ACCCCGCCTC CTTTGATGCT    2520
GCCTCTTTTG TGATGCGCGA CGGCGCGGCC GCGTACACAC TAACCCCCCG GCCAATAATT    2580
CACGCTGTCG CCCCTGATTA TAGGTTGGAA CATAACCCAA AGAGGCTTGA GGCTGCTTAT    2640
CGGGAAACTT GCTCCGCCT  CGGCACCGCT GCATACCCGC TCCTCGGGAC CGGCATATAC    2700
CAGGTGCCGA TCGGCCCCAG TTTTGACGCC TGGGAGCGGA ACCACCGCCC CGGGGATGAG    2760
TTGTACCTTC CTGAGCTTGC TGCCAGATGG TTTGAGGCCA ATAGGCCGAC CCGCCCGACT    2820
CTCACTATAA CTGAGGATGT TGCACGGACA GCGAATCTGG CCATCGAGCT TGACTCAGCC    2880
ACAGATGTCG GCCGGGCCTG TGCCGGCTGT CGGGTCACCC CCGGCGTTGT TCAGTACCAG    2940
TTTACTGCAG GTGTGCCTGG ATCCGGCAAG TCCCGCTCTA TCACCCAAGC CGATGTGGAC    3000
GTTGTCGTGG TCCCGACGCG TGAGTTGCGT AATGCCTGGC GCCGTCGCGG CTTTGCTGCT    3060
TTTACCCCGC ATACTGCCGC CAGAGTCACC CAGGGGCGCC GGGTTGTCAT TGATGAGGCT    3120
CCATCCCTCC CCCCTCACCT GCTGCTGCTC CACATGCAGC GGGCCGCCAC CGTCCACCTT    3180
CTTGGCGACC CGAACCAGAT CCCAGCCATC GACTTTGAGC ACGCTGGGCT CGTCCCCGCC    3240
ATCAGGCCCG ACTTAGGCCC CACCTCCTGG TGGCATGTTA CCCATCGCTG GCCTGCGGAT    3300
GTATGCGAGC TCATCCGTGG TGCATACCCC ATGATCCAGA CCACTAGCCG GGTTCTCCGT    3360
TCGTTGTTCT GGGGTGAGCC TGCCGTCGGG CAGAAACTAG TGTTCACCCA GGCGGCCAAG    3420
CCCGCCAACC CCGGCTCAGT GACGGTCCAC GAGGCGCAGG GCGCTACCTA CACGGAGACC    3480
ACTATTATTG CCACAGCAGA TGCCCGGGGC CTTATTCAGT CGTCTCGGGC TCATGCCATT    3540
GTTGCTCTGA CGCGCCACAC TGAGAAGTGC GTCATCATTG ACGCACCAGG CCTGCTTCGC    3600
GAGGTGGGCA TCTCCGATGC AATCGTTAAT AACTTTTTCC TCGCTGGTGG CGAAATTGGT    3660
CACCAGCGCC CATCAGTTAT TCCCCGTGGC AACCCTGACG CCAATGTTGA CACCCTGGCT    3720
GCCTTCCCGC CGTCTTGCCA GATTAGTGCC TTCCATCAGT TGGCTGAGGA GCTTGGCCAC    3780
AGACCTGTCC CTGTTGCAGC TGTTCTACCA CCCTGCCCCG AGCTCGAACA GGGCCTTCTC    3840
```

-continued

| | | | | | |
|---|---|---|---|---|---|
|TACCTGCCCC|AGGAGCTCAC|CACCTGTGAT|AGTGTCGTAA|CATTTGAATT|AACAGACATT 3900|
|GTGCACTGCC|GCATGGCCGC|CCCGAGCCAG|CGCAAGGCCG|TGCTGTCCAC|ACTCGTGGGC 3960|
|CGCTACGGCG|GTCGCACAAA|GCTCTACAAT|GCTTCCCACT|CTGATGTTCG|CGACTCTCTC 4020|
|GCCCGTTTTA|TCCCGGCCAT|TGGCCCCGTA|CAGGTTACAA|CTTGTGAATT|GTACGAGCTA 4080|
|GTGGAGGCCA|TGGTCGAGAA|GGGCCAGGAT|GGCTCCGCCG|TCCTTGAGCT|TGATCTTTGC 4140|
|AACCGTGACG|TGTCCAGGAT|CACCTTCTTC|CAGAAAGATT|GTAACAAGTT|CACCACAGGT 4200|
|GAGACCATTG|CCCATGGTAA|AGTGGGCCAG|GGCATCTCGG|CCTGGAGCAA|GACCTTCTGC 4260|
|GCCCTCTTTG|GCCCTTGGTT|CCGCGCTATT|GAGAAGGCTA|TTCTGGCCCT|GCTCCCTCAG 4320|
|GGTGTGTTTT|ACGGTGATGC|CTTTGATGAC|ACCGTCTTCT|CGGCGGCTGT|GGCCGCAGCA 4380|
|AAGGCATCCA|TGGTGTTTGA|GAATGACTTT|TCTGAGTTTG|ACTCCACCCA|GAATAACTTT 4440|
|TCTCTGGGTC|TAGAGTGTGC|TATTATGGAG|GAGTGTGGGA|TGCCGCAGTG|GCTCATCCGC 4500|
|CTGTATCACC|TTATAAGGTC|TGCGTGGATC|TTGCAGGCCC|CGAAGGAGTC|TCTGCGAGGG 4560|
|TTTTGGAAGA|AACACTCCGG|TGAGCCCGGC|ACTCTTCTAT|GGAATACTGT|CTGGAATATG 4620|
|GCCGTTATTA|CCCACTGTTA|TGACTTCCGC|GATTTTCAGG|TGGCTGCCTT|TAAAGGTGAT 4680|
|GATTCGATAG|TGCTTTGCAG|TGAGTATCGT|CAGAGTCCAG|GAGCTGCTGT|CCTGATCGCC 4740|
|GGCTGTGGCT|TGAAGTTGAA|GGTAGATTTC|CGCCCGATCG|GTTTGTATGC|AGGTGTTGTG 4800|
|GTGGCCCCCG|GCCTTGGCGC|GCTCCCTGAT|GTTGTGCGCT|TCGCCGGCCG|GCTTACCGAG 4860|
|AAGAATTGGG|GCCCTGGCCC|TGAGCGGGCG|GAGCAGCTCC|GCCTCGCTGT|TAGTGATTTC 4920|
|CTCCGCAAGC|TCACGAATGT|AGCTCAGATG|TGTGTGGATG|TTGTTTCCCG|TGTTTATGGG 4980|
|GTTTCCCCTG|GACTCGTTCA|TAACCTGATT|GGCATGCTAC|AGGCTGTTGC|TGATGGCAAG 5040|
|GCACATTTCA|CTGAGTCAGT|AAAACCAGTG|CTCGACTTGA|CAAATTCAAT|CTTGTGTCGG 5100|
|GTGGAATGAA|TAACATGTCT|TTTGCTGCGC|CCATGGGTTC|GCGACCATGC|GCCCTCGGCC 5160|
|TATTTTGTTG|CTGCTCCTCA|TGTTTTTGCC|TATGCTGCCC|GCGCCACCGC|CCGGTCAGCC 5220|
|GTCTGGCCGC|CGTCGTGGGC|GGCGCAGCGG|CGGTTCCGGC|GGTGGTTTCT|GGGGTGACCG 5280|
|GGTTGATTCT|CAGCCCTTCG|CAATCCCCTA|TATTCATCCA|ACCAACCCCT|TCGCCCCCGA 5340|
|TGTCACCGCT|GCGGCCGGGG|CTGGACCTCG|TGTTCGCCAA|CCCGCCCGAC|CACTCGGCTC 5400|
|CGCTTGGCGT|GACCAGGCCC|AGCGCCCCGC|CGTTGCCTCA|CGTCGTAGAC|CTACCACAGC 5460|
|TGGGGCCGCG|CCGCTAACCG|CGGTCGCTCC|GGCCCATGAC|ACCCCGCCAG|TGCCTGATGT 5520|
|CGACTCCCGC|GGCGCCATCT|TGCGCCGGCA|GTATAACCTA|TCAACATCTC|CCCTTACCTC 5580|
|TTCCGTGGCC|ACCGGCACTA|ACCTGGTTCT|TTATGCCGCC|CCTCTTAGTC|CGCTTTTACC 5640|
|CCTTCAGGAC|GGCACCAATA|CCCATATAAT|GGCCACGGAA|GCTTCTAATT|ATGCCCAGTA 5700|
|CCGGGTTGCC|CGTGCCACAA|TCCGTTACCG|CCCGCTGGTC|CCCAATGCTG|TCGGCGGTTA 5760|
|CGCCATCTCC|ATCTCATTCT|GGCCACAGAC|CACCACCACC|CCGACGTCCG|TTGATATGAA 5820|
|TTCAATAACC|TCGACGGATG|TTCGTATTTT|AGTCCAGCCC|GGCATAGCCT|CTGAGCTTGT 5880|
|GATCCCAAGT|GAGCGCCTAC|ACTATCGTAA|CCAAGGCTGG|CGCTCCGTCG|AGACCTCTGG 5940|
|GGTGGCTGAG|GAGGAGGCTA|CCTCTGGTCT|TGTTATGCTT|TGCATACATG|GCTCACTCGT 6000|
|AAATTCCTAT|ACTAATACAC|CCTATACCGG|TGCCCTCGGG|CTGTTGGACT|TTGCCCTTGA 6060|
|GCTTGAGTTT|CGCAACCTTA|CCCCCGGTAA|CACCAATACG|CGGGTCTCCC|GTTATTCCAG 6120|
|CACTGCTCGC|CACCGCCTTC|GTCGCGGTGC|GGACGGGACT|GCCGAGCTCA|CCACCACGGC 6180|
|TGCTACCCGC|TTTATGAAGG|ACCTCTATTT|TACTAGTACT|AATGGTGTCG|GTGAGATCGG 6240|

```
CCGCGGGATA  GCCCTCACCC  TGTTCAACCT  TGCTGACACT  CTGCTTGGCG  GCCTGCCGAC    6300
AGAATTGATT  TCGTCGGCTG  GTGGCCAGCT  GTTCTACTCC  CGTCCCGTTG  TCTCAGCCAA    6360
TGGCGAGCCG  ACTGTTAAGT  TGTATACATC  TGTAGAGAAT  GCTCAGCAGG  ATAAGGGTAT    6420
TGCAATCCCG  CATGACATTG  ACCTCGGAGA  ATCTCGTGTG  GTTATTCAGG  ATTATGATAA    6480
CCAACATGAA  CAAGATCGGC  CGACGCCTTC  TCCAGCCCCA  TCGCGCCCTT  TCTCTGTCCT    6540
TCGAGCTAAT  GATGTGCTTT  GGCTCTCTCT  CACCGCTGCC  GAGTATGACC  AGTCCACTTA    6600
TGGCTCTTCG  ACTGGCCCAG  TTTATGTTTC  TGACTCTGTG  ACCTTGGTTA  ATGTTGCGAC    6660
CGGCGCGCAG  GCCGTTGCCC  GGTCGCTCGA  TTGGACCAAG  GTCACACTTG  ACGGTCGCCC    6720
CCTCTCCACC  ATCCAGCAGT  ACTCGAAGAC  CTTCTTTGTC  CTGCCGCTCC  GCGGTAAGCT    6780
CTCTTTCTGG  GAGGCAGGCA  CAACTAAAGC  CGGGTACCCT  TATAATTATA  ACACCACTGC    6840
TAGCGACCAA  CTGCTTGTCG  AGAATGCCGC  CGGGCACCGG  GTCGCTATTT  CCACTTACAC    6900
CACTAGCCTG  GGTGCTGGTC  CCGTCTCCAT  TTCTGCGGTT  GCCGTTTTAG  CCCCCCACTC    6960
TGCGCTAGCA  TTGCTTGAGG  ATACCTTGGA  CTACCCTGCC  CGCGCCCATA  CTTTTGATGA    7020
TTTCTGCCCA  GAGTGCCGCC  CCCTTGGCCT  TCAGGGCTGC  GCTTTCCAGT  CTACTGTCGC    7080
TGAGCTTCAG  CGCCTTAAGA  TGAAGGTGGG  TAAAACTCGG  GAGTTGTAGT  TTATTTGCTT    7140
GTGCCCCCCT  TCTTTCTGTT  GCTTATTTCT  CATTTCTGCG  TTCCGCGCTC  CCTGA         7195
```

( 2 ) INFORMATION FOR SEQ ID NO:7:

( i ) SEQUENCE CHARACTERISTICS:
    ( A ) LENGTH: 1693 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

```
Met Glu Ala His Gln Phe Ile Lys Ala Pro Gly Ile Thr Thr Ala Ile
 1               5                  10                  15

Glu Gln Ala Ala Leu Ala Ala Ala Asn Ser Ala Leu Ala Asn Ala Val
            20                  25                  30

Val Val Arg Pro Phe Leu Ser His Gln Ile Glu Ile Leu Ile Asn
        35                  40                  45

Leu Met Gln Pro Arg Gln Leu Val Phe Arg Pro Glu Val Phe Trp Asn
    50                  55                  60

His Pro Ile Gln Arg Val Ile His Asn Glu Leu Glu Leu Tyr Cys Arg
65                  70                  75                  80

Ala Arg Ser Gly Arg Cys Leu Glu Ile Gly Ala His Pro Arg Ser Ile
                85                  90                  95

Asn Asp Asn Pro Asn Val Val His Arg Cys Phe Leu Arg Pro Val Gly
            100                 105                 110

Arg Asp Val Gln Arg Trp Tyr Thr Ala Pro Thr Arg Gly Pro Ala Ala
        115                 120                 125

Asn Cys Arg Arg Ser Ala Leu Arg Gly Leu Pro Ala Ala Asp Arg Thr
    130                 135                 140

Tyr Cys Leu Asp Gly Phe Ser Gly Cys Asn Phe Pro Ala Glu Thr Gly
145                 150                 155                 160

Ile Ala Leu Tyr Ser Leu His Asp Met Ser Pro Ser Asp Val Ala Glu
                165                 170                 175

Ala Met Phe Arg His Gly Met Thr Arg Leu Tyr Ala Ala Leu His Leu
            180                 185                 190
```

| | | | | | | | | | | | | | | |
|---|---|---|---|---|---|---|---|---|---|---|---|---|---|---|
| Pro | Pro | Glu 195 | Val | Leu | Leu | Pro 200 | Pro | Gly | Thr | Tyr | Arg 205 | Thr | Ala | Ser | Tyr |
| Leu | Leu 210 | Ile | His | Asp | Gly | Arg 215 | Val | Val | Val | Thr 220 | Tyr | Glu | Gly | Asp |
| Thr 225 | Ser | Ala | Gly | Tyr | Asn 230 | His | Asp | Val | Ser | Asn 235 | Leu | Arg | Ser | Trp | Ile 240 |
| Arg | Thr | Thr | Lys | Val 245 | Thr | Gly | Asp | His | Pro 250 | Leu | Val | Ile | Glu | Arg 255 | Val |
| Arg | Ala | Ile | Gly 260 | Cys | His | Phe | Val | Leu 265 | Leu | Thr | Ala | Ala 270 | Pro | Glu |
| Pro | Ser | Pro 275 | Met | Pro | Tyr | Val | Pro 280 | Tyr | Pro | Arg | Ser | Thr 285 | Glu | Val | Tyr |
| Val | Arg 290 | Ser | Ile | Phe | Gly | Pro 295 | Gly | Gly | Thr | Pro | Ser 300 | Leu | Phe | Pro | Thr |
| Ser 305 | Cys | Ser | Thr | Lys | Ser 310 | Thr | Phe | His | Ala | Val 315 | Pro | Ala | His | Ile | Trp 320 |
| Asp | Arg | Leu | Met | Leu 325 | Phe | Gly | Ala | Thr | Leu 330 | Asp | Asp | Gln | Ala | Phe 335 | Cys |
| Cys | Ser | Arg | Leu 340 | Met | Thr | Tyr | Leu | Arg 345 | Gly | Ile | Ser | Tyr | Lys 350 | Val | Thr |
| Val | Gly | Thr 355 | Leu | Val | Ala | Asn | Glu 360 | Gly | Trp | Asn | Ala | Ser 365 | Glu | Asp | Ala |
| Leu | Thr 370 | Ala | Val | Ile | Thr | Ala 375 | Ala | Tyr | Leu | Thr | Ile 380 | Cys | His | Gln | Arg |
| Tyr 385 | Leu | Arg | Thr | Gln | Ala 390 | Ile | Ser | Lys | Gly | Met 395 | Arg | Arg | Leu | Glu | Arg 400 |
| Glu | His | Ala | Gln | Lys 405 | Phe | Ile | Thr | Arg | Leu 410 | Tyr | Ser | Trp | Leu | Phe 415 | Glu |
| Lys | Ser | Gly | Arg 420 | Asp | Tyr | Ile | Pro | Gly 425 | Arg | Gln | Leu | Glu | Phe 430 | Tyr | Ala |
| Gln | Cys | Arg 435 | Arg | Trp | Leu | Ser | Ala 440 | Gly | Phe | His | Leu | Asp 445 | Pro | Arg | Val |
| Leu | Val 450 | Phe | Asp | Glu | Ser | Ala 455 | Pro | Cys | His | Cys | Arg 460 | Thr | Ala | Ile | Arg |
| Lys 465 | Ala | Leu | Ser | Lys | Phe 470 | Cys | Cys | Phe | Met | Lys 475 | Trp | Leu | Gly | Gln | Glu 480 |
| Cys | Thr | Cys | Phe | Leu 485 | Gln | Pro | Ala | Glu | Gly 490 | Ala | Val | Gly | Asp | Gln 495 | Gly |
| His | Asp | Asn | Glu 500 | Ala | Tyr | Glu | Gly | Ser 505 | Asp | Val | Asp | Pro | Ala 510 | Glu | Ser |
| Ala | Ile | Ser 515 | Asp | Ile | Ser | Gly | Ser 520 | Tyr | Val | Val | Pro | Gly 525 | Thr | Ala | Leu |
| Gln | Pro 530 | Leu | Tyr | Gln | Ala | Leu 535 | Asp | Leu | Pro | Ala | Glu 540 | Ile | Val | Ala | Arg |
| Ala 545 | Gly | Arg | Leu | Thr | Ala 550 | Thr | Val | Lys | Val | Ser 555 | Gln | Val | Asp | Gly 560 | Arg |
| Ile | Asp | Cys | Glu | Thr 565 | Leu | Leu | Gly | Asn | Lys 570 | Thr | Phe | Arg | Thr | Ser 575 | Phe |
| Val | Asp | Gly | Ala 580 | Val | Leu | Glu | Thr | Asn 585 | Gly | Pro | Glu | Arg | His 590 | Asn | Leu |
| Ser | Phe | Asp 595 | Ala | Ser | Gln | Ser | Thr 600 | Met | Ala | Ala | Gly | Pro 605 | Phe | Ser | Leu |
| Thr | Tyr 610 | Ala | Ala | Ser | Ala | Ala 615 | Gly | Leu | Glu | Val | Arg 620 | Tyr | Val | Ala | Ala |

| | | | | | | | | | | | | | | | |
|---|---|---|---|---|---|---|---|---|---|---|---|---|---|---|---|
| Gly | Leu | Asp | His | Arg | Ala | Val | Phe | Ala | Pro | Gly | Val | Ser | Pro | Arg | Ser |
| 625 | | | | 630 | | | | | 635 | | | | | | 640 |
| Ala | Pro | Gly | Glu | Val | Thr | Ala | Phe | Cys | Ser | Ala | Leu | Tyr | Arg | Phe | Asn |
| | | | | 645 | | | | 650 | | | | | | 655 | |
| Arg | Glu | Ala | Gln | Arg | His | Ser | Leu | Ile | Gly | Asn | Leu | Trp | Phe | His | Pro |
| | | | 660 | | | | | 665 | | | | | 670 | | |
| Glu | Gly | Leu | Ile | Gly | Leu | Phe | Ala | Pro | Phe | Ser | Pro | Gly | His | Val | Trp |
| | | | 675 | | | | 680 | | | | | 685 | | | |
| Glu | Ser | Ala | Asn | Pro | Phe | Cys | Gly | Glu | Ser | Thr | Leu | Tyr | Thr | Arg | Thr |
| | 690 | | | | | 695 | | | | | 700 | | | | |
| Trp | Ser | Glu | Val | Asp | Ala | Val | Ser | Ser | Pro | Ala | Arg | Pro | Asp | Leu | Gly |
| 705 | | | | 710 | | | | | 715 | | | | | | 720 |
| Phe | Met | Ser | Glu | Pro | Ser | Ile | Pro | Ser | Arg | Ala | Ala | Thr | Pro | Thr | Leu |
| | | | | 725 | | | | | 730 | | | | | 735 | |
| Ala | Ala | Pro | Leu | Pro | Pro | Pro | Ala | Pro | Asp | Pro | Ser | Pro | Pro | Pro | Ser |
| | | | 740 | | | | | 745 | | | | | 750 | | |
| Ala | Pro | Ala | Leu | Ala | Glu | Pro | Ala | Ser | Gly | Ala | Thr | Ala | Gly | Ala | Pro |
| | | 755 | | | | | 760 | | | | | 765 | | | |
| Ala | Ile | Thr | His | Gln | Thr | Ala | Arg | His | Arg | Arg | Leu | Leu | Phe | Thr | Tyr |
| | 770 | | | | | 775 | | | | | 780 | | | | |
| Pro | Asp | Gly | Ser | Lys | Val | Phe | Ala | Gly | Ser | Leu | Phe | Glu | Ser | Thr | Cys |
| 785 | | | | | 790 | | | | | 795 | | | | | 800 |
| Thr | Trp | Leu | Val | Asn | Ala | Ser | Asn | Val | Asp | His | Arg | Pro | Gly | Gly | Gly |
| | | | | 805 | | | | | 810 | | | | | 815 | |
| Leu | Cys | His | Ala | Phe | Tyr | Gln | Arg | Tyr | Pro | Ala | Ser | Phe | Asp | Ala | Ala |
| | | | 820 | | | | | 825 | | | | | 830 | | |
| Ser | Phe | Val | Met | Arg | Asp | Gly | Ala | Ala | Ala | Tyr | Thr | Leu | Thr | Pro | Arg |
| | | 835 | | | | | 840 | | | | | 845 | | | |
| Pro | Ile | Ile | His | Ala | Val | Ala | Pro | Asp | Tyr | Arg | Leu | Glu | His | Asn | Pro |
| | 850 | | | | | 855 | | | | | 860 | | | | |
| Lys | Arg | Leu | Glu | Ala | Ala | Tyr | Arg | Glu | Thr | Cys | Ser | Arg | Leu | Gly | Thr |
| 865 | | | | | 870 | | | | | 875 | | | | | 880 |
| Ala | Ala | Tyr | Pro | Leu | Leu | Gly | Thr | Gly | Ile | Tyr | Gln | Val | Pro | Ile | Gly |
| | | | | 885 | | | | | 890 | | | | | 895 | |
| Pro | Ser | Phe | Asp | Ala | Trp | Glu | Arg | Asn | His | Arg | Pro | Gly | Asp | Glu | Leu |
| | | | 900 | | | | | 905 | | | | | 910 | | |
| Tyr | Leu | Pro | Glu | Leu | Ala | Ala | Arg | Trp | Phe | Glu | Ala | Asn | Arg | Pro | Thr |
| | | 915 | | | | | 920 | | | | | 925 | | | |
| Arg | Pro | Thr | Leu | Thr | Ile | Thr | Glu | Asp | Val | Ala | Arg | Thr | Ala | Asn | Leu |
| | 930 | | | | | 935 | | | | | 940 | | | | |
| Ala | Ile | Glu | Leu | Asp | Ser | Ala | Thr | Asp | Val | Gly | Arg | Ala | Cys | Ala | Gly |
| 945 | | | | | 950 | | | | | 955 | | | | | 960 |
| Cys | Arg | Val | Thr | Pro | Gly | Val | Val | Gln | Tyr | Gln | Phe | Thr | Ala | Gly | Val |
| | | | | 965 | | | | | 970 | | | | | 975 | |
| Pro | Gly | Ser | Gly | Lys | Ser | Arg | Ser | Ile | Thr | Gln | Ala | Asp | Val | Asp | Val |
| | | | 980 | | | | | 985 | | | | | 990 | | |
| Val | Val | Val | Pro | Thr | Arg | Glu | Leu | Arg | Asn | Ala | Trp | Arg | Arg | Arg | Gly |
| | | 995 | | | | | 1000 | | | | | 1005 | | | |
| Phe | Ala | Ala | Phe | Thr | Pro | His | Thr | Ala | Ala | Arg | Val | Thr | Gln | Gly | Arg |
| | | 1010 | | | | 1015 | | | | | 1020 | | | | |
| Arg | Val | Val | Ile | Asp | Glu | Ala | Pro | Ser | Leu | Pro | Pro | His | Leu | Leu | Leu |
| 1025 | | | | | 1030 | | | | | 1035 | | | | | 1040 |

-continued

Leu His Met Gln Arg Ala Ala Thr Val His Leu Leu Gly Asp Pro Asn
             1045                1050                1055

Gln Ile Pro Ala Ile Asp Phe Glu His Ala Gly Leu Val Pro Ala Ile
        1060                1065                1070

Arg Pro Asp Leu Gly Pro Thr Ser Trp Trp His Val Thr His Arg Trp
        1075                1080                1085

Pro Ala Asp Val Cys Glu Leu Ile Arg Gly Ala Tyr Pro Met Ile Gln
        1090                1095                1100

Thr Thr Ser Arg Val Leu Arg Ser Leu Phe Trp Gly Glu Pro Ala Val
1105             1110                1115                1120

Gly Gln Lys Leu Val Phe Thr Gln Ala Ala Lys Pro Ala Asn Pro Gly
                1125                1130                1135

Ser Val Thr Val His Glu Ala Gln Gly Ala Thr Tyr Thr Glu Thr Thr
             1140                1145                1150

Ile Ile Ala Thr Ala Asp Ala Arg Gly Leu Ile Gln Ser Ser Arg Ala
        1155                1160                1165

His Ala Ile Val Ala Leu Thr Arg His Thr Glu Lys Cys Val Ile Ile
             1170                1175                1180

Asp Ala Pro Gly Leu Leu Arg Glu Val Gly Ile Ser Asp Ala Ile Val
1185             1190                1195                1200

Asn Asn Phe Phe Leu Ala Gly Gly Glu Ile Gly His Gln Arg Pro Ser
                1205                1210                1215

Val Ile Pro Arg Gly Asn Pro Asp Ala Asn Val Asp Thr Leu Ala Ala
             1220                1225                1230

Phe Pro Pro Ser Cys Gln Ile Ser Ala Phe His Gln Leu Ala Glu Glu
        1235                1240                1245

Leu Gly His Arg Pro Val Pro Val Ala Ala Val Leu Pro Pro Cys Pro
        1250                1255                1260

Glu Leu Glu Gln Gly Leu Leu Tyr Leu Pro Gln Glu Leu Thr Thr Cys
1265             1270                1275                1280

Asp Ser Val Val Thr Phe Glu Leu Thr Asp Ile Val His Cys Arg Met
                1285                1290                1295

Ala Ala Pro Ser Gln Arg Lys Ala Val Leu Ser Thr Leu Val Gly Arg
        1300                1305                1310

Tyr Gly Gly Arg Thr Lys Leu Tyr Asn Ala Ser His Ser Asp Val Arg
        1315                1320                1325

Asp Ser Leu Ala Arg Phe Ile Pro Ala Ile Gly Pro Val Gln Val Thr
        1330                1335                1340

Thr Cys Glu Leu Tyr Glu Leu Val Glu Ala Met Val Glu Lys Gly Gln
1345             1350                1355                1360

Asp Gly Ser Ala Val Leu Glu Leu Asp Leu Cys Asn Arg Asp Val Ser
                1365                1370                1375

Arg Ile Thr Phe Phe Gln Lys Asp Cys Asn Lys Phe Thr Thr Gly Glu
        1380                1385                1390

Thr Ile Ala His Gly Lys Val Gly Gln Gly Ile Ser Ala Trp Ser Lys
        1395                1400                1405

Thr Phe Cys Ala Leu Phe Gly Pro Trp Phe Arg Ala Ile Glu Lys Ala
        1410                1415                1420

Ile Leu Ala Leu Leu Pro Gln Gly Val Phe Tyr Gly Asp Ala Phe Asp
1425             1430                1435                1440

Asp Thr Val Phe Ser Ala Ala Val Ala Ala Ala Lys Ala Ser Met Val
                1445                1450                1455

Phe Glu Asn Asp Phe Ser Glu Phe Asp Ser Thr Gln Asn Asn Phe Ser
                1460                1465                1470

Leu Gly Leu Glu Cys Ala Ile Met Glu Glu Cys Gly Met Pro Gln Trp
         1475                1480                1485

Leu Ile Arg Leu Tyr His Leu Ile Arg Ser Ala Trp Ile Leu Gln Ala
         1490                1495                1500

Pro Lys Glu Ser Leu Arg Gly Phe Trp Lys Lys His Ser Gly Glu Pro
1505                1510                1515                1520

Gly Thr Leu Leu Trp Asn Thr Val Trp Asn Met Ala Val Ile Thr His
                 1525                1530                1535

Cys Tyr Asp Phe Arg Asp Phe Gln Val Ala Ala Phe Lys Gly Asp Asp
             1540                1545                1550

Ser Ile Val Leu Cys Ser Glu Tyr Arg Gln Ser Pro Gly Ala Ala Val
         1555                1560                1565

Leu Ile Ala Gly Cys Gly Leu Lys Leu Lys Val Asp Phe Arg Pro Ile
         1570                1575                1580

Gly Leu Tyr Ala Gly Val Val Val Ala Pro Gly Leu Gly Ala Leu Pro
1585                1590                1595                1600

Asp Val Val Arg Phe Ala Gly Arg Leu Thr Glu Lys Asn Trp Gly Pro
                 1605                1610                1615

Gly Pro Glu Arg Ala Glu Gln Leu Arg Leu Ala Val Ser Asp Phe Leu
             1620                1625                1630

Arg Lys Leu Thr Asn Val Ala Gln Met Cys Val Asp Val Val Ser Arg
         1635                1640                1645

Val Tyr Gly Val Ser Pro Gly Leu Val His Asn Leu Ile Gly Met Leu
         1650                1655                1660

Gln Ala Val Ala Asp Gly Lys Ala His Phe Thr Glu Ser Val Lys Pro
1665                1670                1675                1680

Val Leu Asp Leu Thr Asn Ser Ile Leu Cys Arg Val Glu
                 1685                1690

( 2 ) INFORMATION FOR SEQ ID NO:8:

( i ) SEQUENCE CHARACTERISTICS:
        ( A ) LENGTH: 660 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

Met Arg Pro Arg Pro Ile Leu Leu Leu Leu Met Phe Leu Pro Met
1               5                   10                  15

Leu Pro Ala Pro Pro Pro Gly Gln Pro Ser Gly Arg Arg Arg Gly Arg
             20                  25                  30

Arg Ser Gly Gly Ser Gly Gly Gly Phe Trp Gly Asp Arg Val Asp Ser
         35                  40                  45

Gln Pro Phe Ala Ile Pro Tyr Ile His Pro Thr Asn Pro Phe Ala Pro
     50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Val
             85                  90                  95

Ala Ser Arg Arg Arg Pro Thr Thr Ala Gly Ala Ala Pro Leu Thr Ala
         100                 105                 110

Val Ala Pro Ala His Asp Thr Pro Pro Val Pro Asp Val Asp Ser Arg
         115                 120                 125

```
Gly Ala Ile Leu Arg Arg Gln Tyr Asn Leu Ser Thr Ser Pro Leu Thr
    130             135             140

Ser Ser Val Ala Thr Gly Thr Asn Leu Val Leu Tyr Ala Ala Pro Leu
145             150             155                     160

Ser Pro Leu Leu Pro Leu Gln Asp Gly Thr Asn Thr His Ile Met Ala
                165             170             175

Thr Glu Ala Ser Asn Tyr Ala Gln Tyr Arg Val Ala Arg Ala Thr Ile
            180             185             190

Arg Tyr Arg Pro Leu Val Pro Asn Ala Val Gly Gly Tyr Ala Ile Ser
        195             200             205

Ile Ser Phe Trp Pro Gln Thr Thr Thr Pro Thr Ser Val Asp Met
    210             215             220

Asn Ser Ile Thr Ser Thr Asp Val Arg Ile Leu Val Gln Pro Gly Ile
225             230             235                     240

Ala Ser Glu Leu Val Ile Pro Ser Glu Arg Leu His Tyr Arg Asn Gln
            245             250             255

Gly Trp Arg Ser Val Glu Thr Ser Gly Val Ala Glu Glu Ala Thr
        260             265             270

Ser Gly Leu Val Met Leu Cys Ile His Gly Ser Leu Val Asn Ser Tyr
    275             280             285

Thr Asn Thr Pro Tyr Thr Gly Ala Leu Gly Leu Leu Asp Phe Ala Leu
    290             295             300

Glu Leu Glu Phe Arg Asn Leu Thr Pro Gly Asn Thr Asn Thr Arg Val
305             310             315             320

Ser Arg Tyr Ser Ser Thr Ala Arg His Arg Leu Arg Arg Gly Ala Asp
            325             330             335

Gly Thr Ala Glu Leu Thr Thr Thr Ala Ala Thr Arg Phe Met Lys Asp
            340             345             350

Leu Tyr Phe Thr Ser Thr Asn Gly Val Gly Glu Ile Gly Arg Gly Ile
        355             360             365

Ala Leu Thr Leu Phe Asn Leu Ala Asp Thr Leu Leu Gly Gly Leu Pro
        370             375             380

Thr Glu Leu Ile Ser Ser Ala Gly Gly Gln Leu Phe Tyr Ser Arg Pro
385             390             395             400

Val Val Ser Ala Asn Gly Glu Pro Thr Val Lys Leu Tyr Thr Ser Val
            405             410             415

Glu Asn Ala Gln Gln Asp Lys Gly Ile Ala Ile Pro His Asp Ile Asp
            420             425             430

Leu Gly Glu Ser Arg Val Val Ile Gln Asp Tyr Asp Asn Gln His Glu
        435             440             445

Gln Asp Arg Pro Thr Pro Ser Pro Ala Pro Ser Arg Pro Phe Ser Val
    450             455             460

Leu Arg Ala Asn Asp Val Leu Trp Leu Ser Leu Thr Ala Ala Glu Tyr
465             470             475             480

Asp Gln Ser Thr Tyr Gly Ser Ser Thr Gly Pro Val Tyr Val Ser Asp
            485             490             495

Ser Val Thr Leu Val Asn Val Ala Thr Gly Ala Gln Ala Val Ala Arg
            500             505             510

Ser Leu Asp Trp Thr Lys Val Thr Leu Asp Gly Arg Pro Leu Ser Thr
        515             520             525

Ile Gln Gln Tyr Ser Lys Thr Phe Phe Val Leu Pro Leu Arg Gly Lys
    530             535             540

Leu Ser Phe Trp Glu Ala Gly Thr Thr Lys Ala Gly Tyr Pro Tyr Asn
545             550             555             560
```

| | | | | | | | | | | | | | | |
|---|---|---|---|---|---|---|---|---|---|---|---|---|---|---|
| Tyr | Asn | Thr | Thr | Ala 565 | Ser | Asp | Gln | Leu | Leu 570 | Val | Glu | Asn | Ala | Ala 575 | Gly |
| His | Arg | Val | Ala 580 | Ile | Ser | Thr | Tyr | Thr 585 | Thr | Ser | Leu | Gly | Ala 590 | Gly | Pro |
| Val | Ser | Ile 595 | Ser | Ala | Val | Ala | Val 600 | Leu | Ala | Pro | His | Ser 605 | Ala | Leu | Ala |
| Leu | Leu 610 | Glu | Asp | Thr | Leu | Asp 615 | Tyr | Pro | Ala | Arg | Ala 620 | His | Thr | Phe | Asp |
| Asp 625 | Phe | Cys | Pro | Glu | Cys 630 | Arg | Pro | Leu | Gly | Leu 635 | Gln | Gly | Cys | Ala | Phe 640 |
| Gln | Ser | Thr | Val | Ala 645 | Glu | Leu | Gln | Arg | Leu 650 | Lys | Met | Lys | Val | Gly 655 | Lys |
| Thr | Arg | Glu | Leu 660 | | | | | | | | | | | | |

(2) INFORMATION FOR SEQ ID NO:9:

(i) SEQUENCE CHARACTERISTICS:
        (A) LENGTH: 123 amino acids
        (B) TYPE: amino acid
        (D) TOPOLOGY: linear (ii) MOLECULE TYPE: protein (xi) SEQUENCE DESCRIPTION: SEQ ID NO:9:

| | | | | | | | | | | | | | | |
|---|---|---|---|---|---|---|---|---|---|---|---|---|---|---|
| Met 1 | Asn | Asn | Met | Ser 5 | Phe | Ala | Ala | Pro | Met 10 | Gly | Ser | Arg | Pro | Cys 15 | Ala |
| Leu | Gly | Leu | Phe 20 | Cys | Cys | Cys | Ser | Ser 25 | Cys | Phe | Cys | Leu | Cys 30 | Cys | Pro |
| Arg | His | Arg 35 | Pro | Val | Ser | Arg | Leu 40 | Ala | Ala | Val | Val | Gly 45 | Gly | Ala | Ala |
| Ala | Val 50 | Pro | Ala | Val | Val | Ser 55 | Gly | Val | Thr | Gly | Leu 60 | Ile | Leu | Ser | Pro |
| Ser 65 | Gln | Ser | Pro | Ile | Phe 70 | Ile | Gln | Pro | Thr | Pro 75 | Ser | Pro | Pro | Met | Ser 80 |
| Pro | Leu | Arg | Pro | Gly 85 | Leu | Asp | Leu | Val | Phe 90 | Ala | Asn | Pro | Pro | Asp 95 | His |
| Ser | Ala | Pro | Leu 100 | Gly | Val | Thr | Arg | Pro 105 | Ser | Ala | Pro | Pro | Leu 110 | Pro | His |
| Val | Val | Asp 115 | Leu | Pro | Gln | Leu | Gly 120 | Pro | Arg | Arg | | | | | |

(2) INFORMATION FOR SEQ ID NO:10:

(i) SEQUENCE CHARACTERISTICS:
        (A) LENGTH: 7171 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Composite Mexico strain (xi) SEQUENCE DESCRIPTION: SEQ ID NO:10:

```
GCCATGGAGG CCCACCAGTT CATTAAGGCT CCTGGCATCA CTACTGCTAT TGAGCAAGCA        60
```

-continued

| | | | | | |
|---|---|---|---|---|---|
| GCTCTAGCAG | CGGCCAACTC | CGCCCTTGCG | AATGCTGTGG | TGGTCCGGCC | TTTCCTTTCC | 120 |
| CATCAGCAGG | TTGAGATCCT | TATAAATCTC | ATGCAACCTC | GGCAGCTGGT | GTTTCGTCCT | 180 |
| GAGGTTTTTT | GGAATCACCC | GATTCAACGT | GTTATACATA | ATGAGCTTGA | GCAGTATTGC | 240 |
| CGTGCTCGCT | CGGGTCGCTG | CCTTGAGATT | GGAGCCCACC | CACGCTCCAT | TAATGATAAT | 300 |
| CCTAATGTCC | TCCATCGCTG | CTTTCTCCAC | CCCGTCGGCC | GGGATGTTCA | GCGCTGGTAC | 360 |
| ACAGCCCCGA | CTAGGGACC | TGCGGCGAAC | TGTCGCCGCT | CGGCACTTCG | TGGTCTGCCA | 420 |
| CCAGCCGACC | GCACTTACTG | TTTTGATGGC | TTTGCCGGCT | GCCGTTTTGC | CGCCGAGACT | 480 |
| GGTGTGGCTC | TCTATTCTCT | CCATGACTTG | CAGCCGGCTG | ATGTTGCCGA | GGCGATGGCT | 540 |
| CGCCACGGCA | TGACCCGCCT | TTATGCAGCT | TTCCACTTGC | CTCCAGAGGT | GCTCCTGCCT | 600 |
| CCTGGCACCT | ACCGGACATC | ATCCTACTTG | CTGATCCACG | ATGGTAAGCG | CGCGGTTGTC | 660 |
| ACTTATGAGG | GTGACACTAG | CGCCGGTTAC | AATCATGATG | TTGCCACCCT | CCGCACATGG | 720 |
| ATCAGGACAA | CTAAGGTTGT | GGGTGAACAC | CCTTTGGTGA | TCGAGCGGGT | GCGGGGTATT | 780 |
| GGCTGTCACT | TTGTGTTGTT | GATCACTGCG | GCCCTGAGC | CCTCCCCGAT | GCCCTACGTT | 840 |
| CCTTACCCGC | GTTCGACGGA | GGTCTATGTC | CGGTCTATCT | TTGGGCCCGG | CGGGTCCCCG | 900 |
| TCGCTGTTCC | CGACCGCTTG | TGCTGTCAAG | TCCACTTTTC | ACGCCGTCCC | CACGCACATC | 960 |
| TGGGACCGTC | TCATGCTCTT | TGGGGCCACC | CTCGACGACC | AGGCCTTTTG | CTGCTCCAGG | 1020 |
| CTTATGACGT | ACCTTCGTGG | CATTAGCTAT | AAGGTAACTG | TGGGTGCCCT | GGTCGCTAAT | 1080 |
| GAAGGCTGGA | ATGCCACCGA | GGATGCGCTC | ACTGCAGTTA | TTACGGCGGC | TTACCTCACA | 1140 |
| ATATGTCATC | AGCGTTATTT | GCGGACCCAG | GCGATTTCTA | AGGGCATGCG | CCGGCTTGAG | 1200 |
| CTTGAACATG | CTCAGAAATT | TATTTCACGC | CTCTACAGCT | GGCTATTTGA | GAAGTCAGGT | 1260 |
| CGTGATTACA | TCCCAGGCCG | CCAGCTGCAG | TTCTACGCTC | AGTGCCGCCG | CTGGTTATCT | 1320 |
| GCCGGGTTCC | ATCTCGACCC | CCGCACCTTA | GTTTTGATG | AGTCAGTGCC | TTGTAGCTGC | 1380 |
| CGAACCACCA | TCCGGCGGAT | CGCTGGAAAA | TTTTGCTGTT | TTATGAAGTG | GCTCGGTCAG | 1440 |
| GAGTGTTCTT | GTTTCCTCCA | GCCCGCCGAG | GGGCTGGCGG | GCGACCAAGG | TCATGACAAT | 1500 |
| GAGGCCTATG | AAGGCTCTGA | TGTTGATACT | GCTGAGCCTG | CCACCCTAGA | CATTACAGGC | 1560 |
| TCATACATCG | TGGATGGTCG | GTCTCTGCAA | ACTGTCTATC | AAGCTCTCGA | CCTGCCAGCT | 1620 |
| GACCTGGTAG | CTCGCGCAGC | CCGACTGTCT | GCTACAGTTA | CTGTTACTGA | AACCTCTGGC | 1680 |
| CGTCTGGATT | GCCAAACAAT | GATCGGCAAT | AAGACTTTTC | TCACTACCTT | TGTTGATGGG | 1740 |
| GCACGCCTTG | AGGTTAACGG | GCCTGAGCAG | CTTAACCTCT | CTTTTGACAG | CCAGCAGTGT | 1800 |
| AGTATGGCAG | CCGGCCCGTT | TTGCCTCACC | TATGCTGCCG | TAGATGGCGG | GCTGGAAGTT | 1860 |
| CATTTTTCCA | CCGCTGGCCT | CGAGAGCCGT | GTTGTTTTCC | CCCTGGTAA | TGCCCCGACT | 1920 |
| GCCCCGCCGA | GTGAGGTCAC | CGCCTTCTGC | TCAGCTCTTT | ATAGGCACAA | CCGGCAGAGC | 1980 |
| CAGCGCCAGT | CGGTTATTGG | TAGTTTGTGG | CTGCACCCTG | AAGGTTTGCT | CGGCCTGTTC | 2040 |
| CCGCCCTTTT | CACCCGGGCA | TGAGTGGCGG | TCTGCTAACC | CATTTGCGG | CGAGAGCACG | 2100 |
| CTCTACACCC | GCACTTGGTC | CACAATTACA | GACACACCCT | TAACTGTCGG | GCTAATTTCC | 2160 |
| GGTCATTTGG | ATGCTGCTCC | CCACTCGGGG | GGGCCACCTG | CTACTGCCAC | AGGCCCTGCT | 2220 |
| GTAGGCTCGT | CTGACTCTCC | AGACCCTGAC | CCGCTACCTG | ATGTTACAGA | TGGCTCACGC | 2280 |
| CCCTCTGGGG | CCCGTCCGGC | TGGCCCCAAC | CCGAATGGCG | TTCCGCAGCG | CCGCTTACTA | 2340 |
| CACACCTACC | CTGACGGCGC | TAAGATCTAT | GTCGGCTCCA | TTTTCGAGTC | TGAGTGCACC | 2400 |
| TGGCTTGTCA | ACGCATCTAA | CGCCGGCCAC | CGCCCTGGTG | GCGGGCTTTG | TCATGCTTTT | 2460 |

```
TTTCAGCGTT ACCCTGATTC GTTTGACGCC ACCAAGTTTG TGATGCGTGA TGGTCTTGCC      2520
GCGTATACCC TTACACCCCG GCCGATCATT CATGCGGTGG CCCCGGACTA TCGATTGGAA      2580
CATAACCCCA AGAGGCTCGA GGCTGCCTAC CGCGAGACTT GCGCCCGCCG AGGCACTGCT      2640
GCCTATCCAC TCTTAGGCGC TGGCATTTAC CAGGTGCCTG TTAGTTGAG  TTTTGATGCC      2700
TGGGAGCGGA ACCACCGCCC GTTTGACGAG CTTTACCTAA CAGAGCTGGC GGCTCGGTGG      2760
TTTGAATCCA ACCGCCCCGG TCAGCCCACG TTGAACATAA CTGAGGATAC CGCCCGTGCG      2820
GCCAACCTGG CCCTGGAGCT TGACTCCGGG AGTGAAGTAG GCCGCGCATG TGCCGGGTGT      2880
AAAGTCGAGC CTGGCGTTGT GCGGTATCAG TTTACAGCCG GTGTCCCCGG CTCTGGCAAG      2940
TCAAAGTCCG TGCAACAGGC GGATGTGGAT GTTGTTGTTG TGCCCACTCG CGAGCTTCGG      3000
AACGCTTGGC GGCGCCGGGG CTTTGCGGCA TTCACTCCGC ACACTGCGGC CCGTGTCACT      3060
AGCGGCCGTA GGGTTGTCAT TGATGAGGCC CCTTCGCTCC CCCCACACTT GCTGCTTTTA      3120
CATATGCAGC GTGCTGCATC TGTGCACCTC CTTGGGGACC CGAATCAGAT CCCCGCCATA      3180
GATTTGAGC  ACACCGGTCT GATTCCAGCA ATACGGCCGG AGTTGGTCCC GACTTCATGG      3240
TGGCATGTCA CCCACCGTTG CCCTGCAGAT GTCTGTGAGT TAGTCCGTGG TGCTTACCCT      3300
AAAATCCAGA CTACAAGTAA GGTGCTCCGT TCCCTTTTCT GGGGAGAGCC AGCTGTCGGC      3360
CAGAAGCTAG TGTTCACACA GGCTGCTAAG GCCGCGCACC CCGGATCTAT AACGGTCCAT      3420
GAGGCCCAGG GTGCCACTTT TACCACTACA ACTATAATTG CAACTGCAGA TGCCCGTGGC      3480
CTCATACAGT CCTCCCGGGC TCACGCTATA GTTGCTCTCA CTAGGCATAC TGAAAAATGT      3540
GTTATACTTG ACTCTCCCGG CCTGTTGCGT GAGGTGGGTA TCTCAGATGC CATTGTTAAT      3600
AATTTCTTCC TTTCGGGTGG CGAGGTTGGT CACCAGAGAC CATCGGTCAT TCCGCGAGGC      3660
AACCTGACC  GCAATGTTGA CGTGCTTGCG GCGTTTCCAC CTTCATGCCA AATAAGCGCC      3720
TTCCATCAGC TTGCTGAGGA GCTGGGCCAC CGGCCGGCGC GGTGGCGGC  TGTGCTACCT      3780
CCCTGCCCTG AGCTTGAGCA GGGCCTTCTC TATCTGCCAC AGGAGCTAGC CTCCTGTGAC      3840
AGTGTTGTGA CATTTGAGCT AACTGACATT GTGCACTGCC GCATGGCGGC CCCTAGCCAA      3900
AGGAAAGCTG TTTTGTCCAC GCTGGTAGGC CGGTATGGCA GACGCACAAG GCTTTATGAT      3960
GCGGGTCACA CCGATGTCCG CGCCTCCCTT GCGCGCTTTA TTCCCACTCT CGGGCGGGTT      4020
ACTGCCACCA CCTGTGAACT CTTTGAGCTT GTAGAGGCGA TGGTGGAGAA GGGCCAAGAC      4080
GGTTCAGCCG TCCTCGAGTT GGATTTGTGC AGCCGAGATG TCTCCCGCAT AACCTTTTC      4140
CAGAAGGATT GTAACAAGTT CACGACCGGC GAGACAATTG CGCATGGCAA AGTCGGTCAG      4200
GGTATCTTCC GCTGGAGTAA GACGTTTTGT GCCCTGTTTG GCCCCTGGTT CCGTGCGATT      4260
GAGAAGGCTA TTCTATCCCT TTTACCACAA GCTGTGTTCT ACGGGGATGC TTATGACGAC      4320
TCAGTATTCT CTGCTGCCGT GGCTGGCGCC AGCCATGCCA TGGTGTTTGA AAATGATTTT      4380
TCTGAGTTTG ACTCGACTCA GAATAACTTT TCCCTAGGTC TTGAGTGCGC CATTATGGAA      4440
GAGTGTGGTA TGCCCCAGTG GCTTGTCAGG TTGTACCATG CCGTCCGGTC GGCGTGGATC      4500
CTGCAGGCCC CAAAAGAGTC TTTGAGAGGG TTCTGGAAGA AGCATTCTGG TGAGCCGGGC      4560
AGCTTGCTCT GGAATACGGT GTGGAACATG GCAATCATTG CCCATTGCTA TGAGTTCCGG      4620
GACCTCCAGG TTGCCGCCTT CAAGGGCGAC GACTCGGTCG TCCTCTGTAG TGAATACCGC      4680
CAGAGCCCAG GCGCCGGTTC GCTTATAGCA GGCTGTGGTT TGAAGTTGAA GGCTGACTTC      4740
CGGCCGATTG GGCTGTATGC CGGGGTTGTC GTCGCCCCGG GGCTCGGGGC CCTACCCGAT      4800
GTCGTTCGAT TCGCCGGACG GCTTTCGGAG AAGAACTGGG GGCCTGATCC GGAGCGGGCA      4860
```

```
GAGCAGCTCC GCCTCGCCGT GCAGGATTTC CTCCGTAGGT TAACGAATGT GGCCCAGATT    4920
TGTGTTGAGG TGGTGTCTAG AGTTTACGGG GTTTCCCCGG GTCTGGTTCA TAACCTGATA    4980
GGCATGCTCC AGACTATTGG TGATGGTAAG GCGCATTTTA CAGAGTCTGT TAAGCCTATA    5040
CTTGACCTTA CACACTCAAT TATGCACCGG TCTGAATGAA TAACATGTGG TTTGCTGCGC    5100
CCATGGGTTC GCCACCATGC GCCCTAGGCC TCTTTTGCTG TTGTTCCTCT TGTTTCTGCC    5160
TATGTTGCCC GCGCCACCGA CCGGTCAGCC GTCTGGCCGC CGTCGTGGGC GGCGCAGCGG    5220
CGGTACCGGC GGTGGTTTCT GGGGTGACCG GGTTGATTCT CAGCCCTTCG CAATCCCCTA    5280
TATTCATCCA ACCAACCCCT TTGCCCCAGA CGTTGCCGCT GCGTCCGGGT CTGGACCTCG    5340
CCTTCGCCAA CCAGCCCGGC CACTTGGCTC CACTTGGCGA GATCAGGCCC AGCGCCCCTC    5400
CGCTGCCTCC CGTCGCCGAC CTGCCACAGC CGGGGCTGCG GCGCTGACGG CTGTGGCGCC    5460
TGCCCATGAC ACCTCACCCG TCCCGGACGT TGATTCTCGC GGTGCAATTC TACGCCGCCA    5520
GTATAATTTG TCTACTTCAC CCCTGACATC CTCTGTGGCC TCTGGCACTA ATTTAGTCCT    5580
GTATGCAGCC CCCCTTAATC CGCCTCTGCC GCTGCAGGAC GGTACTAATA CTCACATTAT    5640
GGCCACAGAG GCCTCCAATT ATGCACAGTA CCGGGTTGCC CGCGCTACTA TCCGTTACCG    5700
GCCCCTAGTG CCTAATGCAG TTGGAGGCTA TGCTATATCC ATTTCTTTCT GGCCTCAAAC    5760
AACCACAACC CCTACATCTG TTGACATGAA TTCCATTACT TCCACTGATG TCAGGATTCT    5820
TGTTCAACCT GGCATAGCAT CTGAATTGGT CATCCCAAGC GAGCGCCTTC ACTACCGCAA    5880
TCAAGGTTGG CGCTCGGTTG AGACATCTGG TGTTGCTGAG GAGGAAGCCA CCTCCGGTCT    5940
TGTCATGTTA TGCATACATG GCTCTCCAGT TAACTCCTAT ACCAATACCC CTTATACCGG    6000
TGCCCTTGGC TTACTGGACT TTGCCTTAGA GCTTGAGTTT CGCAATCTCA CCACCTGTAA    6060
CACCAATACA CGTGTGTCCC GTTACTCCAG CACTGCTCGT CACTCCGCCC GAGGGGCCGA    6120
CGGGACTGCG GAGCTGACCA CAACTGCAGC CACCAGGTTC ATGAAAGATC TCCACTTTAC    6180
CGGCCTTAAT GGGGTAGGTG AAGTCGGCCG CGGGATAGCT CTAACATTAC TTAACCTTGC    6240
TGACACGCTC CTCGGCGGGC TCCCGACAGA ATTAATTTCG TCGGCTGGCG GGCAACTGTT    6300
TTATTCCCGC CCGGTTGTCT CAGCCAATGG CGAGCCAACC GTGAAGCTCT ATACATCAGT    6360
GGAGAATGCT CAGCAGGATA AGGGTGTTGC TATCCCCCAC GATATCGATC TTGGTGATTC    6420
GCGTGTGGTC ATTCAGGATT ATGACAACCA GCATGAGCAG GATCGGCCCA CCCCGTCGCC    6480
TGCGCCATCT CGGCCTTTTT CTGTTCTCCG AGCAAATGAT GTACTTTGGC TGTCCCTCAC    6540
TGCAGCCGAG TATGACCAGT CCACTTACGG GTCGTCAACT GGCCCGGTTT ATATCTCGGA    6600
CAGCGTGACT TTGGTGAATG TTGCGACTGG CGCGCAGGCC GTAGCCCGAT CGCTTGACTG    6660
GTCCAAAGTC ACCCTCGACG GGCGGCCCCT CCCGACTGTT GAGCAATATT CCAAGACATT    6720
CTTTGTGCTC CCCCTTCGTG GCAAGCTCTC CTTTTGGGAG GCCGGCACAA CAAAAGCAGG    6780
TTATCCTTAT AATTATAATA CTACTGCTAG TGACCAGATT CTGATTGAAA ATGCTGCCGG    6840
CCATCGGGTC GCCATTTCAA CCTATACCAC CAGGCTTGGG GCCGGTCCGG TCGCCATTTC    6900
TGCGGCCGCG GTTTTGGCTC CACGCTCCGC CCTGGCTCTG CTGGAGGATA CTTTTGATTA    6960
TCCGGGGCGG GCGCACACAT TTGATGACTT CTGCCCTGAA TGCCGCGCTT TAGGCCTCCA    7020
GGGTTGTGCT TTCCAGTCAA CTGTCGCTGA GCTCCAGCGC CTTAAAGTTA AGGTGGGTAA    7080
AACTCGGGAG TTGTAGTTTA TTTGGCTGTG CCCACCTACT TATATCTGCT GATTTCCTTT    7140
ATTTCCTTTT TCTCGGTCCC GCGCTCCCTG A                                  7171
```

( 2 ) INFORMATION FOR SEQ ID NO:11:

(i) SEQUENCE CHARACTERISTICS:
    (A) LENGTH: 1575 base pairs
    (B) TYPE: nucleic acid
    (C) STRANDEDNESS: double
    (D) TOPOLOGY: linear (ii) MOLECULE TYPE: DNA (iii) HYPOTHETICAL: NO (iv) ANTI-SENSE: NO (v) ORIGINAL SOURCE:
    (C) INDIVIDUAL ISOLATE: T: Mexican strain (xi) SEQUENCE DESCRIPTION: SEQ ID NO:11:

```
GTTGCGTGAG GTGGGTATCT CAGATGCCAT TGTTAATAAT TTCTTCCTTT CGGGTGGCGA      60
GGTTGGTCAC CAGAGACCAT CGGTCATTCC GCGAGGCAAC CCTGACCGCA ATGTTGACGT     120
GCTTGCGGCG TTTCCACCTT CATGCCAAAT AAGCGCCTTC CATCAGCTTG CTGAGGAGCT     180
GGGCCACCGG CCGGCGCCGG TGGCGGCTGT GCTACCTCCC TGCCCTGAGC TTGAGCAGGG     240
CCTTCTCTAT CTGCCACAGG AGCTAGCCTC CTGTGACAGT GTTGTGACAT TGAGCTAAC     300
TGACATTGTG CACTGCCGCA TGGCGGCCCC TAGCCAAAGG AAAGCTGTTT TGTCCACGCT     360
GGTAGGCCGG TATGGCAGAC GCACAAGGCT TTATGATGCG GGTCACACCG ATGTCCGCGC     420
CTCCCTTGCG CGCTTTATTC CCACTCTCGG GCGGGTTACT GCCACCACCT GTGAACTCTT     480
TGAGCTTGTA GAGGCGATGG TGGAGAAGGG CCAAGACGGT TCAGCCGTCC TCGAGTTGGA     540
TTTGTGCAGC CGAGATGTCT CCCGCATAAC CTTTTCCAG AAGGATTGTA ACAAGTTCAC     600
GACCGGCGAG ACAATTGCGC ATGGCAAAGT CGGTCAGGGT ATCTTCCGCT GGAGTAAGAC     660
CTTTTGTGCC CTGTTTGGCC CCTGGTTCCG TGCGATTGAG AAGGCTATTC TATCCCTTTT     720
ACCACAAGCT GTGTTCTACG GGGATGCTTA TGACGACTCA GTATTCTCTG CTGCCGTGGC     780
TGGCGCCAGC CATGCCATGG TGTTTGAAAA TGATTTTTCT GAGTTTGACT CGACTCAGAA     840
TAACTTTTCC CTAGGTCTTG AGTGCGCCAT TATGGAAGAG TGTGGTATGC CCCAGTGGCT     900
TGTCAGGTTG TACCATGCCG TCCGGTCGGC GTGGATCCTG CAGGCCCCAA AAGAGTCTTT     960
GAGAGGGTTC TGGAAGAAGC ATTCTGGTGA GCCGGGCACG TTGCTCTGGA ATACGGTGTG    1020
GAACATGGCA ATCATTGCCC ATTGCTATGA GTTCCGGGAC CTCCAGGTTG CCGCCTTCAA    1080
GGGCGACGAC TCGGTCGTCC TCTGTAGTGA ATACCGCCAG AGCCCAGGCG CCGGTTCGCT    1140
TATAGCAGGC TGTGGTTTGA AGTTGAAGGC TGACTTCCGG CCGATTGGGC TGTATGCCGG    1200
GGTTGTCGTC GCCCCGGGGC TCGGGCCCT ACCCGATGTC GTTCGATTCG CCGGACGGCT    1260
TTCGGAGAAG AACTGGGGGC CTGATCCGGA GCGGGCAGAG CAGCTCCGCC TCGCCGTGCA    1320
GGATTTCCTC CGTAGGTTAA CGAATGTGGC CCAGATTTGT GTTGAGGTGG TGTCTAGAGT    1380
TTACGGGGTT TCCCCGGGTC TGGTTCATAA CCTGATAGGC ATGCTCCAGA CTATTGGTGA    1440
TGGTAAGGCG CATTTTACAG AGTCTGTTAA GCCTATACTT GACCTTACAC ACTCAATTAT    1500
GCACCGGTCT GAATGAATAA CATGTGGTTT GCTGCGCCCA TGGGTTCGCC ACCATGCGCC    1560
CTAGGCCTCT TTTGC                                                    1575
```

(2) INFORMATION FOR SEQ ID NO:12:

(i) SEQUENCE CHARACTERISTICS:
        (A) LENGTH: 874 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
    (C) INDIVIDUAL ISOLATE: Tashkent strain (xi) SEQUENCE DESCRIPTION: SEQ ID NO:12:

| | | | | | |
|---|---|---|---|---|---|
| CGGGCCCCGT | ACAGGTCACA | ACCTGTGAGT | TGTACGAGCT | AGTGGAGGCC | ATGGTCGAGA | 60 |
| AAGGCCAGGA | TGGCTCCGCC | GTCCTTGAGC | TCGATCTCTG | CAACCGTGAC | GTGTCCAGGA | 120 |
| TCACCTTTTT | CCAGAAAGAT | TGCAATAAGT | TCACCACGGG | AGAGACCATC | GCCCATGGTA | 180 |
| AAGTGGGCCA | GGGCATTTCG | GCCTGGAGTA | AGACCTTCTG | TGCCCTTTTC | GGCCCCTGGT | 240 |
| TCCGTGCTAT | TGAGAAGGCT | ATTCTGGCCC | TGCTCCCTCA | GGGTGTGTTT | TATGGGGATG | 300 |
| CCTTTGATGA | CACCGTCTTC | TCGGCGCGTG | TGGCCGCAGC | AAAGGCGTCC | ATGGTGTTTG | 360 |
| AGAATGACTT | TTCTGAGTTT | GACTCCACCC | AGAATAATTT | TTCCCTGGGC | CTAGAGTGTG | 420 |
| CTATTATGGA | GAAGTGTGGG | ATGCCGAAGT | GGCTCATCCG | CTTGTACCAC | CTTATAAGGT | 480 |
| CTGCGTGGAT | CCTGCAGGCC | CCGAAGGAGT | CCCTGCGAGG | GTGTTGGAAG | AAACACTCCG | 540 |
| GTGAGCCCGG | CACTCTTCTA | TGGAATACTG | TCTGGAACAT | GGCCGTTATC | ACCCATTGTT | 600 |
| ACGATTTCCG | CGATTTGCAG | GTGGCTGCCT | TTAAAGGTGA | TGATTCGATA | GTGCTTTGCA | 660 |
| GTGAGTACCG | TCAGAGTCCA | GGGGCTGCTG | TCCTGATTGC | TGGCTGTGGC | TTAAAGCTGA | 720 |
| AGGTGGGTTT | CCGTCCGATT | GGTTTGTATG | CAGGTGTTGT | GGTGACCCCC | GGCCTTGGCG | 780 |
| CGCTTCCCGA | CGTCGTGCGC | TTGTCCGGCC | GGCTTACTGA | GAAGAATTGG | GGCCCTGGCC | 840 |
| CTGAGCGGGC | GGAGCAGCTC | CGCCTTGCTG | TGCG | | | 874 |

(2) INFORMATION FOR SEQ ID NO:13:

(i) SEQUENCE CHARACTERISTICS:
    (A) LENGTH: 449 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (vi) ORIGINAL SOURCE:
    (C) INDIVIDUAL ISOLATE: Clone 406.4- 2 cDNA (ix) FEATURE:
    (A) NAME/KEY: CDS
    (B) LOCATION: 2..100

(xi) SEQUENCE DESCRIPTION: SEQ ID NO:13:

```
C GCC AAC CAG CCC GGC CAC TTG GCT CCA TTT GGC GAG ATC AGG CCC        46
  Ala Asn Gln Pro Gly His Leu Ala Pro Leu Gly Glu Ile Arg Pro
  1               5                   10                  15

AGC GCC CCT CCG CTG CCT CCC GTC GCC GAC CTG CCA CAG CCG GGG CTG     94
Ser Ala Pro Pro Leu Pro Pro Val Ala Asp Leu Pro Gln Pro Gly Leu
            20                  25                  30

CGG CGC TGACGGCTGT GGCGCCTGCC CATGACACCT CACCCGTCCC GGACGTTGAT      150
Arg Arg

TCTCGCGGTG CAATTCTACG CCGCCAGTAT AATTTGTCTA CTTCACCCCT GACATCCTCT   210

GTGGCCTCTG GCACTAATTT AGTCCTGTAT GCAGCCCCCC TTAATCCGCC TCTGCCGCTG   270
```

```
CAGGACGGTA CTAATACTCA CATTATGGCC ACAGAGGCCT CCAATTATGC ACAGTACCGG    330

GTTGCCCGCG CTACTATCCG TTACCGGCCC CTAGTGCCTA ATGCAGTTGG AGGCTATGCT    390

ATATCCATTT CTTTCTGGCC TCAAACAACC ACAACCCCTA CATCTGTTGA CATGAATTC    449
```

(2) INFORMATION FOR SEQ ID NO:14:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:14:

```
Ala Asn Gln Pro Gly His Leu Ala Pro Leu Gly Glu Ile Arg Pro Ser
 1               5                  10                  15

Ala Pro Pro Leu Pro Pro Val Ala Asp Leu Pro Gln Pro Gly Leu Arg
            20                  25                  30

Arg
```

(2) INFORMATION FOR SEQ ID NO:15:

(i) SEQUENCE CHARACTERISTICS:
        (A) LENGTH: 130 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Clone 406.3-2

(ix) FEATURE:
        (A) NAME/KEY: CDS
        (B) LOCATION: 5..130

(xi) SEQUENCE DESCRIPTION: SEQ ID NO:15:

```
GGAT ACT TTT GAT TAT CCG GGG CGG GCG CAC ACA TTT GAT GAC TTC TGC    49
     Thr Phe Asp Tyr Pro Gly Arg Ala His Thr Phe Asp Asp Phe Cys
      1               5                  10                  15

CCT GAA TGC CGC GCT TTA GGC CTC CAG GGT TGT GCT TTC CAG TCA ACT    97
Pro Glu Cys Arg Ala Leu Gly Leu Gln Gly Cys Ala Phe Gln Ser Thr
                 20                  25                  30

GTC GCT GAG CTC CAG CGC CTT AAA GTT AAG GTT                       130
Val Ala Glu Leu Gln Arg Leu Lys Val Lys Val
             35                  40
```

(2) INFORMATION FOR SEQ ID NO:16:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:16:

```
Thr Phe Asp Tyr Pro Gly Arg Ala His Thr Phe Asp Asp Phe Cys Pro
 1               5                  10                  15

Glu Cys Arg Ala Leu Gly Leu Gln Gly Cys Ala Phe Gln Ser Thr Val
            20                  25                  30
```

Ala Glu Leu Gln Arg Leu Lys Val Lys Val
                35                  40

(2) INFORMATION FOR SEQ ID NO:17:

(i) SEQUENCE CHARACTERISTICS:
        (A) LENGTH: 33 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: 406.4-2 epitope - Mexican strain (xi) SEQUENCE DESCRIPTION: SEQ ID NO:17:

Ala Asn Gln Pro Gly His Leu Ala Pro Leu Gly Glu Ile Arg Pro Ser
1                   5                   10                  15

Ala Pro Pro Leu Pro Pro Val Ala Asp Leu Pro Gln Pro Gly Leu Arg
                20                  25                  30

Arg (2) INFORMATION FOR SEQ ID NO:18:

(i) SEQUENCE CHARACTERISTICS:
        (A) LENGTH: 33 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: 406.4-2 epitope - Burma strain (xi) SEQUENCE DESCRIPTION: SEQ ID NO:18:

Ala Asn Pro Pro Asp His Ser Ala Pro Leu Gly Val Thr Arg Pro Ser
1                   5                   10                  15

Ala Pro Pro Leu Pro His Val Val Asp Leu Pro Gln Leu Gly Pro Arg
                20                  25                  30

Arg (2) INFORMATION FOR SEQ ID NO:19:

(i) SEQUENCE CHARACTERISTICS:
        (A) LENGTH: 42 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: 406.3-2 epitope - Mexican strain (xi) SEQUENCE DESCRIPTION: SEQ ID NO:19:

-continued

```
Thr Phe Asp Tyr Pro Gly Arg Ala His Thr Phe Asp Asp Phe Cys Pro
 1           5              10               15
Glu Cys Arg Ala Leu Gly Leu Gln Gly Cys Ala Phe Gln Ser Thr Val
            20              25              30
Ala Glu Leu Gln Arg Leu Lys Val Lys Val
            35              40
```

(2) INFORMATION FOR SEQ ID NO:20:

(i) SEQUENCE CHARACTERISTICS:
        (A) LENGTH: 42 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: 406.3-2 epitope - Burma strain (xi) SEQUENCE DESCRIPTION: SEQ ID NO:20:

```
Thr Leu Asp Tyr Pro Ala Arg Ala His Thr Phe Asp Asp Phe Cys Pro
 1           5              10               15
Glu Cys Arg Pro Leu Gly Leu Gln Gly Cys Ala Phe Gln Ser Thr Val
            20              25              30
Ala Glu Leu Gln Arg Leu Lys Met Lys Val
            35              40
```

DNA SEQUENCES OF ENTERICALLY TRANSMITTED NON-A/NON-B HEPATITIS VIRAL AGENT AND CHARACTERISTIC EPITOPES THEREOF

CROSS-REFERENCE TO RELATED APPLICATIONS

This application is a division of application Ser. No. 08/279,823, filed Jul. 25, 1994, herein incorporated by reference, which is a continuation-in-part of U.S. application Ser. No. 07/505,888, filed Apr. 5, 1990, now abandoned, which is a continuation-in-part of U.S. application Ser. No. 420,921, filed Oct. 13, 1989, now abandoned, which is a continuation-in-part of U.S. application Ser. No. 367,486, filed Jun. 16, 1989, now abandoned, which is a continuation-in-part of U.S. application Ser. No. 336,672, filed Apr. 11, 1989, now abandoned, which is a continuation-in-part of U.S. application Ser. No. 208,997, filed Jun. 17, 1988, now abandoned, all of which are herein incorporated by reference.

INTRODUCTION

1. Field of Invention

This invention relates to recombinant proteins, genes, and gene probes and more specifically to such proteins and probes derived from an enterically transmitted nonA/nonB hepatitis viral agent, to diagnostic methods and vaccine applications which employ the proteins and probes, and to gene segments that encode specific epitopes (and proteins artificially produced to contain those epitopes) that are particularly useful in diagnosis and prophylaxis.

2. Background

Enterically transmitted non-A/non-B hepatitis viral agent (ET-NANB; also referred to herein as HEV) is the reported cause of hepatitis in several epidemics and sporadic cases in Asia, Africa, Europe, Mexico, and the Indian subcontinent. Infection is usually by water contaminated with feces, although the virus may also spread by close physical contact. The virus does not seem to cause chronic infection. The viral etiology in ET-NANB has been demonstrated by infection of volunteers with pooled fecal isolates; immune electron microscopy (IEM) studies have shown virus particles with 27–34 nm diameters in stools from infected individuals. The virus particles reacted with antibodies in serum from infected individuals from geographically distinct regions, suggesting that a single viral agent or class is responsible for the majority of ET-NANB hepatitis seen worldwide. No antibody reaction was seen in serum from individuals infected with parenterally transmitted NANB virus (also known as hepatitis C virus or HCV), indicating a different specificity between the two NANB types.

In addition to serological differences, the two types of NANB infection show distinct clinical differences. ET-NANB is characteristically an acute infection, often associated with fever and arthralgia, and with portal inflammation and associated bile stasis in liver biopsy specimens (Arankalle). Symptoms are usually resolved within six weeks. Parenterally transmitted NANB, by contrast, produces a chronic infection in about 50% of the cases. Fever and arthralgia are rarely seen, and inflammation has a predominantly parenchymal distribution (Khuroo, 1980). The course of ET-NANBH is generally uneventful in healthy individuals, and the vast majority of those infected recover without the chronic sequelae seen with HCV. One peculiar epidemiologic feature of this disease, however, is the markedly high mortality observed in pregnant women; this is reported in numerous studies to be on the order of 10–20%. This finding has been seen in a number of epidemiologic studies but at present remains unexplained. Whether this reflects viral pathogenicity, the lethal consequence of the interaction of virus and immune suppressed (pregnant) host, or a reflection of the debilitated prenatal health of a susceptible malnourished population remains to be clarified.

The two viral agents can also be distinguished on the basis of primate host susceptibility. ET-NANB, but not the parenterally transmitted agent, can be transmitted to cynomolgus monkeys. The parenterally transmitted agent is more readily transmitted to chimpanzees than is ET-NANB (Bradley, 1987).

There have been major efforts worldwide to identify and clone viral genomic sequences associated with ET-NANB hepatitis. One goal of this effort, requiring virus-specific genomic sequences, is to identify and characterize the nature of the virus and its protein products. Another goal is to produce recombinant viral proteins which can be used in antibody-based diagnostic procedures and for a vaccine. Despite these efforts, viral sequences associated with ET-NANB hepatitis have not been successfully identified or cloned heretofore, nor have any virus-specific proteins been identified or produced.

Relevant Literature

Arankalle, V. A., et al., The Lancet, 550 (Mar. 12, 1988).
Bradley, D. W., et al., J Gen. Virol., 69:1 (1988).
Bradley, D. W. et al., Proc. Nat. Acad. Sci., USA, 84:6277 (1987).
Gravelle, C. R. et al., J. Infect. Diseases, 131:167 (1975).
Kane, M. A., et al., JAMA, 252:3140 (1984).
Khuroo, M. S., Am. J. Med., 48:818 (1980).
Khuroo, M. S., et al., Am. J. Med., 68:818 (1983).
Maniatis, T., et al. Molecular Cloning: A Laboratory Manual, Cold Spring Harbor Laboratory (1982).
Seto, B., et al., Lancet, 11:941 (1984).
Sreenivasan, M. A., et al., J. Gen. Virol., 65:1005 (1984).
Tabor, E., et al., J. Infect. Dis., 140:789 (1979).

SUMMARY OF THE INVENTION

Novel compositions, as well as methods of preparation and use of the compositions are provided, where the compositions comprise viral proteins and fragments thereof derived from the viral agent for ET-NANB. A number of specific fragments of viral proteins (and the corresponding genetic sequences) that are particularly useful in diagnosis and vaccine production are also disclosed. Methods for preparation of ET-NANB viral proteins include isolating ET-NANB genomic sequences which are then cloned and expressed in a host cell. The resultant recombinant viral proteins find use as diagnostic agents and as vaccines. The genomic sequences and fragments thereof find use in preparing ET-NANB viral proteins and as probes for virus detection.

DESCRIPTION OF SPECIFIC EMBODIMENTS

Figure 1:
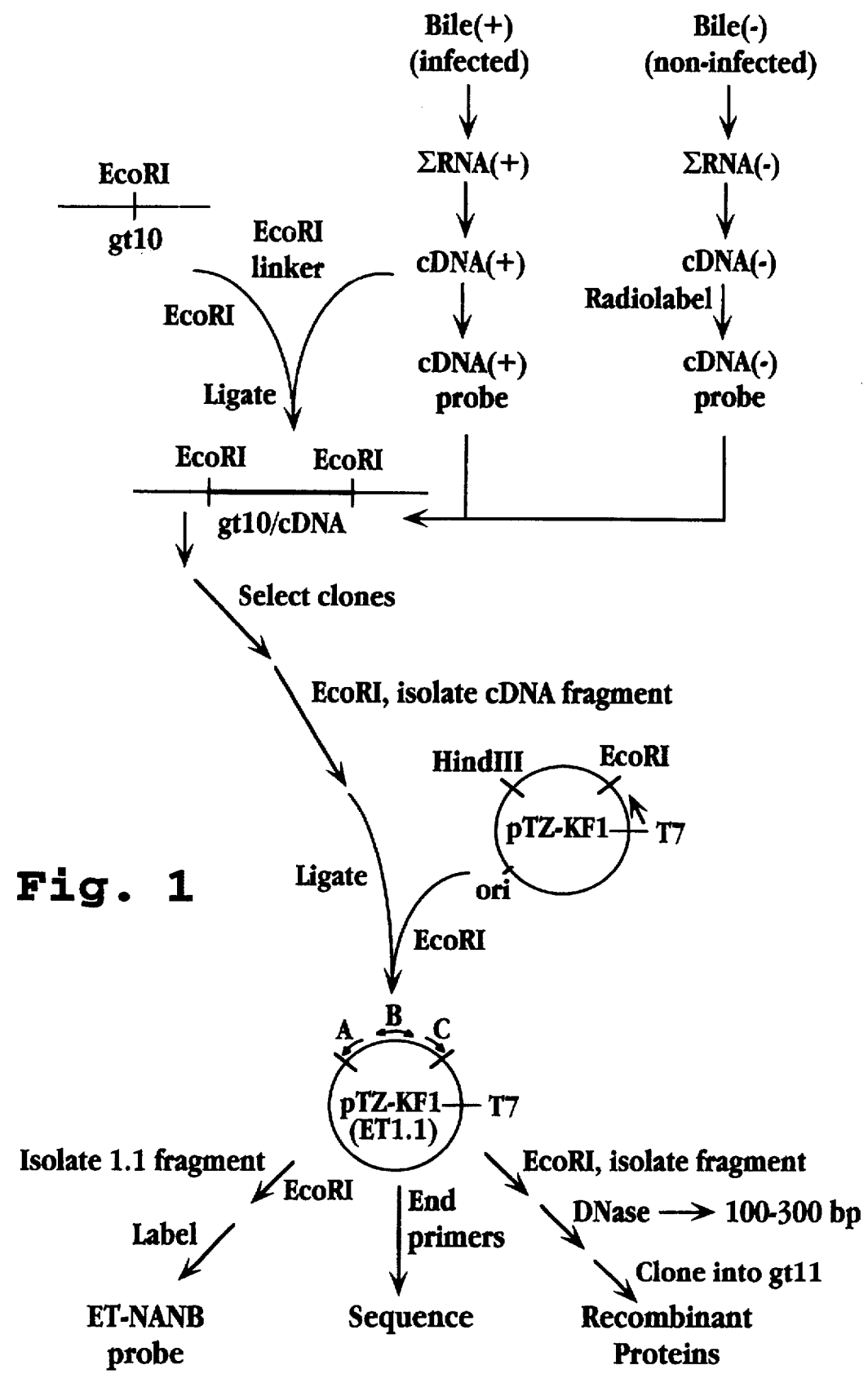
FIG. 1 shows vector constructions and manipulations used in obtaining and sequencing cloned ET-NANB fragment.

Novel compositions comprising generic sequences and fragments thereof derived from the viral agent for ET-NANB are provided, together with recombinant viral proteins produced using the genomic sequences and methods of using these compositions. Epitopes on the viral protein have been identified that are particularly useful in diagnosis and vaccine production. Small peptides containing the epitopes are recognized by multiple sera of patients infected with ET-NANB.

The molecular cloning of HEV was accomplished by two very different approaches. The first successful identification of a molecular clone was based on the differential hybridization of putative HEV cDNA clones to heterogeneous cDNA from infected and uninfected cyno bile. cDNAs from both sources were labeled to high specific activity with $^{32}P$ to identify a clone that hybridized specifically to the infected source probe. A cyno monkey infected with the Burma isolate of HEV was used in these first experiments. The sensitivity of this procedure is directly related to the relative abundance of the specific sequence against the overall background. In control experiments, it was found that specific identification of a target sequence may be obtained with as little as 1 specific part per 1000 background sequences. A number of clones were identified by this procedure using libraries and probes made from infected (Burma isolate) and control uninfected cyno bile. The first extensively characterized clone of the 16 plaques purified by this protocol was given the designation ET1.1.

ET1.1 was first characterized as both derived from and unique to the infected source cDNA. Heterogeneous cDNA was amplified from both infected and uninfected sources using a sequence independent single premier amplification technique (SISPA). This technique is described in copending application Ser. No. 208,512, filed Jun. 17, 1988. The limited pool of cDNA made from Burma infected cyno bile could then be amplified enzymatically prior to cloning or hybridization using putative HEV clones as probes. ET1.1 hybridized specifically to the original bile cDNA from the infected source. Further validation of this clone as derived from the genome of HEV was demonstrated by the similarity of the ET1.1 sequence and those present in SISPA cDNA prepared from five different human stool samples collected from different ET-NANBH epidemics including Somalia, Tashkent, Borneo, Mexico and Pakistan. These molecular epidemiologic studies established the isolated sequence as derived from the virus that represented the major cause of ET-NANBH worldwide.

The viral specificity of ET1.1 was further established by the finding that the clone hybridized specifically to RNA extracted from infected cyno liver. Hybridization analysis of polyadenylated RNA demonstrated a unique 7.5 Kb polyadenylated transcript not present in uninfected liver. The size of this transcript suggested that it represented the full length viral genome. Strand specific oligonucleotides were also used to probe viral genomic RNA extracted directly from semi-purified virions prepared from human stool. The strand specificity was based on the RNA-directed RNA polymerase (RDRP) open reading frame (ORF) identified in ET1.1 (see below). Only the probe detecting the sense strand hybridized to the nucleic acid. These studies characterized HEV as a plus sense, single stranded genome. Strand specific hybridization to RNA extracted from the liver also established that the vast majority of intracellular transcript was positive sense. Barring any novel mechanism for virus expression, the negative strand, although not detectable, would be present at a ratio of less than 1:100 when compared with the sense strand.

ET1.1 was documented as exogenous when tested by both Southern blot hybridization and PCR using genomic DNAs derived from uninfected humans, infected and uninfected cynos and also the genomic DNAs from E. coli and various bacteriophage sources. The latter were tested in order to rule out trivial contamination with an exogenous sequence introduced during the numerous enzymatic manipulations performed during cDNA construction and amplification. It was also found that the nucleotide sequence of the ET1.1 clone was not homologous to any entries in the Genebank database. The translated open reading frame of the ET1.1 clone did, however, demonstrate limited homology with consensus amino acid residues consistent with an RNA-directed RNA polymerase. This consensus amino acid motif is shared among all positive strand RNA viruses and, as noted above, is present at the 3' end of the HCV genome. The 1.3 Kb clone was therefore presumed to be derived, at least in part, from the nonstructural portion of the viral genome.

Because of the relationship of different strains of ET-NANB to each other that has been demonstrated by the present invention, the genome of the ET-NANB viral agent is defined in this specification as containing a region which is homologous to the 1.33 kb DNA EcoRI insert present in plasmid pTZKF1 (ET1.1) carried in E. coli strain BB4 and having ATCC deposit no. 67717. The entire sequence, in both directions, has now been identified as set forth below. The sequences of both strands are provided, since both strands can encode proteins. However, the sequence in one direction has been designated as the "forward" sequence because of statistical similarities to known proteins and because the forward sequence is known to be predominately protein-encoding. This sequence is set forth below along with the three possible translation sequences. There is one long open reading frame that starts at nucleotide 145 with an isoleucine and extends to the end of the sequence. The two other reading frames have many termination codons. Standard abbreviations for nucleotides and amino acids are used here and elsewhere in this specification.

The gene sequence is substantially identical to one given in the parent application. The present sequence differs in the omission of the first 37 nucleotides at the 5' end and last 13 nucleotides at the 3' end, which are derived from the linker used for cloning rather than from the virus. In addition, a G was omitted at position 227 of the sequence given in the parent application.

The gene sequence has SEQ ID NO.1; the first amino acid sequence in reading frame beginning with nucleotide 1 has SEQ ID NO.2.

The complementary strand, referred to here as the "reverse sequence," is set forth below in the same manner as the forward sequence set forth above. Several open reading frames, shorter than the long open reading frame found in the forward sequence, can be seen in this reverse sequence. Because of the relative brevity of the open reading frames in the reverse direction, they are probably not expressed.

The gene sequence has SEQ ID NO.5.

Identity of this sequence with sequences in etiologic agents has been confirmed by locating a corresponding sequence in a viral strain isolated in Burma. The Burmese isolate contains the following sequence of nucleotides (one strand and open reading frames shown). The gene sequence has SEQ ID NO.6; the protein sequence corresponding to ORF1 has SEQ ID NO.7; ORF2 has SEQ ID NO.8; and ORF3 has SEQ ID NO.9.

Total number of bases in the nucleotide sequence as presented is 7195. The poly-A tail present in the cloned sequence has been omitted.

The ability of the methods described herein to isolate and identify genetic material from other NANB hepatitis strains has been confirmed by identifying genetic material from an isolate obtained in Mexico. The sequence of this isolate was about 75% identical to the ET1.1 sequence set forth in SEQ ID NO.1 above. The sequence was identified by hybridization using the conditions set forth in Section II.B below.

In this different approach to isolation of the virus, cDNA libraries were made directly from a semi-purified human stool specimen collected from an outbreak of ET-NANB in Telixtac. The recovery of cDNA and the construction of representative libraries was assured by the application of sequence independent single premier amplification (SISPA). A cDNA library constructed in lambda gt11 from such an amplified cDNA population was screened with a serum considered to have "high" titer anti-HEV antibodies as assayed by direct immunofluorescence on liver sections from infected cynos. Two cDNA clones, denoted 406.3-2 and 406.4-2, were identified by this approach from a total of 60,000 screened. The sequence of these clones was subsequently localized to the 3' half of the viral genome by homology comparison to the HEV (Burma) sequence obtained from clones isolated by hybridization screening of libraries with the original ET1.1 clone.

These isolated cDNA epitopes when used as hybridization probes on Northern blots of RNA extracted from infected cyno liver gave a somewhat different result when compared to the Northern blots obtained with the ET1.1 probe. In addition to the single 7.5 Kb transcript seen using ET1.1, two additional transcripts of 3.7 and 2.0 Kb were identified using either of these epitopes as hybridization probes. These polyadenylated transcripts were identified using the extreme 3' end epitope clone (406.3-2) as probe and therefore established these transcripts as co-terminal with the 3' end of the genome (see below). One of the epitope clones (406.4-2) was subsequently shown to react in a specific fashion with antisera collected from 5 different geographic epidemics (Somalia, Burma, Mexico, Tashkent and Pakistan). The 406.3-2 clone reacted with sera from 4 out of these same 5 epidemics (Yarbough et al., 1990). Both clones reacted with only post inoculation antisera from infected cynos. The latter experiment confirmed that seroconversion in experimentally infected cynos was related to the isolated exogenous cloned sequence.

A composite cDNA sequence (obtained from several clones of the Mexican strain) is the Composite Mexico strain sequence (SEQ ID NO.10).

The sequence was obtained from polyadenylated clones. For clarity the 3' polyA "tail" has been omitted.

The sequence includes a partial cDNA sequence consisting of 1661 nucleotides that was identified in a previous application in this series. The previously identified partial sequence is set forth below, with certain corrections (SEQ ID NO.11). The corrections include deletion of the first 80 bases of the prior reported sequence, which are cloning artifacts; insertion of G after former position 174, of C after 270, and of GGCG after 279; change of C to T at former position 709, of GC to CG at 722–723, of CC to TT at 1238–39, and of C to G at 1606; deletion of T at former position 765; and deletion of the last 11 bases of the former sequence, which are part of a linker sequence and are not of viral origin.

When comparing the Burmese and Mexican strains, 75.7% identity is seen in a 7189 nucleotide overlap beginning at nucleotide 1 of the Mexican strain and nucleotide 25 of the Burmese strain.

In the same manner, a different strain of HEV was identified in an isolate obtained in Tashkent, U.S.S.R. The Tashkent sequence is given as SEQ ID NO.12.

As shown in the following comparison of sequences, the Tashkent (Tash.) sequence more closely resembles the Burma sequence than the Mexico sequence, as would be expected of two strains from more closely related geographical areas. The numbering system used in the comparison is based on the Burma sequence. As indicated previously, Burma has SEQ ID NO:6; Mexico, SEQ ID NO:10; and Tashkent, SEQ ID NO:12. The letters present in the lines between the sequences indicate conserved nucleotides.

```
              10v         20v         30v         40v         50v         60v
-BURMA   AGGCAGACCACATATGTGGTCGATGCCATGGAGGCCCATCAGTTTATTAAGGCTCCTGGCA
                                     GCCATGGAGGCCCA CAGTT ATTAAGGCTCCTGGCA
-MEXICO                              GCCATGGAGGCCCACCAGTTCATTAAGGCTCCTGGCA 70v         80v         90v        100v        110v        120v
-BURMA   TCACTACTGCTATTGAGCAGGCTGCTCTAGCAGCGGCCAACTCTGCCCTGGCGAATGCTG
         TCACTACTGCTATTGAGCA GC GCTCTAGCAGCGGCCAACTC GCCCT GCGAATGCTG
-MEXICO  TCACTACTGCTATTGAGCAAGCAGCTCTAGCAGCGGCCAACTCCGCCCTTGCGAATGCTG 130v        140v        150v        160v        170v        180v
-BURMA   TGGTAGTTAGGCCTTTTCTCTCTCACCAGCAGATTGAGATCCTCATTAACCTAATGCAAC
         TGGT GT  GGCCTTT CT TC CA CAGCAG TTGAGATCCT AT AA CT ATGCAAC
-MEXICO  TGGTGGTCCGGCCTTTCCTTTCCCATCAGCAGGTTGAGATCCTTATAAATCTCATGCAAC 190v        200v        210v        220v        230v        240v
-BURMA   CTCGCCAGCTTGTTTTCCGCCCCGAGGTTTTCTGGAATCATCCCATCCAGCGTGTCATCC
         CTCG CAGCT GT TT CG CC GAGGTTTT TGGAATCA CC AT CA CGTGT AT C
-MEXICO  CTCGGCAGCTGGTGTTTCGTCCTGAGGTTTTTTGGAATCACCCGATTCAACGTGTTATAC 250v        260v        270v        280v        290v        300v
-BURMA   ATAACGAGCTGGAGCTTTACTGCCGCGCCCGCTCCGGCCGCTGTCTTGAAATTGGCGCCC
         ATAA GAGCT GAGC  TA TGCCG GC CGCTC GG CGCTG CTTGA ATTGG GCCC
-MEXICO  ATAATGAGCTTGAGCAGTATTGCCGTGCTCGCTCGGGTCGCTGCCTTGAGATTGGAGCCC 310v        320v        330v        340v        350v        360v
-BURMA   ATCCCCGCTCAATAAATGATAATCCTAATGTGGTCCACCGCTGCTTCCTCCGCCCTGTTG
         A CC CGCTC AT AATGATAATCCTAATGT TCCA CGCTGCTT CTCC CCC GT G
-MEXICO  ACCCACGCTCCATTAATGATAATCCTAATGTCCTCCATCGCTGCTTTCTCCACCCCGTCG
```

```
              370v        380v       390v        400v        410v        420v
-BURMA  GGCGTGATGTTCAGCGCTGGTATACTGCTCCCACTCGCGGGCCGGCTGCTAATTGCCGGC
        G CG GATGTTCAGCGCTGGTA AC GC CC ACT G GG CC GC GC AA TG CG C
-MEXICO GCCGGGATGTTCAGCGCTGGTACACAGCCCCGACTAGGGGACCTGCGGCGAACTGTCGCC 430v        440v       450v        460v        470v        480v
-BURMA  GTTCCGCGCTGCGCGGGCTTCCCGCTGCTGACCGCACTTACTGCCTCGACGGGTTTTCTG
        G TC GC CT CG GG CT CC   C GC GACCGCACTTACTG  T GA GG TTT  C G
-MEXICO GCTCGGCACTTCGTGGTCTGCCACCAGCCGACCGCACTTACTGTTTTTGATGGCTTTGCCG 490v        500v       510v        520v        530v        540v
-BURMA  GCTGTAACTTTCCCGCCGAGACTGGCATCGCCCTCTACTCCCTTCATGATATGTCACCAT
        GCTG    TTT CCGCCGAGACTGG  T GC CTCTA TC CT CATGA TG   CC
-MEXICO GCTGCCGTTTTGCCGCCGAGACTGGTGTGGCTCTCTATTCTCTCCATGACTTGCAGCCGG 550v        560v       570v        580v        590v        600v
-BURMA  CTGATGTCGCCGAGGCCATGTTCCGCCATGGTATGACGCGGCTCTATGCCGCCTCCATC
        CTGATGT GCCGAGGC ATG   CGCCA GG ATGAC CG CT TATGC GC   TCCA
-MEXICO CTGATGTTGCCGAGGCGATGGCTCGCCACGGCATGACCCGCCTTTATGCAGCTTTCCACT 610v        620v       630v        640v        650v        660v
-BURMA  TTCCGCCTGAGGTCCTGCTGCCCCCTGGCACATATCGCACCGCATCGTATTTGCTAATTC
        T CC CC GAGGT CT CTGCC CCTGGCAC TA CG AC   CATC TA TTGCT AT C
-MEXICO TGCCTCCAGAGGTGCTCCTGCCTCCTGGCACCTACCGGACATCATCCTACTTGCTGATCC 670v        680v       690v        700v        710v        720v
-BURMA  ATGACGGTAGGCGCGTTGTGGTGACGTATGAGGGTGATACTAGTGCTGGTTACAACCACG
        A GA GGTA GCGCG   GT GT AC TATGAGGGTGA ACTAG GC GGTTACAA CA G
-MEXICO ACGATGGTAAGCGCGCGGTTGTCACTTATGAGGGTGACACTAGCGCCGGTTACAATCATG 730v        740v       750v        760v        770v        780v
-BURMA  ATGTCTCCAACTTGCGCTCCTGGATTAGAACCACCAAGGTTACCGGAGACCATCCCCTCG
        ATGT  CCA C T CGC C TGGAT AG AC AC AAGGTT    GG GA CA CC  T G
-MEXICO ATGTTGCCACCCTCCGCACATGGATCAGGACAACTAAGGTTGTGGGTGAACACCCTTTGG 790v        800v       810v        820v        830v        840v
-BURMA  TTATCGAGCGGGTTAGGGCCATTGGCTGCCACTTTGTTCTCTTGCTCACGGCAGCCCCGG
        T ATCGAGCGGGT  GGG  ATTGGCTG CACTTTGT  T TTG TCAC GC GCCCC G
-MEXICO TGATCGAGCGGGTGCGGGGTATTGGCTGTCACTTTGTGTTGTTGATCACTGCGGCCCCTG 850v        860v       870v        880v        890v        900v
-BURMA  AGCCATCACCTATGCCTTATGTTCCTTACCCCCGGTCTACCGAGGTCTATGTCCGATCGA
        AGCC TC CC ATGCC TA GTTCCTTACCC CG TC AC GAGGTCTATGTCCG TC A
-MEXICO AGCCCTCCCCGATGCCCTACGTTCCTTACCCGCGTTCGACGGAGGTCTATGTCCGGTCTA 910v        920v       930v        940v        950v        960v
-BURMA  TCTTCGGCCCGGGTGGCACCCCTTCCTTATTCCCAACCTCATGCTCCACTAAGTCGACCT
        TCTT GG CC GG GG  CCCC TC T TTCCC ACC C TG  C     AAGTC AC T
-MEXICO TCTTTGGGCCCGGCGGGTCCCCGTCGCTGTTCCCGACCGCTTGTGCTGTCAAGTCCACTT 970v        980        990v        1000v       1010v       1020v
-BURMA  TCCATGCTGTCCCTGCCCATATTTGGGACCGTCTTATGCTGTTCGGGGCCACCTTGGATG
        T CA GC GTCCC  C CA AT TGGGACCGTCT ATGCT TT GGGGCCACC T GA G
-MEXICO TTCACGCCGTCCCCACGCACATCTGGGACCGTCTCATGCTCTTTGGGGCCACCCTCGACG 1030v       1040v      1050v       1060v       1070v       1080v
-BURMA  ACCAAGCCTTTTGCTGCTCCCGTTTAATGACCTACCTTCGCGGCATTAGCTACAAGGTCA
        ACCA GCCTTTTGCTGCTCC G  T ATGAC TACCTTCG GGCATTAGCTA AAGGT A
-MEXICO ACCAGGCCTTTTGCTGCTCCAGGCTTATGACGTACCTTCGTGGCATTAGCTATAAGGTAA 1090v       1100v      1110v       1120v       1130v       1140v
-BURMA  CTGTTGGTACCCTTGTGGCTAATGAAGGCTGGAATGCCTCTGAGGACGCCCTCACAGCTG
        CTGT GGT CCCT GT GCTAATGAAGGCTGGAATGCC C GAGGA GC CTCAC GC G
-MEXICO CTGTGGGTGCCCTGGTCGCTAATGAAGGCTGGAATGCCACCGAGGATGCGCTCACTGCAG 1150v       1160v      1170v       1180v       1190v       1200v
-BURMA  TTATCACTGCCGCCTACCTTACCATTTGCCACCAGCGGTATCTCCGCACCCAGGCTATAT
        TTAT AC GC GC TACCT AC AT TG CA CAGCG TAT T  CG ACCCAGGC AT T
-MEXICO TTATTACGGCGGCTTACCTCACAATATGTCATCAGCGTTATTTGCGGACCCAGGCGATTT 1210v       1220v      1230v       1240v       1250v       1260v
-BURMA  CCAAGGGGATGCGTCGTCTGGAACGGGAGCATGCCCAGAAGTTTATAACACGCCTCTACA
        C AAGGG ATGCG CG CT GA C  GA CATGC CAGAA TTTAT  CACGCCTCTACA
-MEXICO CTAAGGGCATGCGCCGGCTTGAGCTTGAACATGCTCAGAAATTTATTTCACGCCTCTACA
```

9

-continued

```
                   1270v      1280v      1290v      1300v      1310v      1320v
-BURMA    GCTGGCTCTTCGAGAAGTCCGGCCGTGATTACATCCCTGGCCGTCAGTTGGAGTTCTACG
          GCTGGCT TT GAGAAGTC GG CGTGATTACATCCC GGCCG CAG TG AGTTCTACG

-MEXICO   GCTGGCTATTTGAGAAGTCAGGTCGTGATTACATCCCAGGCCGCCAGCTGCAGTTCTACG 1330v      1340v      1350v      1360v      1370v      1380v
-BURMA    CCCAGTGCAGGCGCTGGCTCTCCGCCGGCTTTCATCTTGATCCACGGGTGTTGGTTTTTG
          C CAGTGC G CGCTGG T TC GCCGG TT CATCT GA CC CG    TT GTTTTTG

-MEXICO   CTCAGTGCCGCCGCTGGTTATCTGCCGGGTTCCATCTCGACCCCCGCACCTTAGTTTTTG 1390v      1400v      1410v      1420v      1430v      1440v
-BURMA    ACGAGTCGGCCCCCTGCCATTGTAGGACCGCGATCCGTAAGGCGCTCTCAAAGTTTTGCT
          A GAGTC G  CC TG    TG  G ACC C ATCCG   G        AAA TTTTGCT

-MEXICO   ATGAGTCAGTGCCTTGTAGCTGCCGAACCACCATCCGGCGGATCGCTGGAAAATTTTGCT 1450v      1460v      1470v      1480v      1490v      1500v
-BURMA    GCTTCATGAAGTGGCTTGGTCAGGAGTGCACCTGCTTCCTTCAGCCTGCAGAAGGCGCCG
          G TT ATGAAGTGGCT GGTCAGGAGTG  C TG TTCCT CAGCC GC GA GG      G

-MEXICO   GTTTTATGAAGTGGCTCGGTCAGGAGTGTTCTTGTTTCCTCCAGCCCGCCGAGGGGCTGG 1510v      1520v      1530v      1540v      1550v      1560v
-BURMA    TCGGCGACCAGGGTCATGATAATGAAGCCTATGAGGGGTCCGATGTTGACCCTGCTGAGT
             GGCGACCA GGTCATGA AATGA GCCTATGA GG TC GATGTTGA  CTGCTGAG

-MEXICO   CGGGCGACCAAGGTCATGACAATGAGGCCTATGAAGGCTCTGATGTTGATACTGCTGAGC 1570v      1580v      1590v      1600v      1610v      1620v
-BURMA    CCGCCATTAGTGACATATCTGGGTCCTATGTCGTCCCTGGCACTGCCCTCCAACCGCTCT
          C GCCA       GACAT  C GG TC TA  TCGT     TGG     C CT CAA C  TCT

-MEXICO   CTGCCACCCTAGACATTACAGGCTCATACATCGTGGATGGTCGGTCTCTGCAAACTGTCT 1630v      1640v      1650v      1660v      1670v      1680v
-BURMA    ACCAGGCCCTCGATCTCCCCGCTGAGATTGTGGCTCGCGCGGGCCGGCTGACCGCCACAG
          A CA GC CTCGA CT CC GCTGA  T GT GCTCGCGC G CCG CTG C GC ACAG

-MEXICO   ATCAAGCTCTCGACCTGCCAGCTGACCTGGTAGCTCGCGCAGCCCGACTGTCTGCTACAG 1690v      1700v      1710v      1720v      1730v      1740v
-BURMA    TAAAGGTCTCCCCAGGTCGATGGGCGGATCGATTGCGAGACCCTTCTTGGTAACAAAACCT
          T A  GT  C  A   C  TGG CG  T GATTGC A AC    T  T GG AA AA AC T

-MEXICO   TTACTGTTACTGAAACCTCTGGCCGTCTGGATTGCCAAACAATGATCGGCAATAAGACTT 1750v      1760v      1770v      1780v      1790v      1800v
-BURMA    TTCGCACGTCGTTCGTTGACGGGGCGGTCTTAGAGACCAATGGCCCAGAGCGCCACAATC
          TTC CAC  C TT GTTGA GGGGC   C T GAG    AA GG CC GAGC   C  AA C

-MEXICO   TTCTCACTACCTTTGTTGATGGGGCACGCCTTGAGGTTAACGGGCCTGAGCAGCTTAACC 1810v      1820v      1830v      1840v      1850v      1860v
-BURMA    TCTCCTTCGATGCCAGTCAGAGCACTATGGCCGCTGGCCCTTTCAGTCTCACCTATGCCG
          TCTC TT GA  C    CAG G A TATGGC GC GGCCC TT  G CTCACCTATGC G

-MEXICO   TCTCTTTTGACAGCCAGCAGTGTAGTATGGCAGCCGGCCCGTTTTGCCTCACCTATGCTG 1870v      1880v      1890v      1900v      1910v      1920v
-BURMA    CCTCTGCAGCTGGGCTGGAGGTGCGCTATGTTGCTGCCGGGCTTGACCATCGGGCGGTTT
          CC   G  G   GGGCTGGA GT C  T T    C GC GG CT GA    CG G  GTTT

-MEXICO   CCGTAGATGGCGGGCTGGAAGTTCATTTTTCCACCGCTGGCCTCGAGAGCCGTGTTGTTT 1930v      1940v      1950v      1960v      1970v      1980v
-BURMA    TTGCCCCCGGTGTTTCACCCCGGTCAGCCCCCGGCGAGGTTACCGCCTTCTGCTCTGCCC
          T  CCCC GGT  T C CC       C  CC  G GAGGT ACCGCCTTCTGCTC GC C

-MEXICO   TCCCCCCTGGTAATGCCCCGACTGCCCCGCCGAGTGAGGTCACCGCCTTCTGCTCAGCTC
```

```
                  1990v      2000v      2010v      2020v      2030v      2040v
-BURMA  TATACAGGTTTAACCGTGAGGCCCAGCGCCATTCGCTGATCGGTAACTTATGGTTCCATC
        T  TA AGG      AACCG   AG   CCAGCGCCA TCG T AT GGTA   TT TGG T CA C

-MEXICO TTTATAGGCACAACCGGCAGAGCCAGCGCCAGTCGGTTATTGGTAGTTTGTGGCTGCACC 2050v      2060v      2070v      2080v      2090v      2100v
-BURMA  CTGAGGGACTCATTGGCCTCTTCGCCCCGTTTTCGCCCGGGCATGTTTGGGAGTCGGCTA
        CTGA GG   T  T  GGCCT TTC C  CC TTTTC  CCCGGGCATG   TGG  GTC GCTA

-MEXICO CTGAAGGTTTGCTCGGCCTGTTCCCGCCCTTTTCACCCGGGCATGAGTGGCGGTCTGCTA 2110v      2120v      2130v      2140v      2150v      2160v
-BURMA  ATCCATTCTGTGGCGAGAGCACACTTTTACACCCGTACTTGGTCGGAGGTTGATGCCGTCT
        A  CCATT TG  GGCGAGAGCAC  CT TACACCCG ACTTGGTC       TT   G C

-MEXICO ACCCATTTTGCGGCGAGAGCACGCTCTACACCCGCACTTGGTCCACAATTACAGACACAC 2170v      2180v      2190v      2200v      2210v      2220v
-BURMA  CTAGTCCAGCCCGGCCTGACTTAGGTTTTATGTCTGAGCCTTCTATACCTAGTAGGGCCG
        C       CG C GGC      T   GGT  T TG  TG    CT C       C   G  GG C

-MEXICO CCTTAACTGTCGGGCTAATTTCCGGTCATTTGGATGCTGCTCCCCACTCGGGGGGGCCAC 2230v      2240v      2250v      2260v      2270v      2280v
-BURMA  CCACGCCTACCCTGGCGGCCCCTCTACCCCCCCTGCACCGGACCCTTCCCCCCCTCCCT
        C  C  CT CC    G   C  CT TA  C C  CTG    C          C    CCC C

-MEXICO CTGCTACTGCCACAGGCCCTGCTGTAGGCTCGTCTGACTCTCCAGACCCTGACCCGCTAC 2290v      2300v      2310v      2320v      2330v      2340v
-BURMA  CTGCCCCGGCGCTTGCTGAGCCGGCTTCTGGCGCTACCGCCGGGGCCCCGGCCATAACTC
        CTG     C  TG     C   C TCTGG GC      C G  G CCC    C    A T

-MEXICO CTGATGTTACAGATGGCTCACGCCCTCTGGGGCCCGTCCGGCTGGCCCCAACCCGAATG 2350v      2360v      2370v      2380v      2390v      2400v
-BURMA  ACCAGACGGCCCGGCACCGCCGCCTGCTCTTCACCTACCCGGATGGCTCTAAGGTATTCG
        C   CG         CGCCGC T CT      CACCTACCC GA GGC CTAAG T T   G
-MEXICO GCGTTCCGCAG----------- CGCCGCTTACTACACACCTACCCTGACGGCGCTAAGATCTATG 2410v      2420v      2430v      2440v      2450v      2460v
-BURMA  CCGGCTCGCTGTTCGAGTCGACATGCACGTGGCTCGTTAACGCGTCTAATGTTGACCACC
        CGGCTC   T   TTCGAGTC        TGCAC TGGCT GT  AACGC TCTAA G   G CCACC
-MEXICO TCGGCTCCATTTTCGAGTCTGAGTGCACCTGGCTTGTCAACGCATCTAACGCCGGCCACC 2470v      2480v      2490v      2500v      2510v      2520v
-BURMA  GCCCTGGCGGCGGGCTTTGCCATGCATTTTACCAAAGGTACCCCGCCTCCTTTGTGCTG
        GCCCTGG  GGCGGGCTTTG  CATGC TTTT   CA  G TACCC G   TC TTTGA GC
-MEXICO GCCCTGGTGGCGGGCTTTGTCATGCTTTTTTTCAGCGTTACCCTGATTCGTTTGACGCCA 2530v      2540v      2550v      2560v      2570v      2580v
-BURMA  CCTCTTTTGTGATGCGCGACGGCGCGGCCGCGTACACACTAACCCCCCGGCCAATAATTC
        CC   TTTGTGATGCG  GA GG      GCCGCGTA AC CT AC CCCCGGCC AT ATTC
-MEXICO CCAAGTTTGTGATGCGTGATGGTCTTGCCGCGTATACCCTTACACCCCGGCCGATCATTC 2590v      2600v      2610v      2620v      2630v      2640v
-BURMA  ACGCTGTCGCCCCTGATTATAGGTTGGAACATAACCCAAAGAGGCTTGAGGCTGCTTATC
        A  GC GT GCCCC  GA TAT G TTGGAACATAACCC AAGAGGCT GAGGCTGC TA C
-MEXICO ATGCGGTGGCCCCGGACTATCGATTGGAACATAACCCCAAGAGGCTCGAGGCTGCCTACC 2650v      2660v      2670v      2680v      2690v      2700v
-BURMA  GGGAAACTTGCTCCCGCCTCGGCGCACCGCTGCATACCCGCTCCTCGGGACCGGCATATACC
        G GA  ACTTGC  CCCGCC   GGCAC GCTGC TA CC CTC T GG   C GGCAT TACC
-MEXICO GCGAGACTTGCGCCCGCCGAGGCACTGCTGCCTATCCACTCTTAGGCGCTGGCATTTACC 2710v      2720v      2730v      2740v      2750v      2760v
-BURMA  AGGTGCCGATCGGCCCCAGTTTTGACGCCTGGGACGCGGAACCACCGCCCCGGGGATGAGT
        AGGTGCC   T   G     AGTTTTGA  GCCTGGGAGCGGAACCACCGCCC    GA GAG
-MEXICO AGGTGCCTGTTAGTTTGAGTTTTGATGCCTGGGAGCGGAACCACCGCCCGTTTGACGAGC 2770v      2780v      2790v      2800v      2810v      2820v
-BURMA  TGTACCTTCCTGAGCTTGCTGCCAGATGGTTTGAGGCCAATAGGCCGACCCGCCCGACTC
        T  TACCT  C  GAGCT GC GC   G TGGTTTGA  CCAA  G CC     C  CC AC
-MEXICO TTTACCTAACAGAGCTGGCGGCTCGGTGGTTTGAATCCAACCGCCCCGGTCAGCCCACGT
```

-continued

```
              2830v      2840v      2850v      2860v      2870v      2880v
-BURMA   TCACTATAACTGAGGATGTTGCACGGACAGCGAATCTGGCCATCGAGCTTGACTCAGCCA
         T A  ATAACTGAGGAT   GC CG  C GC AA CTGGCC T GAGCTTGACTC G  A
-MEXICO  TGAACATAACTGAGGATACCGCCCGTGCGGCCAACCTGGCCCTGGAGCTTGACTCCGGGA 2890v      2900v      2910v      2920v      2930v      2940v
-BURMA   CAGATGTCGGCCGGGCCTGTGCCGGCTGTCGGGTCACCCCCGGCGTTGTTCAGTACCAGT
             GA GT GGCCG GC TGTGCCGG TGT    GTC    CC GGCGTTGT C GTA CAGT
-MEXICO  GTGAAGTAGGCCGCGCATGTGCCGGGTGTAAAGTCGAGCCTGGCGTTGTGCGGTATCAGT 2950v      2960v      2970v      2980v      2990v      3000v
-BURMA   TTACTGCAGGTGTGCCTGGATCCGGCAAGTCCCGCTCTATCACCCAAGCCGATGTGGACG
         TTAC GC GGTGT CC GG TC GGCAAGTC      TC T    CA GC GATGTGGA G
-MEXICO  TTACAGCCGGTGTCCCCGGCTCTGGCAAGTCAAAGTCCGTGCAACAGGCGGATGTGGATG 3010v      3020v      3030v      3040v      3050v      3060v
-BURMA   TTGTCGTGGTCCCGACGCGTGAGTTGCGTAATGCCTGGCGCCGTCGCGGCTTTGCTGCTT
         TTGT GT GT CC AC CG GAG T CG AA GC TGGCG CG CG GGCTTTGC GC T
-MEXICO  TTGTTGTTGTGCCCACTCGCGAGCTTCGGAACGCTTGGCGGCGCCGGGGCTTTGCGGCAT 3070v      3080v      3090v      3100v      3110v      3120v
-BURMA   TTACCCCGCATACTGCCGCCAGAGTCACCCAGGGGCGCCGGGTTGTCATTGATGAGGCTC
         T AC CCGCA ACTGC GCC G GTCAC    GG CG   GGGTTGTCATTGATGAGGC C

-MEXICO  TCACTCCGCACACTGCGGCCCGTGTCACTAGCGGCCGTAGGGTTGTCATTGATGAGGCCC 3130v      3140v      3150v      3160v      3170v      3180v
-BURMA   CATCCCTCCCCCCTCACCTGCTGCTGCTCCACATGCAGCGGGCCGCCACCGTCCACCTTC
         C TC CTCCCCCC CAC TGCTGCT  T CA ATGCAGCG GC GC  C GT CACCT C

-MEXICO  CTTCGCTCCCCCCACACTTGCTGCTTTTACATATGCAGCGTGCTGCATCTGTGCACCTCC 3190v      3200v      3210v      3220v      3230v      3240v
-BURMA   TTGGCGACCCCGAACCAGATCCCAGCCATCGACTTTGAGCACGCTGGGCTCGTCCCCGCCA
         TTGG GACCCCGAA CAGATCCC GCCAT GA TTTGAGCAC C GG CT  T CC GC A
-MEXICO  TTGGGGACCCCGAATCAGATCCCCGCCATAGATTTTGAGCACACCGGTCTGATTCCAGCAA 3250v      3260v      3270v      3280v      3290v      3300v
-BURMA   TCAGGCCCGACTTAGGCCCCACCTCCTGGTGGCATGTTACCCATCGCTGGCCTGCGGATG
         T   GGCC GA TT G CCC AC TC TGGTGGCATGT ACCCA CG TG CCTGC GATG
-MEXICO  TACGGCCGGAGTTGGTCCCGACTTCATGGTGGCATGTCACCCACCGTTGCCCTGCAGATG 3310v      3320v      3330v      3340v      3350v      3360v
-BURMA   TATGCGAGCTCATCCGTGGTGCATACCCCATGATCCAGACCATAGCCGGGTTCTCCGTT
         T TG GAG T   TCCGTGGTGC TACCC A  ATCCAGAC AC AG   GGT CTCCGTT
-MEXICO  TCTGTGAGTTAGTCCGTGGTGCTTACCCTAAAATCCAGACTACAAGTAAGGTGCTCCGTT 3370v      3380v      3390v      3400v      3410v      3420v
-BURMA   CGTTGTTCTGGGGTGAGCCTGCCGTCGGGCAGAAACTAGTGTTCACCCAGGCGGCCAAGC
         C  T TTCTGGGG GAGCC GC GTCGG CAGAA CTAGTGTTCAC CAGGC GC AAG
-MEXICO  CCCTTTTCTGGGGAGAGCCAGCTGTCGGCCAGAAGCTAGTGTTCACACAGGCTGCTAAGG 3430v      3440v      3450v      3460v      3470v      3480v
-BURMA   CCGCCAACCCCGGCTCAGTGACGGTCCACGAGGCGCAGGGCGCTACCTACACGGAGACCA
         CCGC   ACCCCGG  TC T ACGGTCCA GAGGC CAGGG GC AC T  AC    AC A
-MEXICO  CCGCGCACCCCGGATCTATAACGGTCCATGAGGCCCAGGGTGCCACTTTTACCACTACAA 3490v      3500v      3510v      3520v      3530v      3540v
-BURMA   CTATTATTGCCACAGCAGATGCCCGGGGCCTTATTCAGTCGTCTCGGGCTCATGCATTG
         CTAT ATTGC AC GCAGATGCCCG GGCCT AT CAGTC TC CGGGCTCA GC AT G
-MEXICO  CTATAATTGCAACTGCAGATGCCCGTGGCCTCATACAGTCCTCCCGGGCTCACGCTATAG 3550v      3560v      3570v      3580v      3590v      3600v
-BURMA   TTGCTCTGACGCGCCACACTGAGAAGTGCGTCATCATTGACGCACCAGGCCTGCTTCGCG
         TTGCTCT AC  G CA ACTGA AA TG GT AT  TTGAC C CC GGCCTG T CG G
-MEXICO  TTGCTCTCACTAGGCATACTGAAAAATGTGTTATACTTGACTCTCCCGGCCTGTTGCGTG 3610v      3620v      3630v      3640v      3650v      3660v
-BURMA   AGGTGGGCATCTCCGATGCAATCGTTAATAACTTTTTCCTCGCTGGTGGCGAAATTGGTC
         AGGTGGG ATCTC GATGC AT GTTAATAA TT TTCCT  C GGTGGCGA  TTGGTC
-MEXICO  AGGTGGGTATCTCAGATGCCATTGTTAATAATTTCTTCCTTTCGGGTGGCGAGGTTGGTC 3670v      3680v      3690v      3700v      3710v      3720v
-BURMA   ACCAGCGCCCATCAGTTATTCCCCGTGGCAACCCTGACGCCAATGTTGACACCCTGGCTG
         ACCAG G  CCATC GT ATTCC CG GGCAACCCTGAC  CAATGTTGAC   CT GC G
-MEXICO  ACCAGAGACCATCGGTCATTCCGCGAGGCAACCCTGACCGCAATGTTGACGTGCTTGCGG 3730v      3740v      3750v      3760v      3770v      3780v
-BURMA   CCTTCCCGCCGTCTTGCCAGATTAGTGCCTTCCATCAGTTGGCTGAGGAGCTTGGCCACA
         C  TT CC CC TC TGCCA AT AG GCCTTCCATCAG T GCTGAGGAGCT GGCCAC
-MEXICO  CGTTTCCACCTTCATGCCAAATAAGCGCCTTCCATCAGCTTGCTGAGGAGCTGGGCCACC
```

```
              3790v      3800v     3810v      3820v      3830v      3840v
-BURMA     GACCTGTCCCTGTTGCAGCTGTTCTACCACCCTGCCCCGAGCTCGAACAGGGCCTTCTCT
             G CC  G     CC GT GC GCTGT CTACC  CCCTGCCC GAGCT  GA  CAGGGCCTTCTCT
-MEXICO    GGCCGGCGCCGGTGGCGGCTGTGCTACCTCCCTGCCCTGAGCTTGAGCAGGGCCTTCTCT 3850v      3860v     3870v      3880v      3890v      3900v
-BURMA     ACCTGCCCCAGGAGCTCACCACCTGTGATAGTGTCGTAACATTTGAATTAACAGACATTG
             A  CTGCC CAGGAGCT    CC CCTGTGA AGTGT GT  ACATTTGA   TAAC GACATTG
-MEXICO    ATCTGCCACAGGAGCTAGCCTCCTGTGACAGTGTTGTGACATTTGAGCTAACTGACATTG 3910v      3920v     3930v      3940v      3950v      3960v
-BURMA     TGCACTGCCGCATGGCCGCCCCGAGCCAGCGCAAGGCCGTGCTGTCCACACTCGTGGGCC
             TGCACTGCCGCATGGC GCCCC AGCCA     G AA GC GT    TGTCCAC CT GT GGCC
-MEXICO    TGCACTGCCGCATGGCGGCCCCTAGCCAAAGGAAAGCTGTTTTGTCCACGCTGGTAGGCC 3970v      3980v     3990v      4000v      4010v     4020v
-BURMA     GCTACGGCGGTCGCACAAAGCTCTACAATGCTTCCCACTCTGATGTTCGCGACTCTCTCG
             G TA GGC G  CGCACAA GCT TA  ATGC       CAC C GATGT CGCG CTC CT G
-MEXICO    GGTATGGCAGACGCSCSSGGCTTTATGATGCGGGTCACACCGATGTCCGCGCCTCCCTTG 4030v      4040v     4050v      4060v      4070v      4080v
-TASHKENT                              GGCCCCGTACAGGTCACAACCTGTGAGTTGTACGAGCTAG
                                       GGCCCCGTACAGGT ACAAC TGTGA TTGTACGAGCTAG
-BURMA     CCCGTTTTATCCCGGCCATTGGCCCCGTACAGGTTACAACTTGTGAATTGTACGAGCTAG
             C CG TTTAT CC  C  T GG C   GT     G   AC AC TGTGAA T T  GAGCT G
-MEXICO    CGCGCTTTATTCCCACTCTCGGGCGGGTTACTGCCACCACCTGTGAACTCTTTGAGCTTG 4090v      4100v     4110v      4120v      4130v      4140v
-TASHKENT  TGGAGGCCATGGTCGAGAAAGGCCAGGATGGCTCCGCCGTCCTTGAGCTCGATCTCTGCA
           TGGAGGCCATGGTCGAGAA GGCCAGGATGGCTCCGCCGTCCTTGAGCT GATCT TGCA
-BURMA     TGGAGGCCATGGTCGAGAAGGGCCAGGATGGCTCCGCCGTCCTTGAGCTTGATCTTTGCA
             T GAGGC ATGGT GAGAAGGGCCA GA GG TC GCCGTCCT GAG T GAT T TGCA
-MEXICO    TAGAGGCGATGGTGGAGAAGGGCCAAGACGGTTCAGCCGTCCTCGAGTTGGATTTGTGCA 4150v      4160v     4170v      4180v      4190v      4200v
-TASHKENT  ACCGTGACGTGTCCAGGATCACCTTTTTCCAGAAAGATTGCAATAAGTTCACCACGGGAG
           ACCGTGACGTGTCCAGGATCACCTT TTCCAGAAAGATTG AA AAGTTCACCAC GG G
-BURMA     ACCGTGACGTGTCCAGGATCACCTTCTTCCAGAAAGATTGTAACAAGTTCACCACAGGTG
             CCG GA GT TCC G AT ACCTT TTCCAGAA GATTGTAACAAGTTCAC AC GG G
-MEXICO    GCCGAGATGTCTCCCGCATAACCTTTTTCCAGAAGGATTGTAACAAGTTCACGACCGGCG 4210v      4220v     4230v      4240v      4250v      4260v
-TASHKENT  AGACCATCGCCCATGGTAAAGTGGGCCAGGGCATTTCGGCCTGGAGTAAGACCTTCTGTG
           AGACCAT GCCCATGGTAAAGTGGGCCAGGGCATTTCGGCCTGGAG AAGACCTTCTG G
-BURMA     AGACCATTGCCCATGGTAAAGTGGGCCAGGGCATCTCGGCCTGGAGCAAGACCTTCTGCG
             AGAC ATTGC CATGG AAAGT GG CAGGG ATCT    CTGGAG AAGAC TT TG G
-MEXICO    AGACAATTGCGCATGGCAAAGTCGGTCAGGGTATCTTCCGCTGGAGTAAGACGTTTGTG 4270v      4280v     4290v      4300v      4310v      4320v
-TASHKENT  CCCTTTTCGGCCCCTGGTTCCGTGCTATTCCGTGGGCTATTCTGGCCCTGCTCCCTCAGG
           CCCT TT GGCCC TGGTTCCG GCTATTGAGAAGGCTATTCTGGCCCTGCTCCCTCAGG
-BURMA     CCCTCTTTGGCCCTTGGTTCCGCGCTATTGAGAAGGCTATTCTGGCCCTGCTCCCTCAGG
             CCCT TTTGGCCC TGGTTCCG GC ATTGAGAAGGCTATTCT    CCCT T CC CA G
-MEXICO    CCCTGTTTGGCCCCTGGTTCCGTGCGATTGAGAAGGCTATTCTATCCCTTTTACCACAAG 4330v      4340v     4350v      4360v      4370v      4380v
-TASHKENT  GTGTGTTTTATGGGGATGCCTTTGATGACACCGTCTTCTCGGCGCGTGTGGCCGCAGCAA
           GTGTGTTTTA GG GATGCCTTTGATGACACCGTCTTCTCGGCG  TGTGGCCGCAGCAA
-BURMA     GTGTGTTTTACGGTGATGCCTTTGATGACACCGTCTTCTCGGCGGCTGTGGCCGCAGCAA
             TGTGTT TACGG GATGC T TGA GAC C GT TTCTC GC GC GTGGC G  GC A
-MEXICO    CTGTGTTCTACGGGGATGCTTATGACGACTCAGTATTCTCTGCTGCCGTGGCTGGCGCCA 4390v      4400v     4410v      4420v      4430v      4440v
-TASHKENT  AGGCGTCCATGGTGTTTGAGAATGACTTTTCTGAGTTTGACTCCACCCAGAATAATTTTT
           AGGC TCCATGGTGTTTGAGAATGACTTTTCTGAGTTTGACTCCACCCAGAATAA TTTT
-BURMA     AGGCATCCATGGTGTTTGAGAATGACTTTTCTGAGTTTGACTCCACCCAGAATAACTTTT
                CCATGGTGTTTGA AATGA TTTTCTGAGTTTGACTC AC CAGAATAACTTTT
-MEXICO    GCCATGCCATGGTGTTTGAAAATGATTTTTCTGAGTTTGACTCGACTCAGAATAACTTTT
```

-continued

```
              4450v      4460v      4470v      4480v      4490v      4500v
-TASHKENT  CCCTGGGCCTAGAGTGTGCTATTATGGAGAAGTGTGGGATGCCGAAGTGGCTCATCCGCT
           C CTGGG CTAGAGTGTGCTATTATGGAG AGTGTGGGATGCCG AGTGGCTCATCCGC

-BURMA     CTCTGGGTCTAGAGTGTGCTATTATGGAGGAGTGTGGGATGCCGCAGTGGCTCATCCGCC
           C CT GGTCT GAGTG GC ATTATGGA GAGTGTGG ATGCC CAGTGGCT   TC G

-MEXICO    CCCTAGGTCTTGAGTGCGCCATTATGGAAGAGTGTGGTATGCCCCAGTGGCTTGTCAGGT 4510v      4520v      4530v      4540v      4550v      4560v
-TASHKENT  TGTACCACCTTATAAGGTCTGCGTGGATCCTGCAGGCCCCGAAGGAGTCCCTGCGAGGGT
           TGTA CACCTTATAAGGTCTGCGTGGATC TGCAGGCCCCGAAGGAGTC CTGCGAGGGT

-BURMA     TGTATCACCTTATAAGGTCTGCGTGGATCTTGCAGGCCCCGAAGGAGTCTCTGCGAGGGT
           TGTA CA    T  GGTC GCGTGGATC TGCAGGCCCC AA GAGTCT TG GAGGGT

-MEXICO    TGTACCATGCCGTCCGGTCGGCGTGGATCCTGCAGGCCCCAAAAGAGTCTTTGAGAGGGT 4570v      4580v      4590v      4600v      4610v      4620v
-TASHKENT  GTTGGAAGAAACACTCCGGTGAGCCCGGCACTCTTCTATGGAATACTGTCTGGAACATGG
           TTGGAAGAAACACTCCGGTGAGCCCGGCACTCTTCTATGGAATACTGTCTGGAA ATGG

-BURMA     TTTGGAAGAAACACTCCGGTGAGCCCGGCACTCTTCTATGGAATACTGTCTGGAATATGG
           T TGGAAGAA CA TC GGTGAGCC GGCA   T CT TGGAATAC GT TGGAA ATGG

-MEXICO    TCTGGAAGAAGCATTCTGGTGAGCCGGGCAGCTTGCTCTGGAATACGGTGTGGAACATGG 4630v      4640v      4650v      4660v      4670v      4680v
-TASKENT   CCGTTATCACCCATTGTTACGATTTCCGCGATTTGCAGGTGGCTGCCTTTAAAGGTGATG
           CCGTTAT ACCCA TGTTA GA TTCCGCGATTT  AGGTGGCTGCCTTTAAAGGTGATG

-BURMA     CCGTTATTACCCACTGTTATGACTTCCGCGATTTTCAGGTGGCTGCCTTTAAAGGTGATG
           C  T ATT CCCA TG TATGA TTCCG GA  T CAGGT GC GCCTT AA GG GA G

-MEXICO    CAATCATTGCCCATTGCTATGAGTTCCGGGACCTCCAGGTTGCCGCCTTCAAGGGCGACG 4690v      4700v      4710v      4720v      4730v      4740v
-TASHKENT  ATTCGATAGTGCTTTGCAGTGAGTACCGTCAGAGTCCAGGGGCTGTCCTGATTGCTG
           ATTCGATAGTGCTTTGCAGTGAGTA CGTCAGAGTCCAGG GCTGCTGTCCTGAT GC G
-BURMA     ATTCGATAGTGCTTTGCAGTGAGTATCGTCAGAGTCCAGGAGCTGCTGTCCTGATCGCCG
           A TCG T GT CT TG AGTGA TA CG CAGAG CCAGG GC G T   CT AT GC G
-MEXICO    ACTCGGTCGTCCTCTGTAGTGAATACCGCCAGAGCCCAGGCGCCGGTTCGCTTATAGCAG 4750v      4760v      4770v      4780v      4790v      4800v
-TASHKENT  GCTGTGGCTTAAAGCTGAAGGTGGGTTTCCGTCCGATTGGTTTGTATGCAGGTGTTGTGG
           GCTGTGGCTT AAG TGAAGGT G TTTCCG CCGAT GGTTTGTATGCAGGTGTTGTGG
-BURMA     GCTGTGGCTTGAAGTTGAAGGTAGATTTCCGCCCGATCGGTTTGTATGCAGGTGTTGTGG
           GCTGTGG TTGAAGTTGAAGG  GA TTCCG CCGAT GG TGTATGC GG GTTGT G
-MEXICO    GCTGTGGTTTGAAGTTGAAGGCTGACTTCCGGCCGATTGGGCTGTATGCCGGGGTTGTCG 4810v      4820v      4830v      4840v      4850v      4860v
-TASHKENT  TGACCCCCGGCCTTGGCGCGCTTCCCGACGTCGTGCGCTTGTCCGGCCGGCTTACTGAGA
           TG CCCCCGGCCTTGGCGCGCTTCCCGA GT GTGCGCTTG CCGGCCGGCTTAC GAGA
-BURMA     TGGCCCCCGGCCTTGGCGCGCTCCCTGATGTTGTGCGCTTCGCCGGCCGGCTTACCGAGA
           T GCCCC GG CT GG GC CT CC GATGT GT CG TTCGCCGG CGGCTT C GAGA
-MEXICO    TCGCCCGGGGCTCGGGGCCCTACCCGATGTCGTTCGATTCGCCGGACGGCTTTCGGAGA 4870v      4880v      4890v      4900v      4910v      4920v
-TASHKENT  AGAATTGGGGCCCTGGCCCTGAGCGGGCGGAGCAGCTCCGCCTTGCTGT
           AGAATTGGGGCCCTGGCCCTGAGCGGGCGGAGCAGCTCCGCCT GCTGT
-BURMA     AGAATTGGGGCCCTGGCCCTGAGCGGGCGGAGCAGCTCCGCCTCGCTGTTAGTGATTTCC
           AGAA TGGGG CCTG CC GAGCGGGC GAGCAGCTCCGCCTCGC GT      GATTTCC
-MEXICO    AGAACTGGGGGCCTGATCCGGAGCGGGCAGAGCAGCTCCGCCTCGCCGTGCAGGATTTCC 4930v      4940v      4950v      4960v      4970v      4980v
-BURMA     TCCGCAAGCTCACGAATGTAGCTCAGATGTGTGTGGATGTTGTTTCCCGTGTTTATGGGG
           TCCG A G T ACGAATGT GC CAGAT TGTGT GA GT GT TC  G GTTTA GGGG
-MEXICO    TCCGTAGGTTAACGAATGTGGCCCAGATTTGTGTTGGTGGTGTCTAGAGTTTACGGGG 4990v      5000v      5010v      5020v      5030v      5040v
-BURMA     TTTCCCCTGGACTCGTTCATAACCTGATTGGCATGCTACAGGCTGTTGCTGATGGCAAGG
           TTTCCCC GG CT GTTCATAACCTGAT GGCATGCT CAG CT TTG TGATGG AAGG
-MEXICO    TTTCCCCGGGTCTGGTTCATAACCTGATAGGCATGCTCCAGACTATTGGTGATGGTAAGG 5050v      5060v      5070v      5080v      5090v      5100v
-BURMA     CACATTTCACTGAGTCAGTAAAACCAGTGCTCGACTTGACAAATTCAATCTTGTGTCGGG
           C CATTT AC GAGTC GT AA CC  T CT GAC T ACA A TCAAT  TG   CGG
-MEXICO    CGCATTTTACAGAGTCTGTTAAGCCTATACTTGACCTTACACACTCAATTATGCACCGGT
```

-continued

```
              5110v      5120v      5130v      5140v      5150v      5160v
-BURMA   TGGAATGAATAACATGTCTTTTGCTGCGCCCATGGGTTCGCGACCATGCGCCCTCGGCCT
         GAATGAATAACATGT   TTTGCTGCGCCCATGGGTTCGC ACCATGCGCCCT GGCCT
-MEXICO  CTGAATGAATAACATGTGGTTTGCTGCGCCCATGGGTTCGCCACCATGCGCCCTAGGCCT 5170v      5180v      5190v      5200v      5210v      5220v
-BURMA   ATTTTGTTGCTGCTCCTCATGTTTTTGCCTATGCTGCCCGCGCCACCGCCCGGTCAGCCG
         TTTTG TG TG TCCTC TGTTT TGCCTATG TGCCCGCGCCACCG CCGGTCAGCCG
-MEXICO  CTTTTGCTGTTGTTCCTCTTGTTTCTGCCTATGTTGCCCGCGCCACCGACCGGTCAGCCG 5230v      5240v      5250v      5260v      5270v      5280v
-BURMA   TCTGGCCGCCGTCGTGGGCGGCGCAGCGGCGGTTCCGGCGGTGGTTTCTGGGGTGACCGG
         TCTGGCCGCCGTCGTGGGCGGCGCAGCGGCGGT CCGGCGGTGGTTTCTGGGGTGACCGG
-MEXICO  TCTGGCCGCCGTCGTGGGCGGCGCAGCGGCGGTACCGGCGGTGGTTTCTGGGGTGACCGG 5290v      5300v      5310v      5320v      5330v      5340v
-BURMA   GTTGATTCTCAGCCCTTCGCAATCCCCTATATTCATCCAACCAACCCCTTCGCCCCCGAT
         GTTGATTCTCAGCCCTTCGCAATCCCCTATATTCATCCAACCAACCCCTT GCCCC GA
-MEXICO  GTTGATTCTCAGCCCTTCGCAATCCCCTATATTCATCCAACCAACCCCTTTGCCCCAGAC 5350v      5360v      5370v      5380v      5390v      5400v
-BURMA   GTCACCGCTGCGGCCGGGGCTGGACCTCGTGTTCGCCAACCCGCCCGACCACTCGGCTCC
         GT   CCGCTGCG  CCGGG CTGGACCTCG TTCGCCAACC GCCCG CCACT GGCTCC
-MEXICO  GTTGCCGCTGCGTCCGGGTCTGGACCTCGCCTTCGCCAACCAGCCCGGCCACTTGGCTCC 5410v      5420v      5430v      5440v      5450v      5460v
-BURMA   GCTTGGCGTGACCAGGCCCAGCGCCCCGCCGTTGCCTCACGTCGTAGACCTACCACAGCT
         CTTGGCG GA CAGGCCCAGCGCCCC CCG TGCCTC CGTCG  GACCT CCACAGC
-MEXICO  ACTTGGCGAGATCAGGCCCAGCGCCCCTCCGCTGCCTCCCGTCGCCGACCTGCCACAGCC 5470v      5480v      5490v      5500v      5510v      5520v
-BURMA   GGGGCCGCGCCGCTAACCGCGGTCGCTCCGGCCCATGACACCCCGCCAGTGCCTGATGTC
         GGGGC GCG CGCT AC GC GT GC CC GCCCATGACACC C CC GT CC GA GT
-MEXICO  GGGGCTGCGGCGCTGACGGCTGTGGCGCCTGCCCATGACACCTCACCCGTCCCGGACGTT 5530v      5540v      5550v      5560v      5570v      5580v
-BURMA   GACTCCCGCGGCGCCATCTTGCGCCGGCAGTATAACCTATCAACATCTCCCCTTACCTCT
         GA TC CGCGG GC AT  T CGCCG CAGTATAA  T TC AC TC CCCCT AC TC
-MEXICO  GATTCTCGCGGTGCAATTCTACGCCGCCAGTATAATTTGTCTACTTCACCCCTGACATCC 5590v      5600v      5610v      5620v      5630v      5640v
-BURMA   TCCGTGGCCACCGGCACTAACCTGGTTCTTTATGCCGCCCCTCTTAGTCCGCTTTTACCC
         TC GTGGCC C GGCACTAA  T GT CT TATGC GCCCC CTTA TCCGC T T CC
-MEXICO  TCTGTGGCCTCTGGCACTAATTTAGTCCTGTATGCAGCCCCCCTTAATCCGCCTCTGCCG 5650v      5660v      5670v      5680v      5690v      5700v
-BURMA   CTTCAGGACGGCACCAATACCCATATAATGGCCACGGAAGCTTCTAATTATGCCCAGTAC
         CT CAGGACGG AC AATAC CA AT ATGGCCAC GA GC TC AATTATGC CAGTAC
-MEXICO  CTGCAGGACGGTACTAATACTCACATTATGGCCACAGAGGCCTCCAATTATGCACAGTAC 5710v      5720v      5730v      5740v      5750v      5760v
-BURMA   CGGGTTGCCCGTGCCACAATCCGTTACCGCCCGCCTGGTCCCCAATGCTGTCGGCGGTTAC
         CGGGTTGCCCG GC AC ATCCGTTACCG CC CT GT CC AATGC GT GG GG TA
-MEXICO  CGGGTTGCCCGCGCTACTATCCGTTACCGGCCCCTAGTGCCTAATGCAGTTGGAGGCTAT 5770v      5780v      5790v      5800v      5810v      5820v
-BURMA   GCCATCTCCATCTCATTCTGGCCACAGACCACCACCACCCCGACGTCCGTTGATATGAAT
         GC AT TCCAT TC TTCTGGCC CA AC ACCAC ACCCC AC TC GTTGA ATGAAT
-MEXICO  GCTATATCCATTTCTTTCTGGCCTCAAACAACCACAACCCCTACATCTGTTGACATGAAT 5830v      5840v      5850v      5860v      5870v      5880v
-BURMA   TCAATAACCTCGACGGATGTTCGTATTTTAGTCCAGCCCGGCATAGCCTCTGAGCTTGTG
         TC AT AC TC AC GATGT  G ATT T GT CA CC GGCATAGC TCTGA  T GT
-MEXICO  TCCATTACTTCCACTGATGTCAGGATTCTTGTTCAACCTGGCATAGCATCTGAATTGGTC 5890v      5900v      5910v      5920v      5930v      5940v
-BURMA   ATCCCAAGTGAGCGCCTACACTATCGTAACCAAGGCTGGCGCTCCGTCGAGACCTCTGGG
         ATCCCAAG GAGCGCCT CACTA CG AA CAAGG TGGCGCTC GT GAGAC TCTGG
-MEXICO  ATCCCAAGCGAGCGCCTTCACTACCGCAATCAAGGTTGGCGCTCGGTTGAGACATCTGGT 5950v      5960v      5970v      5980v      5990v      6000v
-BURMA   GTGGCTGAGGAGGAGGCTACCTCTGGTCTTGTTATGCTTTGCATACATGGCTCACTCGTA
         GT GCTGAGGAGGA GC ACCTC GGTCTTGT ATG T TGCATACATGGCTC C GT
-MEXICO  GTGGCTGAGGAGGAAGCCACCTCCGGTCTTGTCATGTTATGCATACATGGCTCTCCAGTT 6010v      6020v      6030v      6040v      6050v      6060v
-BURMA   AATTCCTATACTAATACACCCTATACCGGTGCCCTCGGGCTGTTGGACTTTGCCCTTGAG
         AA TCCTATAC AATAC CC TATACCGGTGCCCT GG  T  TGGACTTTGCC T GAG
-MEXICO  AACTCCTATACCAATACCCCTTATACCGGTGCCCTTGGCTTACTGGACTTTGCCTTAGAG
```

```
                  6070v        6080v         6090v         6100v         6110v         6120v
-BURMA   CTTGAGTTTCGCAACCTTACCCCCGGTAACACCAATACGCGGGTCTCCCGTTATTCCAGC
         CTTGAGTTTCGCAA CT ACC CC GTAACACCAATAC CG GT TCCCGTTA TCCAGC
-MEXICO  CTTGAGTTTCGCAATCTCACCACCTGTAACACCAATACACGTGTGTCCCGTTACTCCAGC 6130v        6140v         6150v         6160v         6170v         6180v
-BURMA   ACTGCTCGCCACCGCCTTCGTCGCGGTGCGGACGGGACTGCCGAGCTCACCACCACGGCT
         ACTGCTCG CAC  C   CG  G   G       GACGGGACTGC GAGCT ACCAC AC GC
-MEXICO  ACTGCTCGTCACTCCGCCCGAGGGGCC---GACGGGACTGCGGAGCTGACCACAACTGCA 6190v        6200v         6210v         6220v         6230v         6240v
-BURMA   GCTACCCGCTTTATGAAGGACCTCTATTTTACTAGTACTAATGGTGTCGGTGAGATCGGC
         GC ACC G TT ATGAA GA CTC A TTTAC  G    TAATGG GT GGTGA  TCGGC
-MEXICO  GCCACCAGGTTCATGAAAGATCTCCACTTTACCGGCCTTAATGGGGTAGGTGAAGTCGGC 6250v        6260v         6270v         6280v         6290v         6300v
-BURMA   CGCGGGATAGCCCTCACCCTGTTCAACCTTGCTGACACTCTGCTTGGCGGCCTGCCGACA
         CGCGGGATAGC CT AC  T  T AACCTTGCTGACAC CT CT GGCGG CT CCGACA
-MEXICO  CGCGGGATAGCTCTAACATTACTTAACCTTGCTGACACGCTCCTCGGCGGGCTCCCGACA 6310v        6320v         6330v         6340v         6350v         6360v
-BURMA   GAATTGATTTCGTCGGCTGGTGGCCAGCTGTTCTACTCCCGTCCCGTTGTCTCAGCCAAT
         GAATT ATTTCGTCGGCTGG GG CA CTGTT TA TCCCG CC GTTGTCTCAGCCAAT
-MEXICO  GAATTAATTTCGTCGGCTGGCGGGCAACTGTTTTATTCCCGCCCGGTTGTCTCAGCCAAT 6370         6380v         6390v         6400v         6410v         6420v
-BURMA   GGCGAGCCGACTGTTAAGTTGTATACATCTGTAGAGAATGCTCAGCAGGATAAGGGTATT
         GGCGAGCC AC GT AAG T TATACATC GT GAGAATGCTCAGCAGGATAAGGGT TT
-MEXICO  GGCGAGCCAACCGTCAAGCTCTATACATCAGTGGAGAATGCTCAGCAGGATAAGGGTGTT 6430v        6440v         6450v         6460v         6470v         6480v
-BURMA   GCAATCCCGCATGACATTGACCTCGGAGAATCTCGTGTGGTTATTCAGGATTATGATAAC
         GC ATCCC CA GA AT GA CT GG GA TC CGTGTGGT ATTCAGGATTATGA AAC
-MEXICO  GCTATCCCCCACGATATCGATCTTGGTGATTCGCGTGTGGTCATTCAGGATTATGACAAC 6490v        6500v         6510v         6520v         6530v         6540v
-BURMA   CAACATGAACAAGATCGGCCGACGCCTTCTCCAGCCCCATCGCGCCCTTTCTCTGTCCTT
         CA CATGA CA GATCGGCC AC CC TC CC GC CCATC CG CCTTT TCTGT CT
-MEXICO  CAGCATGAGCAGGATCGGCCCACCCCGTCGCCTGCGCCATCTCGGCCTTTTTCTGTTCTC 6550v        6560v         6570v         6580v         6590v         6600v
-BURMA   CGAGCTAATGATGTGCTTTGGCTCTCTCTCACCGCTGCCGAGTATGACCAGTCCACTTAT
         CGAGC AATGATGT CTTTGGCT TC CTCAC GC GCCGAGTATGACCAGTCCACTTA
-MEXICO  CGAGCAAATGATGTACTTTGGCTGTCCCTCACTGCAGCCGAGTATGACCAGTCCACTTAC 6610v        6620v         6630v         6640v         6650v         6660v
-BURMA   GGCTCTTCGACTGGCCCAGTTTATGTTTCTGACTCTGTGACCTTGGTTAATGTTGCGACC
         GG TC TC ACTGGCCC GTTTAT T TC GAC   GTGAC TTGGT AATGTTGCGAC
-MEXICO  GGGTCGTCAACTGGCCCGGTTTATATCTCGGACAGCGTGACTTTGGTGAATGTTGCGACT 6670v        6680v         6690v         6700v         6710v         6720v
-BURMA   GGCGCGCAGGCCGTTGCCCGGTCGCTCGATTGGACCAAGGTCACACTTGACGGTCGCCCC
         GGCGCGCAGGCCGT  GCCCG TCGCT GA TGG CCAA GTCAC CT GACGG CG CCC
-MEXICO  GGCGCGCAGGCCGTAGCCCGATCGCTTGACTGGTCCAAAGTCACCCTCGACGGGCGGCCC 6730v        6740v         6750v         6760v         6770v         6780v
-BURMA   CTCTCCACCATCCAGCAGTACTCGAAGACCTTCTTTGTCCTGCCGCTCCGCGGTAAGCTC
         CTC  C AC  T   AGCA TA TC AAGAC TTCTTTGT CT CC CT CG GG AAGCTC
-MEXICO  CTCCCGACTGTTGAGCAATATTCCAAGACATTCTTTGTGCTCCCCTTCGTGGCAAGCTC 6790v        6800v         6810v         6820v         6830v         6840v
-BURMA   TCTTTCTGGGAGGCAGGCACAACTAAAGCCGGGTACCCTTATAATTATAACACCACTGCT
         TC TT TGGGAGGC GGCACAAC AAAGC GG TA CCTTATAATTATAA ACTGCT
-MEXICO  TCCTTTTGGGAGGCCGGCACAACAAAAGCAGGTTATCCTTATAATTATAATACTGCT 6850v        6860v         6870v         6880v         6890v         6900v
-BURMA   AGCGACCAACTGCTTGTCGAGAATGCCGCCGGGCACCGGGTCGCTATTTCCACTTACACC
         AG  GACCA  T  CT  T GA AATGC GCCGG CA CGGGTCGC ATTTC AC TA ACC
-MEXICO  AGTGACCAGATTCTGATTGAAAATGCTGCCGGCCATCGGGTCGCCATTTCAACCTATACC 6910v        6920v         6930v         6940v         6950v         6960v
-BURMA   ACTAGCCTGGGTGCTGGTCCCGTCTCCATTTCTGCGGTTGCCGTTTTAGCCCCCCACTCT
         AC AG CT GG GC GGTCC GTC CCATTTCTGCGG  GC GTTTT GC CC C CTC
-MEXICO  ACCAGGCTTGGGGCCGGTCCGGTCGCCATTTCTGCGGCCGCGGTTTTGGCTCCACGCTCC 6970v        6980v         6990v         7000v         7010v         7020v
-BURMA   GCGCTAGCATTGCTTGAGGATACCTTGGACTACCCTGCCCGCGCCCATACTTTTGATGAT
         GC CT GC  TGCT GAGGATAC TT GA TA CC G  CG GC CA AC TTTGATGA
-MEXICO  GCCCTGGCTCTGCTGGAGGATACTTTTGATTATCCGGGGCGGGCGCACACATTTGATGAC
```

-continued

```
              7030v         7040v         7050v         7060v         7070v         7080v
-BURMA   TTCTGCCCAGAGTGCCGCCCCCTTGGCCTTCAGGGCTGCGCTTTCCAGTCTACTGTCGCT
         TTCTGCCC GA TGCCGC  C   T  GGCCT CAGGG TG GCTTTCCAGTC ACTGTCGCT

-MEXICO  TTCTGCCCTGAATGCCGCGCTTTAGGCCTCCAGGGTTGTGCTTTCCAGTCAACTGTCGCT 7090v         7100v         7110v         7120v         7130v         7140v
-BURMA   GAGCTTCAGCGCCTTAAGATGAAGGTGGGTAAAACTCGGGAGTTGTAGTTTATTTGCTTG
         GAGCT CAGCGCCTTAA  T  AAGGTGGGTAAAACTCGGGAGTTGTAGTTTATTTG  TG

-MEXICO  GAGCTCCAGCGCCTTAAAGTTAAGGTGGGTAAAACTCGGGAGTTGTAGTTTATTTGGCTG 7150v    7160v                    7170v         7180v         7190v
-BURMA   TGCCCCCCTTCTTTCTGTTGC ................TTATTTCTCATTTCTGCGTTCCGCGCTCCC
         TGCCC  CCT CTT    TGC              TTATTTC    TTTCT GT CCGCGCTCCC

-MEXICO  TGCCCACCTACTTATATCTGCTGATTTCCTTTATTTCCTTTTTCTCGGTCCCGCGCTCCC v 7195
-BURMA   TGA
         TGA

-MEXICO  TGA
```

A number of open reading frames, which are potential coding regions, have been found within the DNA sequences set forth above. As has already been noted, consensus residues for the RNA-directed RNA polymerase (RDRP) were identified in the HEV (Burma) strain clone ET1.1. Once a contiguous overlapping set of clones was accumulated, it became clear that the nonstructural elements containing the RDRP as well as what were identified as consensus residues for the helicase domain were located in the first large open reading frame (ORFI). ORFI covers the 5' half of the genome and begins at the first encoded met, after the 27th bp of the apparent non-coding sequence, and then extends 5079 bp before reaching a termination codon. Beginning 37 bp downstream from the ORF1 stop codon in the plus 1 frame is the second major opening reading frame (ORF2) extending 1980 bp and terminating 68 bp upstream from the point of poly A addition. The third forward ORF (in the plus 2 frame) is also utilized by HEV. ORF3 is only 370 bp in length and would not have been predicted to be utilized by the virus were it not for the identification of the immunoreactive cDNA clone 406.4-2 from the Mexico SISPA cDNA library (see below for detailed discussion). This epitope confirmed the utilization of ORF3 by the virus, although the means by which this ORF is expressed has not yet been fully elucidated. If we assume that the first met is utilized, ORF3 overlaps ORF1 by 1 bp at its 5' end and ORF2 by 328 bp at its 3' end. ORF2 contains the broadly reactive 406.3-2 epitope and also a signal sequence at its extreme 5' end. The first half of this ORF2 also has a high pI value (>10) similar to that seen with other virus capsid proteins. These data suggest that the ORF2 might be the predominant structural gene of HEV.

The existence of subgenomic transcripts prompted a set of experiments to determine whether these RNAs were produced by splicing from the 5' end of the genome. An analysis using subgenomic probes from throughout the genome, including the extreme 5' end, did not provide evidence for a spliced transcript. However, it was discovered that a region of the genome displayed a high degree of homology with a 21 bp segment identified in Sindbis as a probably internal initiation site for RNA transcription used in the production of its subgenomic messages. Sixteen of 21 (76%) of the nucleotides are identical.

Two cDNA clones which encode an epitope of HEV that is recognized by sera collected from different ET-NANB outbreaks (i.e., a universally recognized epitope) have been isolated and characterized. One of the clones immunoreacted with 8 human sera from different infected individuals and the other clone immunoreacted with 7 of the human sera tested. Both clones immunoreacted specifically with cyno sera from infected animals and exhibited no immunologic response to sera from uninfected animals. The sequences of the cDNAs in these recombinant phages, designated 406.3-2 and 406.4-2 have been determined. The HEV open reading frames are shown to encode epitopes specifically recognized by sera from patients with HEV infections. The cDNA sequences and the polypeptides that they encode are set forth below.

Epitopes derived from Mexican strain of HEV:

406.4-2 sequence (nucleotide sequence has SEQ ID NO.13; amino acid sequence has SEQ ID NO.14) with 406.3-2 sequence (nucleotide sequence has SEQ ID NO.15; amino acid sequence has SEQ ID NO.16).

SEQ ID NO. 16:

```
Thr Phe Asp Tyr Pro Gly Arg Ala His Thr Phe Asp Asp Phe Cys Pro
 1               5                  10                  15
Glu Cys Arg Ala Leu Gly Leu Gln Gly Cys Ala Phe Gln Ser Thr Val
            20                  25                  30
Ala Glu Leu Gln Arg Leu Lys Val Lys Val
        35                  40
```

The universal nature of these epitopes is evident from the homology exhibited by the DNA that encodes them. If the epitope coding sequences from the Mexican strains shown above are compared to DNA sequences from other strains, such as the Burmese strain also set forth above, similarities are evident, as shown in the following comparisons.

Comparison of 406.4-2 epitopes, HEV Mexico and Burma strains:

```
                        10            20              30
MEXICAN(SEQ ID NO.17)   ANQP GHLAP LGEEI RS AP P LP P VADLP QP GLRR
                        : : . : . :   : : : :   . : : : : : : : : : : . : . : : : :   :   : :
BURMA(SEQ ID NO.18)     ANP P DHS AP LGVTRP S AP P LP HVVDLP QLGP RR
                        10            20              30
```

There is 73.5% identity in a 33-amino acid overlap. Comparison of 406.3-2 epitopes, HEV Mexico and Burma strains:

```
                        10              20              30              40
MEXICAN(SEQ ID No.19)   T F D YP G R AHT F DDF CP E CR AL GL QGCAF QS T VAE L QRL KVK V
                        : . : : : . : : : : : : : : : : . : : : : : : : : : : : : : : ★ : : : . : :
BURMA(SEQ ID No.20)     T L D YP A R AHT F DDF CP E CR P  GL QGCAF QS T VAE L QRL KMK V
                        10              20              30              40
```

There is 90.5% identity in the 42-amino acid overlap.

It will be recognized by one skilled in the art of molecular genetics that each of the specific DNA sequences given above shows a corresponding complementary DNA sequence as well as RNA sequences corresponding to both the principal sequence shown and the complementary DNA sequence. Additionally, open reading frames encoding peptides are present, and expressible peptides are disclosed by the nucleotide sequences without setting forth the amino acid sequences explicitly, in the same manner as if the amino acid sequences were explicitly set forth as in the ET1.1 sequence or other sequences above.

DETAILED DESCRIPTION OF THE INVENTION

I. Definitions

The terms defined below have the following meaning herein:

1. "Enterically transmitted non-A/non-B hepatitis viral agent, ET-NANB, or HEV" means a virus, virus type, or virus class which (1) causes water-borne, infectious hepatitis, (ii) is transmissible in cynomolgus monkeys, (iii) is serologically distinct from hepatitis A virus (HAV), hepatitis B virus (HBV), hepatitis C virus (HCV), and hepatitis D virus, and (iv) includes a genomic region which is homologous to the 1.33 kb cDNA insert in plasmid pTZKF1 (ET1.1) carried in *E. coli* strain BB4 identified by ATCC deposit number 67717.

2. Two nucleic acid fragments are "homologous" if they are capable of hybridizing to one another under hybridization conditions described in Maniatis et al., op. cit., pp. 320–323. However, using the following wash conditions: 2×SCC, 0.1% SDS, room temperature twice, 30 minutes each; then 2×SCC, 0.1% SDS, 50° C. once, 30 minutes; then 2×SCC, room temperature twice, 10 minutes each, homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash conditions for identification of clones from gene libraries (or other sources of genetic material), as is well known in the art.

3. Two amino acid sequences or two nucleotide sequences (in an alternative definition for homology between two nucleotide sequences) are considered homologous (as this term is preferably used in this specification) if they have an alignment score of >5 (in standard deviation units) using the program ALIGN with the mutation gap matrix and a gap penalty of 6 or greater. See Dayhoff, M. O., in *Atlas of Protein Sequence and Structure* (1972) Vol. 5, National Biomedical Research Foundation, pp. 101–110, and Supplement 2 to this volume, pp. 1–10. The two sequences (or parts thereof, preferably at least 30 amino acids in length) are more preferably homologous if their amino acids are greater than or equal to 50% identical when optimally aligned using the ALIGN program mentioned above.

4. A DNA fragment is "derived from" an ET-NANB viral agent if it has the same or substantially the same basepair sequence as a region of the viral agent genome.

5. A protein is "derived from" an ET-NANB viral agent if it is encoded by an open reading frame of a DNA or RNA fragment derived from an ET-NANB viral agent.

6. A protein or polypeptide is "specifically immunoreactive" with antibodies or sera from individuals infected with HEV if it specifically reacts with such antibodies or sera but does not specifically react with antibodies or sera from uninfected individuals.

II. Obtaining Cloned ET-NANB Fragments

According to one aspect of the invention, it has been found that a virus-specific DNA clone can be produced by (a) isolating RNA from the bile of a cynomolgus monkey having a known ET-NANB infection, (b) cloning the cDNA fragments to form a fragment library, and (c) screening the library by differential hybridization to radiolabeled cDNAs from infected and non-infected bile sources.

A. cDNA Fragment Mixture

ET-NANB infection in cynomolgus monkeys is initiated by inoculating the animals intravenously with a 10% w/v suspension from human case stools positive for 27–34 nm ET-NANB particles (mean diameter 32 nm). An infected animal is monitored for elevated levels of alanine aminotransferase, indicating hepatitis infection. ET-NANB infection is confirmed by immunospecific binding of seropositive antibodies to virus-like particles (VLPs), according to published methods (Gravelle). Briefly, a stool (or bile) specimen taken from the infected animal 3–4 weeks after infection is diluted 1:10 with phosphate-buffered saline, and the 10t suspension is clarified by low-speed centrifugation and filtration successively through 1.2 and 0.45 micron filters. The material may be further purified by pelleting through a 30% sucrose cushion (Bradley). The resulting preparation of VLPs is mixed with diluted serum from human patients with known ET-NANB infection. After incubation overnight, the mixture is centrifuged overnight to pellet immune aggregates, and these are stained and examined by electron microscopy for antibody binding to the VLPs.

ET-NANB infection can also be confirmed by seroconversion to VLP-positive serum. Here the serum of the infected animal is mixed as above with 27–34 nm VLPs isolated from the stool specimens of infected human cases and examined by immune electron microscopy for antibody binding to the VLPs.

Bile can be collected from ET-NANB positive animals by either cannulating the bile duct and collecting the bile fluid or by draining the bile duct during necropsy. Total RNA is extracted from the bile by hot phenol extraction, as outlined in Example 1A. The RNA fragments are used to synthesize corresponding duplex cDNA fragments by random priming, also as referenced in Example 1A. The cDNA fragments may be fractionated by gel electrophoresis or density gradient centrifugation to obtain a desired size class of fragments, e.g., 500–4,000 basepair fragments.

Although alternative sources of viral material, such as VLPs obtained from stool samples (as described in Example 4), may be used for producing a cDNA fraction, the bile source is preferred. According to one aspect of the invention, it has been found that bile from ET-NANB-infected monkeys shows a greater number of intact viral particles than material obtained from stool samples, as evidenced by immune electron microscopy. Bile obtained from an ET-NANB infected human or cynomolgus macaque, for use as a source of ET-NANB viral protein or genomic material, or intact virus, forms part of the present invention.

B. cDNA Library and Screening

The cDNA fragments from above are cloned into a suitable cloning vector to form a cDNA library. This may be done by equipping blunt-ended fragments with a suitable end linker, such as an EcoRI sequence, and inserting the fragments into a suitable insertion site of a cloning vector, such as at a unique EcoRI site. After initial cloning, the library may be re-cloned, if desired, to increase the percentage of vectors containing a fragment insert. The library construction described in Example 1B is illustrative. Here cDNA fragments were blunt-ended, equipped with EcoRI ends, and inserted into the EcoRI site of the lambda phage vector gt10. The library phage, which showed less than 5% fragment inserts, was isolated, and the fragment inserts re-cloned into the lambda gt10 vector, yielding more than 95% insert-containing phage.

The cDNA library is screened for sequences specific for ET-NANB by differential hybridization to cDNA probes derived from infected and non-infected sources. cDNA fragments from infected and non-infected source bile or stool viral isolates can be prepared as above. Radiolabeling the fragments is by random labeling, nick translation, or end labeling, according to conventional methods (Maniatis, p. 109). The cDNA library from above is screened by transfer to duplicate nitrocellulose filters, and hybridization with both infected-source and non-infected-source (control) radiolabeled probes, as detailed in Example 2. In order to recover sequences that hybridize at the preferred outer limit of 25–30% basepair mismatches, clones can be selected if they hybridize under the conditions described in Maniatis et al., op. cit., pp. 320–323, but using the following wash conditions: 2×SCC, 0.1% SDS, room temperature—twice, 30 minutes each; then 2×SCC, 0.1% SDS, 50° C.—once, 30 minutes; then 2×SCC, room temperature—twice, 10 minutes each. These conditions allowed identification of the Mexican isolate discussed above using the ET1.1 sequence as a probe. Plaques which show selective hybridization to the infected-source probes are preferably re-plated at low plating density and re-screened as above, to isolate single clones which are specific for ET-NANB sequences. As indicated in Example 2, sixteen clones which hybridized specifically with infected-source probes were identified by these procedures. One of the clones, designated lambda gt101.1, contained a 1.33 kilobase fragment insert.

C. ET-NANB Sequences

The basepair sequence of cloned regions of the ET-NANB fragments from Part B are determined by standard sequencing methods. In one illustrative method, described in Example 3, the fragment insert from the selected cloning vector is excised, isolated by gel electrophoresis, and inserted into a cloning vector whose basepair sequence on either side of the insertion site is known. The particular vector employed in Example 3 is a pTZKF1 vector shown at the left in FIG. 1. The ET-NANB fragment from the gt10-1.1 phage was inserted at the unique EcoRI site of the pTZKF1 plasmid. Recombinants carrying the desired insert were identified by hybridization with the isolated 1.33 kilobase fragment, as described in Example 3. One selected plasmid, identified as pTZKF1(ET1.1), gave the expected 1.33 kb fragment after vector digestion with EcoRI. E. coli strain BB4 infected with the pTZKF1(ET1.1) plasmid has been deposited with the American Type Culture Collection, Rockville, Md., and is identified by ATCC deposit number 67717.

The pTZKF1(ET1.1) plasmid is illustrated at the bottom in FIG. 1. The fragment insert has 5' and 3' end regions denoted at A and C, respectively, and an intermediate region, denoted at B. The sequences in these regions were determined by standard dideoxy sequencing and were set forth in an earlier application in this series. The three short sequences (A, B, and C) are from the same insert strand. As will be seen in Example 3, the B-region sequence was actually determined from the opposite strand, so that the B region sequence shown above represents the complement of the sequence in the sequenced strand. The base numbers of the partial sequences are approximate.

Later work in the laboratory of the inventors identified the full sequence, set forth above. Fragments of this total sequence can readily be prepared using restriction endonucleases. Computer analysis of both the forward and reverse sequence has identified a number of cleavage sites.

III. ET-NANB Fragments

According to another aspect, the invention includes ET-NANB-specific fragments or probes which hybridize with ET-NANB genomic sequences or cDNA fragments derived therefrom. The fragments may include full-length cDNA fragments such as described in Section II, or may be derived from shorter sequence regions within cloned cDNA fragments. Shorter fragments can be prepared by enzymatic digestion of full-length fragments under conditions which yield desired-sized fragments, as will be described in Section IV. Alternatively, the fragments can be produced by oligonucleotide synthetic methods, using sequences derived from the cDNA fragments. Methods or commercial services for producing selected-sequence oligonucleotide fragments are available. Fragments are usually at least 12 nucleotides in length, preferably at least 14, 20, 30 or 50 nucleotides, when used as probes. Probes can be full length or less than 500, preferably less than 300 or 200, nucleotides in length.

To confirm that a given ET-NANB fragment is in fact derived from the ET-NANB viral agent, the fragment can be shown to hybridize selectively with cDNA from infected sources. By way of illustration, to confirm that the 1.33 kb fragment in the pTZKF1(ET1.1) plasmid is ET-NANB in origin, the fragment was excised from the pTZKF1(ET1.1) plasmid, purified, and radiolabeled by random labeling. The radiolabeled fragment was hybridized with fractionated cDNAs from infected and non-infected sources to confirm that the probe reacts only with infected-source cDNAs. This method is illustrated in Example 4, where the above radiolabeled 1.33 kb fragment from pTZKF1(ET1.1) plasmid was examined for binding to cDNAs prepared from infected and non-infected sources. The infected sources are (1) bile from a cynomolgus macaque infected with a strain of virus derived from stool samples from human patients from Burma with known ET-NANB infections and (2) a viral agent derived from the stool sample of a human ET-NANB patient from Mexico. The cDNAs in each fragment mixture were first amplified by a linker/primer amplification method described in Example 4. Fragment separation was on agarose gel, followed by Southern blotting and then hybridization to bind the radiolabeled 1.33 kb fragment to the fractionated cDNAs. The lane containing cDNAs from the infected sources showed a smeared band of bound probe, as expected (cDNAs amplified by the linker/primer amplification method would be expected to have a broad range of sizes). No probe binding to the amplified cDNAs from the non-infected sources was observed. The results indicate that the 1.33 kb probe is specific for cDNA fragments associated with ET-NANB infection. This same type of study, using ET 1.1 as the probe, has demonstrated hybridization to ET-NANB samples collected from Tashkent, Somalia, Borneo and Pakistan. Secondly, the fact that the probe is specific for ET-NANB related sequences derived from different continents (Asia, Africa and North America) indicates the cloned ET-NANB Burma sequence (ET1.1) is derived from a common ET-NANB virus or virus class responsible for ET-NANB hepatitis infection worldwide.

In a related confirmatory study, probe binding to fractionated genomic fragments prepared from human or cynomolgus macaque genomic DNA (both infected and uninfected) was examined. No probe binding was observed to either genomic fraction, demonstrating that the ET-NANB fragment is not an endogenous human or cynomolgus genomic fragment and additionally demonstrating that HEV is an RNA virus.

Another confirmation of ET-NANB specific sequences in the fragments is the ability to express ET-NANB proteins from coding regions in the fragments and to demonstrated specific sero-reactivity of these proteins with sera collected during documented outbreaks of ET-NANB. Section IV below discusses methods of protein expression using the fragments.

One important use of the ET-NANB-specific fragments is for identifying ET-NANB-derived cDNAs which contain additional sequence information. The newly identified cDNAs, in turn, yield new fragment probes, allowing further iterations until the entire viral genome is identified and sequenced. Procedures for identifying additional ET-NANB library clones and generating new probes therefrom generally follow the cloning and selection procedures described in Section II.

The fragments (and oligonucleotides prepared based on the sequences given above) are also useful as primers for a polymerase chain reaction method of detecting ET-NANB viral genomic material in a patient sample. This diagnostic method will be described in Section V below.

Two specific genetic sequences derived from the Mexican strain, identified herein as 406.3-2 and 406.4-2, have been identified that encode immunogenic epitopes. This was done by isolating clones which encode epitopes that immunologically react specifically with sera from individuals and experimental animals infected with HEV. Comparison of the isolated sequences with those in the Genebank collection of genetic sequences indicate that these viral sequences are novel. Since these sequences are unique, they can be used to identify the presence of HEV and to distinguish this strain of hepatitis from HAV, HBV, and HCV strains. The sequences are also useful for the design of oligonucleotide probes to diagnose the presence of virus in samples. They can be used for the synthesis of polypeptides that themselves are used in immunoassays. The specific 406.3-2 and 406.4-2 sequences can be incorporated into other genetic material, such as vectors, for ease of expression or replication. They can also be used (as demonstrated above) for identifying similar antigenic regions encoded by related viral strains, such as the Burmese strain.

IV. ET-NANB Proteins

As indicated above, ET-NANB proteins can be prepared by expressing open reading-frame coding regions in ET-NANB fragments. In one preferred approach, the ET-NANB fragments used for protein expression are derived from cloned cDNAs which have been treated to produce desired-size fragments, and preferably random fragments with sizes predominantly between about 100 to about 300 base pairs. Example 5 describes the preparation of such fragments by DNAs digestion. Because it is desired to obtain peptide antigens of between about 30 to about 100 amino acids, the digest fragments are preferably size fractionated, for example by gel electrophoresis, to select those in the approximately 100–300 basepair size range. Alternatively, cDNA libraries constructed directly from HEV-containing sources (e.g., bile or stool) can be screened directly if cloned into an appropriate expression vector (see below).

For example, the ET-NANB proteins expressed by the 406.3-2 and 406.4-2 sequences (and peptide fragments thereof) are particularly preferred since these proteins have been demonstrated to be immunoreactive with a variety of different human sera, thereby indicating the presence of one or more epitopes specific for HEV on their surfaces. These clones were identified by direct screening of a gt11 library.

A. Expression Vector

The ET-NANB fragments are inserted into a suitable expression vector. One exemplary expression vector is lambda gt11, which contains a unique EcoRI insertion site 53 base pairs upstream of the translation termination codon of the beta-galactosidase gene. Thus, the inserted sequence will be expressed as a beta-galactosidase fusion protein which contains the N-terminal portion of the beta-galactosidase gene, the heterologous peptide, and optionally the C-terminal region of the beta-galactosidase peptide (the C-terminal portion being expressed when the heterologous peptide coding sequence does not contain a translation termination codon). This vector also produces a temperature-sensitive repressor (c1857) which causes viral lysogeny at permissive temperatures, e.g., 32° C., and leads to viral lysis at elevated temperatures, e.g., 37° C. Advantages of this vector include: (1) highly efficient recombinant generation, (2) ability to select lysogenized host cells on the basis of host-cell growth at permissive, but not non-permissive, temperatures, and (3) high levels of recombinant fusion protein production. Further, since phage containing a heterologous insert produces an inactive beta-galactosidase enzyme, phage with inserts can be readily identified by a beta-galactosidase colored-substrate reaction.

For insertion into the expression vector, the viral digest fragments may be modified, if needed, to contain selected restriction-site linkers, such as EcoRI linkers, according to conventional procedures. Example 1 illustrates methods for cloning the digest fragments into lambda gt11, which includes the steps of blunt-ending the fragments, ligating with EcoRI linkers, and introducing the fragments into EcoRI-cut lambda gt11. The resulting viral genomic library may be checked to confirm that a relatively large (representative) library has been produced. This can be done, in the case of the lambda gt11 vector, by infecting a suitable bacterial host, plating the bacteria, and examining the plaques for loss of beta-galactosidase activity. Using the procedures described in Example 1, about 50% of the plaques showed loss of enzyme activity.

B. Peptide Antigen Expression

The viral genomic library formed above is screened for production of peptide antigen (expressed as a fusion protein) which is immunoreactive with antiserum from ET-NANB seropositive individuals. In a preferred screening method, host cells infected with phage library vectors are plated, as above, and the plate is blotted with a nitrocellulose filter to transfer recombinant protein antigens produced by the cells onto the filter. The filter is then reacted with the ET-NANB antiserum, washed to remove unbound antibody, and reacted with reporter-labeled, anti-human antibody, which becomes bound to the filter, in sandwich fashion, through the anti-ET-NANB antibody.

Typically phage plaques which are identified by virtue of their production of recombinant antigen of interest are re-examined at a relatively low density for production of antibody-reactive fusion protein. Several recombinant phage clones which produced immunoreactive recombinant antigen were identified in the procedure.

The selected expression vectors may be used for scale-up production, for purposes of recombinant protein purification. Scale-up production is carried out using one of a variety of reported methods for (a) lysogenizing a suitable host, such as E. coli, with a selected lambda gt11 recombinant (b) culturing the transduced cells under conditions that yield high levels of the heterologous peptide, and (c) purifying the recombinant antigen from the lysed cells.

In one preferred method involving the above lambda gt11 cloning vector, a high-producer E. coli host, BNN103, is infected with the selected library phage and replica plated on two plates. One of the plates is grown at 32° C., at which viral lysogeny can occur, and the other at 42° C., at which the infecting phage is in a lytic stage and therefore prevents cell growth. Cells which grow at the lower but not the higher temperature are therefore assumed to be successfully lysogenized.

The lysogenized host cells are then grown under liquid culture conditions which favor high production of the fused protein containing the viral insert, and lysed by rapid freezing to release the desired fusion protein.

C. Peptide Purification

The recombinant peptide can be purified by standard protein purification procedures which may include differential precipitation, molecular sieve chromatography, ion-exchange chromatography, isoelectric focusing, gel electrophoresis and affinity chromatography. In the case of a fused protein, such as the beta-galactosidase fused protein prepared as above, the protein isolation techniques which are used can be adapted from those used in isolation of the native protein. Thus, for isolation of a soluble betagalactosidase fusion protein, the protein can be isolated readily by simple affinity chromatography, by passing the cell lysis material over a solid support having surface-bound anti-beta-galactosidase antibody.

D. Viral Proteins

The ET-NANB protein of the invention may also be derived directly from the ET-NANB viral agent. VLPs or protein isolated from stool or liver samples from an infected individual, as above, are one suitable source of viral protein material. The VLPs isolated from the stool sample may be further purified by affinity chromatography prior to protein isolation (see below). The viral agent may also be raised in cell culture, which provides a convenient and potentially concentrated source of viral protein. Co-owned U.S. patent application Ser. No. 846,757, filed Apr. 1, 1986, describes an immortalized trioma liver cell which supports NANB infection in cell culture. The trioma cell line is prepared by fusing human liver cells with a mouse/human fusion partner selected for human chromosome stability. Cells containing the desired NANB viral agent can be identified by immunofluorescence methods, employing anti-ET-NANB human antibodies.

The viral agent is disrupted, prior to protein isolation, by conventional methods, which can include sonication, high- or low-salt conditions, or use of detergents.

Purification of ET-NANB viral protein can be carried out by affinity chromatography, using a purified anti-ET-NANB antibody attached according to standard methods to a suitable solid support. The antibody itself may be purified by affinity chromatography, where an immunoreactive recombinant ETNANB protein, such as described above, is attached to a solid support, for isolation of anti-ET-NANB antibodies from an immune serum source. The bound antibody is released from the support by standard methods.

Alternatively, the anti-ET-NANB antibody may be an antiserum or a monoclonal antibody (Mab) prepared by immunizing a mouse or other animal with recombinant ETNANB protein. For Mab production, lymphocytes are isolated from the animal and immortalized with a suitable fusion partner, and successful fusion products which react with the recombinant protein immunogen are selected. These in turn may be used in affinity purification procedures, described above, to obtain native ET-NANB antigen.

V. Utility

Although ET-NANB is primarily of interest because of its effects on humans, recent data has shown that this virus is also capable of infecting other animals, especially mammals. Accordingly, any discussion herein of utility applies to both human and veterinary uses, especially commercial veterinary uses, such as the diagnosis and treatment of pigs, cattle, sheep, horses, and other domesticated animals.

A. Diagnostic Methods

The particles and antigens of the invention, as well as the genetic material, can be used in diagnostic assays. Methods for detecting the presence of ET-NANB hepatitis comprise analyzing a biological sample such as a blood sample, stool sample or liver biopsy specimen for the presence of an analyte associated with ET-NANB hepatitis virus.

The analyte can be a nucleotide sequence which hybridizes with a probe comprising a sequence of at least about 16 consecutive nucleotides, usually 30 to 200 nucleotides, up to substantially the full sequence of the sequences shown above (cDNA sequences). The analyte can be RNA or cDNA. The analyte is typically a virus particle suspected of being ET-NANB or a particle for which this classification is being ruled out. The virus particle can be further characterized as having an RNA viral genome comprising a sequence at least about 70% homologous to a sequence of at least 12 consecutive nucleotides of the "forward" and "reverse" sequences given above, usually at least about 80% homologous to at least about 60 consecutive nucleotides within the sequences, and may comprise a sequence substantially homologous to the full-length sequences. In order to detect an analyte, where the analyte hybridizes to a probe, the probe may contain a detectable label. Particularly preferred for use as a probe are sequences of consecutive nucleotides derived from the 406.3-2 and 406.4-2 clones described herein, since these clones appear to be particularly diagnostic for HEV.

The analyte can also comprise an antibody which recognizes an antigen, such as a cell surface antigen, on a ET-NANB virus particle. The analyte can also be a ET-NANB viral antigen. Where the analyte is an antibody or an antigen, either a labelled antigen or antibody, respectively, can be used to bind to the analyte to form an immunological complex, which can then be detected by means of the label.

Typically, methods for detecting analytes such as surface antigens and/or whole particles are based on immunoassays. Immunoassays can be conducted either to determine the presence of antibodies in the host that have arisen from infection by ET-NANB hepatitis virus or by assays that directly determine the presence of virus particles or antigens. Such techniques are well known and need not be described here in detail. Examples include both heterogeneous and homogeneous immunoassay techniques. Both techniques are based on the formation of an immunological complex between the virus particle or its antigen and a corresponding specific antibody. Heterogeneous assays for viral antigens typically use a specific monoclonal or polyclonal antibody bound to a solid surface. Sandwich assays are becoming increasingly popular. Homogeneous assays, which are carried out in solution without the presence of a solid phase, can also be used, for example by determining the difference in enzyme activity brought on by binding of free antibody to an enzyme-antigen conjugate. A number of suitable assays are disclosed in U.S. Pat. Nos. 3,817,337, 4,006,360, 3,996,345.

When assaying for the presence of antibodies induced by ET-NANB viruses, the viruses and antigens of the invention can be used as specific binding agents to detect either IgG or IgM antibodies. Since IgM antibodies are typically the first antibodies that appear during the course of an infection, when IgG synthesis may not yet have been initiated, specifically distinguished between IgM and IgG antibodies present in the blood stream of a host will enable a physician or other investigator to determine whether the infection is recent or convalescent. Proteins expressed by the 406.3-2 and 406.4-2 clones described herein and peptide fragments thereof are particularly preferred for use as specific binding agents to detect antibodies since they have been demonstrated to be reactive with a number of different human HEV sera. Further, they are reactive with both acute and convalescent sera.

In one diagnostic configuration, test serum is reacted with a solid phase reagent having surface-bound ET-NANB protein antigen. After binding anti-ET-NANB antibody to the reagent and removing unbound serum components by washing, the reagent is reacted with reporter-labeled anti-human antibody to bind reporter to the reagent in proportion to the amount of bound anti-ET-NANB antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric or calorimetric substrate.

The solid surface reagent in the above assay prepared by known techniques for attaching protein material to solid support material, such as polymeric beads, dip sticks, or filter material. These attachment methods generally include non-specific adsorption of the protein to the support or covalent attachment of the protein, typically through a free amine group, to a chemically reactive group on the solid support, such as an activate carboxyl, hydroxyl, or aldehyde group.

In a second diagnostic configuration, known as a homogeneous assay, antibody binding to a solid support produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting the serum from a test individual with the protein antigen and examining the antigen for the presence of bound antibody. The examining may involve attaching a labeled anti-human antibody to the antibody being examined, either IgM (acute phase) or IgG (convalescent phase), and measuring the amount of reporter bound to the solid support, as in the first method, or may involve observing the effect of antibody binding on a homogeneous assay reagent, as in the second method.

Also forming part of the invention is an assay system or kit for carrying out the assay method just described. The kit generally includes a support with surface-bound recombinant protein antigen which is (a) immunoreactive with antibodies present in individuals infected with enterically transmitted nonA/nonB viral agent and (b) derived from a viral hepatitis agent whose genome contains a region which is homologous to the 1.33 kb DNA EcoRI insert present in plasmid pTZKF1(ET1.1) carried in *E. Coli* strain BB4, and having ATCC deposit no. 67717. A reporter-labeled anti-human antibody in the kit is used for detecting surface-bound anti-ET-NANB antibody.

B. Viral Genome Diagnostic Applications

The genetic material of the invention can itself be used in numerous assays as probes for genetic material present in naturally occurring infections. One method for amplification of target nucleic acids, for later analysis by hybridization assays, is known as the polymerase chain reaction or PCR technique. The PCR technique can be applied to detecting virus particles of the invention in suspected pathological samples using oligonucleotide primers spaced apart from each other and based on the genetic sequence set forth above. The primers are complementary to opposite strands of a double stranded DNA molecule and are typically separated by from about 50 to 450 nt or more (usually not more than 2000 nt). This method entails preparing the specific oligonucleotide primers and then repeated cycles of target DNA denaturation, primer binding, and extension with a DNA polymerase to obtain DNA fragments of the expected length based on the primer spacing. Extension products generated from one primer serve as additional target sequences for the other primer. The degree of amplification of a target sequence is controlled by the number of cycles that are performed and is theoretically calculated by the simple formula $2^n$ where n is the number of cycles. Given that the average efficiency per cycle ranges from about 65% to 85%, 25 cycles produce from 0.3 to 4.8 million copies of the target sequence. The PCR method is described in a number of publications, including Saiki et al., Science (1985) 230:1350–1354; Saiki et al., Nature (1986) 324:163–166; and Scharf et al., Science (1986) 233:1076–1078. Also see U.S. Pat. Nos. 4,683,194; 4,683,195; and 4,683,202.

The invention includes a specific diagnostic method for determination of ET-NANB viral agent, based on selective amplification of ET-NANB fragments. This method employs a pair of single-strand primers derived from non-homologous regions of opposite strands of a DNA duplex fragment, which in turn is derived from an enterically transmitted viral hepatitis agent whose genome contains a region which is homologous to the 1.33 kb DNA EcoRI insert present in plasmid pTZKF1(ET1.1) carried in *E. coli* strain BB4, and having ATCC deposit no. 67717. These "primer fragments," which form one aspect of the invention, are prepared from ET-NANB fragments such as described in Section III above. The method follows the process for amplifying selected nucleic acid sequences as disclosed in U.S. Pat. No. 4,683,202, as discussed above.

C. Peptide Vaccine

Any of the antigens of the invention can be used in preparation of a vaccine. A preferred starting material for preparation of a vaccine is the particle antigen isolated from bile. The antigens are preferably initially recovered as intact particles as described above. However, it is also possible to prepare a suitable vaccine from articles isolated from other sources or non-particle recombinant antigens. When non-particle antigens are used (typically soluble antigens), proteins derived from the viral envelope or viral capsid are preferred for use in preparing vaccines. These proteins can be purified by affinity chromatography, also described above.

If the purified protein is not immunogenic per se, it can be bound to a carrier to make the protein immunogenic. Carriers include bovine serum albumin, keyhole limpet hemocyanin and the like. It is desirable, but not necessary, to purify antigens to be substantially free of human protein. However, it is more important that the antigens be free of proteins, viruses, and other substances not of human origin that may have been introduced by way of, or contamination of, the nutrient medium, cell lines, tissues, or pathological fluids from which the virus is cultured or obtained.

Vaccination can be conducted in conventional fashion. For example, the antigen, whether a viral particle or a protein, can be used in a suitable diluent such as water, saline, buffered salines, complete or incomplete adjuvants, and the like. The immunogen is administered using standard techniques for antibody induction, such as by subcutaneous administration of physiologically compatible, sterile solutions containing inactivated or attenuated virus particles or antigens. An immune response producing amount of virus particles is typically administered per vaccinizing injection, typically in a volume of one milliliter or less.

A specific example of a vaccine composition includes, in a pharmacologically acceptable adjuvant, a recombinant protein or protein mixture derived from an enterically transmitted nonA/nonB viral hepatitis agent whose genome contains a region which is homologous to the 1.33 kb DNA EcoRI insert present in plasmid pTZKF1(ET1.1) carried in *E. coli* strain BB4, and having ATCC deposit no. 67717. The vaccine is administered at periodic intervals until a significant titer of anti-ET-NANB antibody is detected in the serum. The vaccine is intended to protect against ET-NANB infection.

Particularly preferred are vaccines prepared using proteins expressed by the 406.3-2 and 406.4-2 clones described herein and equivalents thereof, including fragments of the expressed proteins. Since these clones have already been demonstrated to be reactive with a variety of human HEV-positive sera, their utility in protecting against a variety of HEV strains is indicated.

D. Prophylactic and Therapeutic Antibodies and Antisera

In addition to use as a vaccine, the compositions can be used to prepare antibodies to ET-NANB virus particles. The antibodies can be used directly as antiviral agents. To prepare antibodies, a host animal is immunized using the virus particles or, as appropriate, non-particle antigens native to the virus particle are bound to a carrier as described above for vaccines. The host serum or plasma is collected following an appropriate time interval to provide a composition comprising antibodies reactive with the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the FC portion of a foreign species antibody or using an antibody of the same species as the host animal, for example, the use of antibodies from human/human hybridomas.

The antibodies can also be used as a means of enhancing the immune response since antibody-virus complexes are recognized by macrophages. The antibodies can be administered in amounts similar to those used for other therapeutic administrations of antibody. For example, pooled gamma globulin is administered at 0.02–0.1 ml/lb body weight during the early incubation of other viral diseases such as rabies, measles and hepatitis B to interfere with viral entry into cells. Thus, antibodies reactive with the ET-NANB virus particle can be passively administered alone or in conjunction with another anti-viral agent to a host infected with an ET-NANB virus to enhance the immune response and/or the effectiveness of an antiviral drug.

Alternatively, anti-ET-NANB-virus antibodies can be induced by administering anti-idiotype antibodies as immunogens. Conveniently, a purified anti-ET-NANB-virus antibody preparation prepared as described above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-ET-NANB virus antibodies, or by affinity chromatography using anti-ET-NANB-virus antibodies bound to the affinity matrix. The anti-idiotype antibodies produced are similar in conformation to the authentic ET-NANB antigen and may be used to prepare an ET-NANB vaccine rather than using a ET-NANB particle antigen.

When used as a means of inducing anti-ET-NANB virus antibodies in a patient, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable. The anti-idiotype method of induction of anti-ET-NANB virus antibodies can alleviate problems which may be caused by passive administration of anti-ET-NANB-virus antibodies, such as an adverse immune response, and those associated with administration of purified blood components, such as infection with as yet undiscovered viruses.

The ET-NANB derived proteins of the invention are also intended for use in producing antiserum designed for pre- or post-exposure prophylaxis. Here an ET-NANB protein, or mixture of proteins is formulated with a suitable adjuvant and administered by injection to human volunteers, according to known methods for producing human antisera. Antibody response to the injected proteins is monitored, during a several-week period following immunization, by periodic serum sampling to detect the presence an anti-ET-NANB serum antibodies, as described in Section IIA above.

The antiserum from immunized individuals may be administered as a pre-exposure prophylactic measure for individuals who are at risk of contracting infection. The antiserum is also useful in treating an individual post-exposure, analogous to the use of high titer antiserum against hepatitis B virus for post-exposure prophylaxis.

E. Monoclonal Antibodies

For both in vivo use of antibodies to ET-NANB virus particles and proteins and anti-idiotype antibodies and diagnostic use, it may be preferable to use monoclonal antibodies. Monoclonal anti-virus particle antibodies or anti-idiotype antibodies can be produced as follows. The spleen or lymphocytes from an immunized animal are removed and immortalized or used to prepare hybridomas by methods known to those skilled in the art. To produce a human-human hybridoma, a human lymphocyte donor is selected. A donor known to be infected with a ET-NANB virus (where infection has been shown for example by the presence of anti-virus antibodies in the blood or by virus culture) may serve as a suitable lymphocyte donor. Lymphocytes can be isolate from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal anti-virus particle antibodies, the antibodies must bind to ET-NANB virus particles. For monoclonal anti-idiotype antibodies, the antibodies must bind to anti-virus particle antibodies. Cells producing antibodies of the desired specificity are selected.

The following examples illustrate various aspects of the invention, but are in no way intended to limit the scope thereof.

Material

The materials used in the following Examples were as follows:

Enzymes: DNAse I and alkaline phosphatase were obtained from Boehringer Mannheim Biochemicals (BMB, Indianapolis, Ind.); EcoRI, EcoRI methylase, DNA ligase, and DNA Polymerase I, from New England Biolabs (NEB, Beverly Mass.); and RNase A was obtained from Sigma (St. Louis, Mo.).

Other reagents: EcoRI linkers were obtained from NEB; and nitro blue tetrazolium (NBT), S-bromo-4-chloro-3-indolyl phosphate (BCIP) S-bromo-4-chloro-3-indolyl-B-D-galactopyranoside (Xgal) and isopropyl B-D-thiogalactopyranoside (IPTG) were obtained from Sigma.

cDNA synthesis kit and random priming labeling kits are available from Boehringer-Mannheim Biochemical (BMB, Indianapolis, Ind.).

EXAMPLE 1

Preparing cDNA Library

A. Source of ET-NANB virus

Two cynomolgus monkeys (cynos) were intravenously injected with a 10% suspension of a stool pool obtained from a second-passage cyno (cyno #37) infected with a strain of ET-NANB virus isolated from Burma cases whose stools were positive for ET-NANB, as evidenced by binding of 27–34 nm virus-like particles (VLPs) in the stool to immune serum from a known ETNANB patient. The animals developed elevated levels of alanine aminotransferase (ALT) between 24–36 days after inoculation, and one excreted 27–34 nm VLPs in its bile in the pre-acute phase of infection.

The bile duct of each infected animal was cannulated and about 1–3 cc of bile was collected daily. RNA was extracted from one bile specimen (cyno #121) by hot phenol extraction, using a standard RNA isolation procedure. Double-strand cDNA was formed from the isolated RNA by a random primer for first-strand generation, using a cDNA synthesis kit obtained from Boehringer-Mannheim (Indianapolis, Ind.).

B. Cloning the Duplex Fragments

The duplex cDNA fragments were blunt-ended with T4 DNA polymerase under standard conditions (Maniatis, p. 118), then extracted with phenol/chloroform and precipitated with ethanol. The blunt-ended material was ligated with EcoRI linkers under standard conditions (Maniatis, pp. 396–397) and digested with EcoRI to remove redundant linker ends. Non-ligated linkers were removed by sequential isopropanol precipitation.

Lambda gt10 phage vector (Huynh) was obtained from Promega Biotec (Madison, Wis.). This cloning vector has a unique EcoRI cloning site in the phage CI repressor gene. The cDNA fragments from above were introduced into the EcoRI site by mixing 0.5–1.0 μg EcoRI-cleaved gt10, 0.5–3 μl of the above duplex fragments, 0.5 μl 10× ligation buffer, 0.5 μl ligase (200 units), and distilled water to 5 μl. The mixture was incubated overnight at 14° C., followed by in vitro packaging, according to standard methods (Maniatis, pp. 256–268).

The packaged phage were used to infect an E. coli hfl strain, such as strain HG415. Alternatively, E. coli strain C600 hfl available from Promega Biotec, Madison, Wis., could be used. The percentage of recombinant plaques obtained with insertion of the EcoRI-ended fragments was less than 5% by analysis of 20 random plaques.

The resultant cDNA library was plated and phage were eluted from the selection plates by addition of elution buffer. After DNA extraction from the phage, the DNA was digested with EcoRI to release the heterogeneous insert population, and the DNA fragments were fractionated on agarose to remove phage fragments. The 500–4,000 basepair inserts were isolated and recloned into lambda gt10 as above, and the packaged phage was used to infect E. coli strain HG415. The percentage of successful recombinants was greater than 95%. The phage library was plated on E. coli strain HG415, at about 5,000 plaques/plate, on a total of 8 plates.

EXAMPLE 2

Selecting ET-NANB Cloned Fragments

A. cDNA Probes

Duplex cDNA fragments from noninfected and ETNANB-infected cynomolgus monkeys were prepared as in Example 1. The cDNA fragments were radiolabeled by random priming, using a random-priming labeling kit obtained from Boehringer-Mannheim (Indianapolis, Ind.).

B. Clone Selection

The plated cDNA library from Example 1 was transferred to each of two nitrocellulose filters, and the phage DNA was fixed on the filters by baking, according to standard methods (Maniatis, pp. 320323). The duplicate filters were hybridized with either infected-source or control CDNA probes from above. Autoradiographs of the filters were examined to identify library clones which hybridized with radiolabeled CDNA probes from infected source only, i.e., did not hybridize with cDNA probes from the non-infected source. Sixteen such clones, out of a total of about 40,000 clones examined, were identified by this subtraction selection method.

Each of the sixteen clones was picked and replated at low concentration on an agar plate. The clones on each plate were transferred to two nitrocellulose ag duplicate lifts, and examined for hybridization to radiolabeled cDNA probes from infected and noninfected sources, as above. Clones were selected which showed selective binding for infected-source probes (i.e., binding with infected-source probes and substantially no binding with non-infected-source probes). One of the clones which bound selectively to probe from infected source was isolated for further study. The selected vector was identified as lambda gt10-1.1, indicated in FIG. 1.

EXAMPLE 3

ET-NANB Sequence

Clone lambda gt10-1.1 from Example 2 was digested with EcoRI to release the heterologous insert, which was separated from the vector fragments by gel electrophoresis. The electrophoretic mobility of the fragment was consistent with a 1.33 kb fragment. This fragment, which contained EcoRI ends, was inserted into the EcoRI site of a pTZKF1 vector, whose construction and properties are described in co-owned U.S. patent application for "Cloning Vector System and Method for Rare Clone Identification", Ser. No. 125, 650, filed Nov. 25, 1987. Briefly, and as illustrated in FIG. 1, this plasmid contains a unique EcoRI site adjacent a T7 polymerase promoter site, and plasmid and phage origins of replication. The sequence immediately adjacent each side of the EcoRI site is known. E. coli BB4 bacteria, obtained from Stratagene (La Jolla, Calif., were transformed with the plasmid.

Radiolabeled ET-NANB probe was prepared by excising the 1.33 kb insert from the lambda gt10-1.1 phage in Example 2, separating the fragment by gel electrophoresis, and randomly labeling as above. Bacteria transfected with the above pTZKF1 and containing the desired ET-NANB insert were selected by replica lift and hybridization with the radiolabeled ET-NANB probe, according to methods outlined in Example 2.

One bacterial colony containing a successful recombinant was used for sequencing a portion of the 1.33 kb insert. This isolate, designated pTZKF1(ET1.1), has been deposited with the American Type Culture Collection, and is identified by ATCC deposit no. 67717. Using a standard dideoxy sequencing procedure, and primers for the sequences flanking the EcoRI site, about 200–250 basepairs of sequence from the 5'-end region and 3'-end region of the insert were obtained. The sequences are given above in Section II. Later sequencing by the same techniques gave the full sequence in both directions, also given above.

EXAMPLE 4

Detecting ET-NANB Sequences cDNA fragment mixtures from the bile of noninfected and ET-NANB-infected cynomolgus monkeys were prepared as above. The cDNA fragments obtained from human stool samples were prepared as follows. Thirty ml of a 10% stool suspension obtained from an individual from Mexico diagnosed as infected with ET-NANB as a result of an ET-NANB outbreak, and a similar volume of stool from a healthy, non-infected individual, were layered over a 30% sucrose density gradient cushion, and centrifuged at 25,000×g for 6 hr in an SW27 rotor, at 15° C. The pelleted material from the infected-source stool contained 27–34 nm VLP particles characteristic of ET-NANB infection in the infected-stool sample. RNA was isolated from the sucrose-gradient pellets in both the infected and non-infected samples, and the isolated RNA was used to produce cDNA fragments as described in Example 1.

The CDNA fragment mixtures from infected and non-infected bile source, and from infected and non-infected human-stool source were each amplified by a novel linker/primer replication method described in co-owned patent application Ser. No. 07/208,512 for "DNA Amplification and Subtraction Technique," filed Jun. 17, 1988. Briefly, the fragments in each sample were blunt-ended with DNA Pol I then extracted with phenol/chloroform and precipitated with ethanol. The blunt-ended material was ligated with linkers having the following sequence (top or 5' sequence has SEQ ID NO.3; bottom or 3'sequence has SEQ ID NO:4):

5'-GGAATTCGCGGCCGCTCG-3'
3'-TTCCTTAAGCGCCGGCGAGC-5'

The duplex fragments were digested with NruI to remove linker dimers, mixed with a primer having the sequence represented by SEQ ID NO:3, and then heat denatured and cooled to room temperature to form single-strand DNA/primer complexes. The complexes were replicated to form duplex fragments by addition of Thermus aquaticus (Taq) polymerase and all four deoxynucleotides. The replication procedures, involving successive strand denaturation, formation of strand/primer complexes, and replication, was repeated 25 times.

Figure 2:
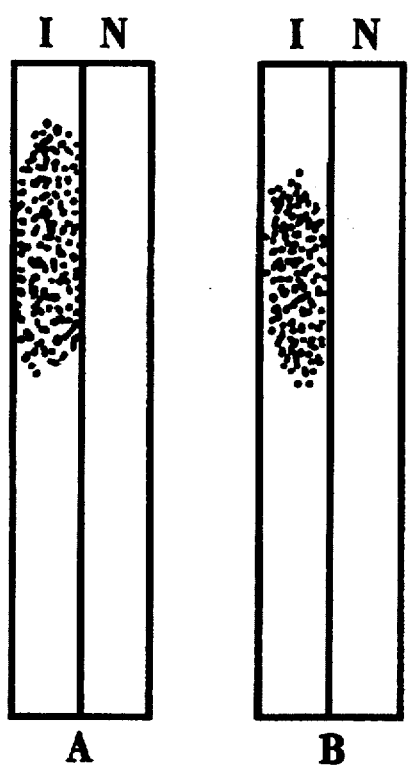
FIGS. 2A–2B are representations of Southern blots in which a radiolabeled ET-NANB probe was hybridized with amplified cDNA fragments prepared from RNA isolated from infected (I) and non-infected (N) bile sources (2A), and from infected (I) and non-infected (N) stool-sample sources (2B).

The amplified cDNA sequences were fractionated by agarose gel electrophoresis, using a 2% agarose matrix. After transfer of the DNA fragments from the agarose gels to nitrocellulose paper, the filters were hybridized to a random-labeled 32p probe prepared by (i) treating the pTZKF1(ET1.1) plasmid from above with EcoRI, (ii) isolating the released 1.33 kb ET-NANB fragment, and (iii) randomly labeling the isolated fragment. The probe hybridization wag performed by conventional Southern blotting methods (Maniatis, pp. 382–389). FIG. 2 shows the hybridization pattern obtained with cDNAs from infected (I) and non-infected (N) bile sources (2A) and from infected (I) and noninfected (N) human stool sources (2B). As seen, the ET-NANB probe hybridized with fragments obtained from both of the infected sources, but was non-homologous to sequences obtained from either of the non-infected sources, thus confirming the specificity of derived sequence.

Southern blots of the radiolabeled 1.33 kb fragment with genomic DNA fragments from both human and cynomolgus-monkey DNA were also prepared. No probe hybridization to either of the genomic fragment mixtures was observed, confirming that the ET-NANB sequence is exogenous to either human or cynomolgus genome.

EXAMPLE 5

Expressing ET-NANB Proteins

A. Preparing ET-NANB Coding Sequences

The pTZKF1(ET1.1) plasmid from Example 2 was digested with EcoRI to release the 1.33 kb ET-NANB insert which was purified from the linearized plasmid by gel electrophoresis. The purified fragment was suspended in a standard digest buffer (0.5M Tris HCl, pH 7.5; 1 mg/ml BSA; 10 mM MnCl2) to a concentration of about 1 mg/ml and digested with DNAse I at room temperature for about 5 minutes. These reaction conditions were determined from a prior calibration study, in which the incubation time required to produce predominantly 100–300 basepair fragments was determined. The material was extracted with phenol/chloroform before ethanol precipitation.

The fragments in the digest mixture were blunt-ended and ligated with EcoRI linkers as in Example 1. The resultant fragments were analyzed by electrophoresis (5–10 V/cm) on 1.2% agarose gel, using PhiX174/HaeIII and lambda/HindIII size markers. The 100–300 bp fraction was eluted onto NA45 strips (Schleicher and Schuell), which were then placed into 1.5 ml microtubes with eluting solution (1M NaCl, 50 mM arginine, pH 9.0), and incubated at 67° C. for 30–60 minutes. The eluted DNA was phenol/chloroform extracted and then precipitated with two volumes of ethanol. The pellet was resuspended in 20 μl.TE (0.01M Tris HCl, pH 7.5, 0.001M EDTA).

B. Cloning in an Expression Vector

Lambda gt11 phage vector (Huynh) was obtained from Promega Biotec (Madison, Wis.). This cloning vector has a unique EcoRI cloning site 53 base pairs upstream from the beta-galactosidase translation termination codon. The genomic fragments from above, provided either directly from coding sequences (Example 5) or after amplification of cDNA (Example 4), were introduced into the EcoRI site by mixing 0.5–1.0 μg EcoRI-cleaved gt11, 0.3–3 μl of the above sized fragments, 0.5 μl 10× ligation buffer (above), 0.5 μl ligase (200 units), and distilled water to 5 μl. The mixture was incubated overnight at 14° C., followed by in vitro packaging, according to standard methods (Maniatis, pp. 256–268).

The packaged phage were used to infect *E. coli* strain KM392, obtained from Dr. Kevin Moore, DNAX (Palo Alto, Calif.). Alternatively, *E. Coli* strain Y1090, available from the American Type Culture Collection (ATCC #37197), could be used. The infected bacteria were plated and the resultant colonies were checked for loss of beta-galactosidase activity-(clear plaques) in the presence of X-gal using a standard X-gal substrate plaque assay method (Maniatis). About 50% of the phage plaques showed loss of beta-galactosidase enzyme activity (recombinants).

C. Screening for ET-NANB Recombinant Proteins

ET-NANB convalescent antiserum was obtained from patients infected during documented ET-NANB outbreaks in Mexico, Borneo, Pakistan, Somalia, and Burma. The sera were immunoreactive with VLPs in stool specimens from each of several other patients with ET-NANB hepatitis.

A lawn of *E. coli* KM392 cells infected with about 104 pfu of the phage stock from above was prepared on a 150 mm plate and incubated, inverted, for 5–8 hours at 37° C. The lawn was overlaid with a nitrocellulose sheet, causing transfer of expressed ETNANB recombinant protein from the plaques to the paper. The plate and filter were indexed for matching corresponding plate and filter positions.

The filter was washed twice in TBST buffer (10 mM Tris, pH 8.0, 150 mM NaCl, 0.05% Tween 20), blocked with AIB (TBST buffer with 1% gelatin), washed again in TBST, and incubated overnight after addition of antiserum (diluted to 1:50 in AIB, 12–15 ml/plate). The sheet was washed twice in TBST and then contacted with enzyme-labeled anti-human antibody to attach the labeled antibody at filter sites containing antigen recognized by the antiserum. After a final washing, the filter was developed in a substrate medium containing 33 μl NBT (50 mg/ml stock solution maintained at 4° C.) mixed with 16 μl BCIP (50 mg/ml stock solution maintained at 4° C.) in 5 ml of alkaline phosphatase buffer (100 mM Tris, 9.5, 100 mM NaCl, 5 mM MgCl2). Purple color appeared at points of antigen production, as recognized by the antiserum.

D. Screening Plating

The areas of antigen production determined in the previous step were replated at about 100–200 pfu on an 82 mm plate. The above steps, beginning with a 5–8 hour incubation, through NBT-BCIP development, were repeated in order to plaque purify phage secreting an antigen capable of reacting with the ET-NANB antibody. The identified plaques were picked and eluted in phage buffer (Maniatis, p. 443).

E. Epitope Identification

A series of subclones derived from the original pTZKF1 (ET1.1) plasmid from Example 2 were isolated using the same techniques described above. Each of these five subclones were immunoreactive with a pool of anti-ET antisera noted in C. The subclones contained short sequences from the "reverse" sequence set forth previously. The beginning and ending points of the sequences in the subclones (relative to the full "reverse" sequence), are identified in the table below.

TABLE 1

| | Position in "Reverse" Sequence | |
|---|---|---|
| Subclone | 5'-end | 3'-end |
| Y1 | 522 | 643 |
| Y2 | 594 | 667 |
| Y3 | 508 | 665 |
| Y4 | 558 | 752 |
| Y5 | 545 | 665 |

Since all of the gene sequences identified in the table must contain the coding sequence for the epitope, it is apparent that the coding sequence for the epitope falls in the region between nucleotide 594 (5'-end) and 643 (3'-end). Genetic sequences equivalent to and complementary to this relatively short sequence are therefore particularly preferred aspects of the present invention, as are peptides produced using this coding region.

A second series of clones identifying an altogether different epitope was isolated with only Mexican serum.

TABLE 2

| | Position in "Forwaard" Sequence | |
|---|---|---|
| Subclone | 5' end | 3' end |
| ET 2-2 | 2 | 193 |
| ET 8-3 | 2 | 135 |
| ET 9-1 | 2 | 109 |
| ET 13-1 | 2 | 101 |

The coding system for this epitope falls between nucleotide 2 (S-end) and 101 (3-end). Genetic sequences related to this short sequence are therefore also preferred, as are peptides produced using this coding region.

Two particularly preferred subclones for use in preparing polypeptides containing epitopes specific for HEV are the 406.3-2 and 406.4-2 clones whose sequences are set forth above. These sequences were isolated from an amplified cDNA library derived from a Mexican stool. Using the techniques described in this section, polypeptides expressed by these clones have been tested for immunoreactivity against a number of different human HEV-positive sera obtained from sources around the world. As shown in Table 3 below, 8 sera immunoreactive with the polypeptide expressed by the 406.4-2, and 6 sera immunoreacted with polypeptide expressed by the 406.3-2 clone.

For comparison, the Table also shows reactivity of the various human sera with the Y2 clone identified in Table 1 above. Only one of the sera reacted with the polypeptide expressed by this clone. No immunoreactivity was seen for normal expression products of the gt11 vector.

TABLE 3

| | | Immunoreactivity of HEV Recombinant Proteins: Human Sera | | | | |
|---|---|---|---|---|---|---|
| Sera | Source | Stage[1] | 406.3-2 | 406.4-2 | Y2 | λgt11 |
| FVH-21 | Burma | A | - | - | - | - |
| FVH-8 | Burma | A | - | + | + | - |
| SOM-19 | Somalia | A | + | + | - | - |
| SOM-20 | Somalia | A | + | + | - | - |
| IM-35 | Borneo | A | + | + | - | - |
| IM-36 | Borneo | A | - | - | - | - |
| PAK-1 | Pakistan | A | + | + | - | - |
| FFI-4 | Mexico | A | + | + | - | - |
| FFI-125 | Mexico | A | - | + | - | - |
| F 387 IC | Mexico | C | + | + | ND | - |
| Normal | U.S.A. | — | - | - | - | - |

[1]A = acute; C = convalescent

While the invention has been described with reference to particular embodiments, methods, construction and use, it will be apparent to those skilled in the art that various changes and modifications can be made without departing from the invention.

We claim:

1. An isolated protein which is (a) specifically immunoreactive with antibodies present in individuals infected with hepatitis E virus (HEV) and (b) encoded by a sequence contained in an open reading frame (ORF) in an HEV genome, where said genome has a sequence that is greater than 70% identical with the sequence presented as SEQ ID NO:6.

2. The protein of claim 1, wherein said protein is a recombinant protein.

3. The protein of claim 1, wherein said genome has the sequence presented as SEQ ID NO:6.

4. The protein of claim 1, wherein said genome has the sequence presented as SEQ ID NO:10.

5. The protein of claim 1, wherein said open reading frame is the second open reading frame (ORF2) of said HEV genome.

6. The protein of claim 5, wherein said ORF2 has the sequence presented as SEQ ID NO:8.

7. The protein of claim 6, wherein said protein has the sequence presented as SEQ ID NO:8.

8. The protein of claim 5, wherein said protein contains a sequence selected from the group consisting of SEQ ID NO:19 and SEQ ID NO:20.

9. The protein of claim 8, wherein said protein has the sequence SEQ ID NO:19.

10. The protein of claim 8, wherein said protein has the sequence SEQ ID NO:20.

11. The protein of claim 1, wherein said open reading frame is the third open reading frame (ORF3) of said HEV genome.

12. The protein of claim 11, wherein said ORF3 has the sequence presented as SEQ ID NO:9.

13. The protein of claim 12, wherein said protein has the sequence presented as SEQ ID NO:9.

14. The protein of claim 12, wherein said protein contains a sequence selected from the group consisting of SEQ ID NO:17 and SEQ ID NO:18.

15. The protein of claim 14, wherein said protein has the sequence SEQ ID NO:17.

16. The protein of claim 14, wherein said protein has the sequence SEQ ID NO:18.

17. A protein composition, comprising
    (i) an isolated protein encoded by an open reading frame (ORF) in a hepatitis E virus (HEV) genome, where said genome has a sequence that is greater than 70% identical with the sequence presented as SEQ ID NO:6, or
    (ii) a fragment of said isolated protein having a length of at least about 30 amino acids.

18. The composition of claim 17, wherein said protein is a recombinant protein.

19. The composition of claim 17, wherein said genome has the sequence presented as SEQ ID NO:6.

20. The composition of claim 17, wherein said genome has the sequence presented as SEQ ID NO:10.

21. The composition of claim 17, wherein said open reading frame is the first open reading frame (ORF1) of said HEV genome.

22. The composition of claim 21, wherein said ORF1 has the sequence presented as SEQ ID NO:7.

23. The composition of claim 22, wherein said protein has the sequence presented as SEQ ID NO:7.

24. The composition of claim 17, wherein said open reading frame is the second open reading frame (ORF2) of said HEV genome.

25. The composition of claim 24, wherein said ORF2 has the sequence presented as SEQ ID NO:8.

26. The composition of claim 25, wherein said protein has the sequence presented as SEQ ID NO:8.

27. The composition of claim 24, wherein said protein contains a sequence selected from the group consisting of SEQ ID NO:19 and SEQ ID NO:20.

28. The composition of claim 27, wherein said protein has the sequence SEQ ID NO:19.

29. The composition of claim 27, wherein said protein has the sequence SEQ ID NO:20.

30. The composition of claim 17, wherein said open reading frame is the third open reading frame (ORF3) of said HEV genome.

31. The composition of claim 30, wherein said ORF3 has the sequence presented as SEQ ID NO:9.

32. The composition of claim 31, wherein said protein has the sequence presented as SEQ ID NO:9.

33. The composition of claim 32, wherein said protein contains a sequence selected from the group consisting of SEQ ID NO:17 and SEQ ID NO:18.

34. The composition of claim 33, wherein said protein has the sequence SEQ ID NO:17.

35. The composition of claim 33, wherein said protein has the sequence SEQ ID NO:18.

* * * * *